US008088787B2

(12) United States Patent
Hong et al.

(10) Patent No.: US 8,088,787 B2
(45) Date of Patent: Jan. 3, 2012

(54) METHODS RELATED TO THE TREATMENT OF NEURODEGENERATIVE AND INFLAMMATORY CONDITIONS

(75) Inventors: Jau-Shyong Hong, Durham, NC (US); Liya Qin, Durham, NC (US); Guorong Li, Chapel Hill, NC (US); Michelle Block, Holly Springs, NC (US); Wei Zhang, Dalian (CN); Po-See Chen, Taipei (TW); Giia-Shuen Peng, Taipei (TW)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 1061 days.

(21) Appl. No.: 11/596,296

(22) PCT Filed: May 12, 2005

(86) PCT No.: PCT/US2005/016691
§ 371 (c)(1),
(2), (4) Date: Aug. 10, 2007

(87) PCT Pub. No.: WO2005/112931
PCT Pub. Date: Dec. 1, 2005

(65) Prior Publication Data
US 2008/0038199 A1 Feb. 14, 2008

Related U.S. Application Data

(60) Provisional application No. 60/570,566, filed on May 12, 2004.

(51) Int. Cl.
*A61K 31/485* (2006.01)
(52) U.S. Cl. .................................................. 514/282
(58) Field of Classification Search .................. None
See application file for complete search history.

(56) References Cited

U.S. PATENT DOCUMENTS

| 3,995,056 | A | * | 11/1976 | Allais et al. ............... 514/570 |
| 4,358,440 | A | * | 11/1982 | Fujino et al. ................ 514/12 |
| 4,806,543 | A | | 2/1989 | Choi |
| 4,863,928 | A | * | 9/1989 | Atkinson et al. ............ 514/282 |
| 4,994,466 | A | | 2/1991 | Sherman et al. |
| 5,166,207 | A | | 11/1992 | Smith |
| 5,229,394 | A | | 7/1993 | Salazar-Grueso |
| 5,414,017 | A | * | 5/1995 | Delaney et al. ............. 514/512 |
| 6,586,443 | B1 | | 7/2003 | Bihari et al. |

FOREIGN PATENT DOCUMENTS

| EP | 0 377 272 A2 | 7/1990 |
| WO | WO 00/38669 | 7/2000 |
| WO | WO 02/102989 A2 | 12/2002 |

OTHER PUBLICATIONS

Canady et al. "Use of Naloxone in Septic Shock," J. National Medical Assoc., 1989, 81, 669-673.*

Powell et al. "Paradoxical Effects of the Opioid Antagonist Naltrexone on Morphine Analgesia, Tolerance, and Reward in Rats," The Journal of Pharmacology and Experimental Therapeutics, 2002, 300, 588-596.*
Gan et al. ("Opioid-sparing effects of a low-dose infusion of naloxone in patient-administered morphine sulfate" Anesthesiology, 1997, 87, 1075-81).*
Crain & Shen ("Ultra-low concentrations of naloxone selectively antagonize excitatory effects of morphine on sensory neurons, thereby increasing its antinociceptive potency and attenuating tolerance/dependence during chronic cotreatment," Proc. Natl. Acad. Sci. USA, 1995, 92, 10540-4).*
Amar, S. et al., "Tumor Necrosis Factor (TNF)-Induced Cutaneous Necrosis is Mediated by TNF Receptor 1," *Journal of Inflammation*, vol. 47, pp. 180-189 (1996).
Bradham, C. et al., "Mechanisms of Hepatic Toxicity. I. TNF-induced liver injury," *Am. J.Physiol*, vol. 275, pp. G387-G392 (1998).
Brenneman, D. et al., "A Femtomolar-acting Neuroprotective Peptide," *The Journal of Clinical Investigation*, vol. 97, No. 10, pp. 2299-2307 (May 1996).
Britton, P. et al., "Dextromethorphan protects against cerebral injury following transient, but not permanent, focal ischemia in rats," *Life Sciences*, vol. 60, No. 20, pp. 1729-1740 (1997).
Calabrese, E. et al., "Peptides and Hormesis," *Critical Reviews in Toxicology*, vol. 33, Nos. 3 & 4, pp. 355-405 (2003).
Choi, D., "Dextrorphan and dextromethorphan attenuate glutamate neurotoxicity," *Brain Research*, vol. 403, pp. 333-336 (1987).
Christensen, S. et al. ,"Insulin produces a biphasic response in *Tetrahymena thermophila* by stimulating cell survival and activating proliferation in two separate concentration intervals," *Cell Biology International*, vol. 20, No. 6, pp. 437-444 (1996).
Cruciani, R. et al., "Ultra-Low Dose Oral Naltrexone Decreases Side Effects and Potentiates the Effect of Methadone," *Journal of Pain and Symptom Management*, vol. 25, No. 6, pp. 491-494 (Jun. 2003).
Daniel, C. et al., "Thrombospondin-1 is a major activator of TGF-β in fibrotic renal disease in the rat in vivo," *Kidney International*, vol. 65, pp. 459-468 (2004).
Dickson, D. et al., "Microglia and Cytokines in Neurological Disease, with Special Reference to AIDS and Alzheimer's Disease," *Glia*, vol. 7, pp. 75-83 (1993).
Elliott, K. et al., "Dextromethorphan attenuates and reverses analgesic tolerance to morphine," *Pain*, vol. 59, pp. 361-368 (1994).

(Continued)

*Primary Examiner* — Christina Bradley
(74) *Attorney, Agent, or Firm* — Edwards Wildman Palmer LLP; Peter F. Corless; Andrew W. Shyjan, Esq.

(57) ABSTRACT

The invention includes methods of neuroprotection, inducing release of neurotrophic factors, inhibiting the over-activation of innate immune cells, attenuating the toxin-induced death and/or damage of tissues, reducing inflammation, treating an inflammation-related condition, and inhibiting NADPH oxidase, that includes contacting or administering an effective amount of at least one compound of the invention that include: valproic acid, sodium butyrate, and salts thereof; opioid peptides; a peptide comprising the tripeptide GGF; and morphinans, such as naloxone, naltrexone, 3-hydroxymorphinan and dextromethorphan.

2 Claims, 65 Drawing Sheets

OTHER PUBLICATIONS

Enomoto, N. et al., "Protective Effect of Thalidomide on Endotoxin-Induced Liver Injury," *Alcoholism: Clinical and Experimental Research*, vol. 27, No. 8, Supplement, pp. 2S-6S (Aug. 2003).

Essani, N. et al., "Transcriptional Activation of Vascular Cell Adhesion Molecule-1 Gene in Vivo and its Role in the Pathophysiology of Neutrophil-Induced Liver Injury in Murine Endotoxin Shock," *The Journal of Immunology*, vol. 158, pp. 5941-5948 (1997).

Fridovich, I., "Superoxide Anion Radical (O2-.), Superoxide Dismutases, and Related Matters," *The Journal of Biological Chemistry*, vol. 272, No. 30, pp. 18515-18517 (Jul. 25, 1997).

Gao, H. et al., "Microglial activation-mediated delayed and progressive degeneration of rat nigral dopaminergic neurons: relevance to Parkinson's disease," *Journal of Neurochemistry*, vol. 81, pp. 1285-1297 (2002).

Gao, H. et al., "Novel anti-inflammatory therapy for Parkinson's disease," *TRENDS in Pharmacological Sciences*, vol. 24, No. 8, pp. 395-401 (Aug. 2003).

Gatley, S. et al., "The Effects of Diphenyleneiodonium on Mitochondrial Reactions," *Biochem. J.*, vol. 158, pp. 307-315 (1976).

George, C. et al., "Dextromethorphan reduces neocortical ischemic neuronal damage in vivo," *Brain Research*, vol. 440, pp. 375-379 (1988).

Giulian, D., "Microglia and the Immune Pathology of Alzheimer Disease," *Am. J. Hum. Genet.*, vol. 65, pp. 13-18 (1999).

Göorlach, A. et al., "Redox Signaling through NADPH Oxidases: Involvement in Vascular Proliferation and Coagulation," *Annals New York Academy of Sciences*, vol. 973, pp. 505-507 (2002).

Gozes, I. et al., "A Novel Signaling Molecule for Neuropeptide Action: Activity-dependent Neuroprotective Protein," *Annals New York Academy of Sciences*, vol. 897, pp. 125-135 (1999).

Greenamyre, J. et al., "Mitochondrial dysfunction in Parkinson's disease," *Biochem. Soc. Symp.*, vol. 66, pp. 85-97 (1999).

Gröne, H., "Vasculitits—Aspects of Cellular and Molecular Pathogenesis," *Verh. Dtsch. Ges. Path.*, vol. 85, pp. 142-152 (2001).

Hamann, S. et al., "Ultra-low dose of naltrexone attenuates neuropathic but not acute pain in rats," *Experimental Biology 2004: Meeting Abstracts*, Abstract No. 635.8, p. A961 (2004).

Hewett, J. et al., "Hepatic and Extrahepatic Pathobiology of Bacterial Lipopolysaccharides," *Pharmacological Reviews*, vol. 45, No. 4, pp. 381-411 (1993).

Holst, O. et al., "Biochemistry and cell biology of bacterial endotoxins," *FEMS Immunology and Medical Microbiology*, vol. 16, pp. 83-104 (1996).

Jaeschke, H., "Mechanisms of Oxidant Stress-Induced Acute Tissue Injury," *Proceedings of the Society for Experimental Biology and Medicine*, vol. 209, No. 2, pp. 104-111 (Jun. 1995).

Jaeschke, H. et al., "Mechanisms of Hepatotoxicity," *Toxicological Sciences*, vol. 65, pp. 166-176 (2002).

Janabi, M. et al., "Oxidized LDL-Induced NF-κB Activation and Subsequent Expression of Proinflammatory Genes are Defective in Monocyte-Derived Macrophages from CD36-Deficient Patients," *Arterioscler Thromb Vasc Biol.*, vol. 20, pp. 1953-1960 (Aug. 2000).

Jenner, P., "Oxidative stress in Parkinson's disease and other neurodegenerative disorders," *Path Biol.*, vol. 44, No. 1, pp. 57-64 (Jan. 1996).

Jeohn, G. et al., "Synergistic neurotoxic effects of combined treatments with cytokines in murine primary mixed neuron/glia cultures," *Journal of Neuroimmunology*, vol. 85, pp. 1-10 (1998).

Jiang, J. et al., "Effect of hemorrhagic shock on endotoxin-inducing TNF production and intra-tissue lipopolysaccharide-binding protein mRNA expression and their relationship," *Shock*, vol. 7, No. 3, pp. 206-210 (Mar. 1997).

Kaplowitz, N. et al., "Oxidative Stress and Liver Disease," *Progress in Liver Diseases*, vol. 14, Chapter 6, pp. 131-159 (1996).

Kaiser, J., "Sipping from a Poisoned Chalice," *Science*, vol. 302, pp. 376-379 (Oct. 17, 2003).

Kaneider, N. et al., "Heparan Sulfate Proteoglycans are Involved in Opiate Receptor-Mediated Cell Migration," *Biochemistry*, vol. 43, No. 1, pp. 237-244 (2004).

Kim, W. et al., "Regional Difference in Susceptibility to Lipopolysaccharide-Induced Neurotoxicity in the Rat Brain: Role of Microglia," *The Journal of Neuroscience*, vol. 20, No. 16, pp. 6309-6316 (Aug. 15, 2000).

Kuttan, S. et al., "Endothelium-Dependent Response of the Rabbit Aorta to Femtomolar Concentrations of Angiotensin II," *Journal of Cardiovascular Pharmacology*, vol. 17, No. 6, p. 929-934 (1991).

Lehmann, V. et al., "Lethal toxicity of lipopolysaccharide and tumor necrosis factor in normal and D-galactosimine-treated mice," *J. Exp. Med.*, vol. 165, pp. 657-663 (Mar. 1987).

Leist, M. et al., "Tumor Necrosis Factor-Induced Hepatocyte Apoptosis Precedes Liver Failure in Experimental Murine Shock Models," *American Journal of Pathology*, vol. 146, No. 5, pp. 1220-1234 (May 1995).

Liu, B. et al., "Naloxone Protects Rat Dopaminergic Neurons against Inflammatory Damage through Inhibition of Microglia Activation and Superoxide Generation," *The Journal of Pharmacology and Experimental Therapeutics*, vol. 293, No. 2, pp. 607-617 (2000).

Liu, B. et al., "Reduction by naloxone of lipopolysaccharide-induced neurotoxicity in mouse cortical neuron-glia co-cultures," *Neuroscience*, vol. 97, No. 4, pp. 749-756 (2000).

Liu, B. et al., "Systemic Infusion of Naloxone Reduces Degeneration of Rat Substantia Nigral Dopaminergic Neurons Induced by Intranigral Injection of Lipopolysaccharide," *The Journal of Pharmacology and Experimental Therapeutics*, vol. 295, No. 1, pp. 125-132 (2000).

Liu, B. et al., "Femtomolar Concentrations of Dynorphins Protect Rat Mesencephalic Dopaminergic Neurons against Inflammatory Damage," *The Journal of Pharmacology and Experimental Therapeutics*, vol. 298, No. 3, pp. 1133-1141 (2001).

Liu, B. et al., "Primary Rat Mesencephalic Neuron-Glia, Neuron-Enriched, Microglia-Enriched, and Astroglia-Enriched Cultures," *Methods in Molecular Medicine Drugs of Abuse: Neurological Reviews and Protocols*, vol. 79, pp. 387-395 (2003).

Liu, B. et al., "Role of Microglia in Inflammation-Mediated Neurodegenerative Diseases: Mechanisms and Strategies for Therapeutic Intervention," *The Journal of Pharmacology and Experimental Therapeutics*, vol. 304, No. 1, pp. 1-7 (2003).

Liu, J. et al., "Role of intracellular thiol depletion, mitochondrial dysfunction and reactive oxygen species in *Salvia Miltiorrhiza*-induced apoptosis in human hepatoma HepG$_2$ cells," *Life Sciences*, vol. 69, pp. 1833-1850 (2001).

Liu, J. et al., "$O^2$-Vinyl 1-(Pyrrolidin-1-yl)diazen-1-ium-1,2-diolate Protection Against D-Galactosamine/Endotoxin-Induced Hepatotoxicity in Mice: Genomic Analysis Using Microarrays," *The Journal of Pharmacology and Experimental Therapeutics*, vol. 300, No. 1, pp. 18-25 (2002).

Liu, J. et al., "Acute cadmium exposure induces stress-related gene expression in wild-type and metallothionein-I/II-null mice," *Free Radical Biology & Medicine*, vol. 32, No. 6, pp. 525-535 (2002).

Liu, J. et al., "The Nitric Oxide Donor, V-PRRO/NO, Protects Against Acetaminophen-Induced Hepatotoxicity in Mice," *Hepatology*, vol. 37, No. 2, pp. 324-333 (Feb. 2003).

Liu, Y. et al., "Inhibition by Naloxone Steroisomers of β-Amyloid Peptide (1-42)-induced Superoxide Production in Microglia and Degeneration of Cortical and Mesencephalic Neurons," *The Journal of Pharmacology and Experimental Therapeutics*, vol. 302, No. 3, pp. 1212-1219 (2002).

Liu, Y. et al., "Dextromethorphan Protects Dopaminergic Neurons against Inflammation-Mediated Degeneration through Inhibition of Microglial Activation," *The Journal of Pharmacology and Experimental Therapeutics*, vol. 305, No. 1, pp. 212-218 (2003).

Lomas, J. et al., "Differential effects of macrophage inflammatory chemokine-2 and keratinocyte-derived chemokine on hemorrhage-induced neutrophil priming for lung inflammation: assessment by adoptive cells transfer in mice," *Shock*, vol. 19, No. 4, pp. 358-365 (Apr. 2003).

Makman, M. et al., "Presence and characterization of nociceptin (orphanin FQ) receptor binding in adult rat and human fetal hypothalamus," *Brain Research*, vol. 762, pp. 247-250 (1997).

Mao, J. et al,. "Oral administration of dextromethorphan prevents the devlopment of morphine tolerance and dependence in rats," *Pain*, vol. 67, pp. 361-368 (1996).

McColl, S. et al., "Inhibition of Murine Neutrophil Recruitment in Vivo by CXC Chemokine Receptor Antagonists," *The Journal of Immunology*, vol. 163, pp. 2829-2835 (1999).

McGeer, P. et al., "Reactive microglia are positive for HLA-DR in the substantia nigra of Parkinson's and Alzheimer's disease brains," *Neurology*, vol. 38, pp. 1285-1291 (Aug. 1988).

McGeer, P. et al., "The inflammatory response system of brain: implications for therapy of Alzheimer and other neurodegenerative diseases," *Brain Research Reviews*, vol. 21, pp. 195-218 (1995).

Meng, X. et al., "TNF-β and myocardial depression in endotoxemic rats: temporal discordance of an obligatory relationship," *Am. J. Physiol.*, vol. 275, pp. R502-R508 (1998).

Monyer, H. et al., "Morphinans attenuate cortical neuronal injury induced by glucose deprivation in vitro," *Brain Research*, vol. 446, pp. 144-148 (1988).

Nolan, J., "The role of endotoxin in liver injury," *Gastroenterology*, vol. 69, No. 6, pp. 1346-1356 (Dec. 1975).

Peskin, A. et al., "A microtiter plate assay for superoxide dismutase using a water-soluble tetrazolium salt (WST-1)," *Clinica Chimica Acta*, vol. 293, pp. 157-166 (2000).

Prince, D. et al., "Dextromethorphan protects against cerebral infarction in a rat model of hypoxia-ischemia," *Neuroscience Letters*, vol. 85, pp. 291-296 (1988).

Qin, L. et al., "NADPH Oxidase Mediates Lipopolysaccharide-induced Neurotoxicity and Proinflammatory Gene Expression in Activated Microglia," *The Journal of Biological Chemistry*, vol. 279, No. 2, pp. 1415-1421 (Jan. 9, 2004).

Qin, L. et al., "Microglial NADPH oxidase is a novel target for femtomolar neuroprotection against oxidative stress," *The FASEB Journal*, vol. 19, pp. 550-557 (Apr. 2005).

Reglodi, D. et al., "Effects of pretreatment with PACAP on the infarct size and functional outcome in rat permanent focal cerebral ischemia," *Peptides*, vol. 23, pp. 2227-2234 (2002).

Riendeau, D. et al., "Biochemical and pharmacological profile of a tetrasubstituted furanone as a highly selective COX-2 inhibitor," *British Journal of Pharmacology*, vol. 121, pp. 105-117 (1997).

Salkowski, C. et al., "Regulation of Inducible Nitric Oxide Synthase Messenger RNA Expression and Nitric Oxide Production by Lipopolysaccharide In Vivo," *The Journal of Immunology*, vol. 158, pp. 905-912 (1997).

Saquib, M. et al., "Photocatalytic Degradation of Two Selected Textile Dye Derivatives, Eosine Yellowish and ρ-Rosaniline, in Aqueous Suspensions of Titanium Dioxide," *Journal of Environmental Science and Health Part A: Toxic/Hazardous Substances & Environmental Engineering*, vol. A38, No. 11, pp. 2581-2598 (2003).

Semchuk, K. et al., "Parkinson's disease: A test of the multifactorial etiologic hypothesis," *Neurology*, vol. 43, pp. 1173-1180 (Jun. 1993).

Sies, H., "Physiological society symposium: impaired endothelial and smooth muscle cell function in oxidative stress," *Experimental Physiology*, vol. 82, pp. 291-295 (1997).

Souza, H. et al., "Vascular NAD(P)H oxidase is distinct from the phagocytic enzyme and modulates vascular reactivity control," *Am. J. Physiol. Heart Circ. Physiol.*, vol. 280, pp. H658-H667 (2001).

Spolarics, Z., "Endotoxin stimualates gene expression of ROS-eliminating pathways in rat hepatic endothelial and Kupffer cells," *Am. J. Physiol.*, vol. 270, pp. G660-G666 (1996).

Spolarics, Z., "Endotoxemia, pentose cycle, and the oxidant/antioxidant balance in the hepatic sinusoid," *Journal of Leukocyte Biology*, vol. 63, pp. 534-541 (May 1998).

Stebbing, A., "A Mechanism for Hormesis—A Problem in the Wrong Discipline," *Critical Reviews in Toxicology*, vol. 33 (Nos. 3 & 4), pp. 463-467 (2003).

Steel, D. et al., "The major acute phase reactants: C-reactive protein, serum amyloid P component and serum amyloid A protein," *Immunology Today*, vol. 15, No. 2, pp. 81-88 (1994).

Steinberg, G. et al., "Dextromethorphan Protects Against Cerebral Injury Following Transient Focal Ischemia in Rabbits," *Stroke*, vol. 19, No. 9, pp. 1112-1118 (Sep. 1988).

Swiatkowska, M. et al., "Reactive oxygen species upregulate expression of PAI-1 in endothelial cells," *Cellular & Molecular Biology Letters*, vol. 7, No. 4, pp. 1065-1071 (2002).

Tan, A. et al., "Superoxide produced by activated neutrophils efficiently reduces the tetrazolium salt, WST-1 to produce a soluble formazan: a simple colorimetric assay for measuring respiratory burst activation and for screening anti-inflammatory agents," *Journal of Immunological Methods*, vol. 238, pp. 59-68 (2000).

Thijs, L. et al., "Multiple Organ Failure in Septic Shock," *Current Topics in Microbiology and Immunology*, vol. 216, pp. 209-237 (1996).

Tortella, F. et al., "Neuroprotection (Focal Ischemia) and Neurotoxicity (Electroencephalographic) Studies in Rats with AHN649, a 3-Amino Analog of Dextromethorphan and Low-Affinity $N$-Methyl-D-Aspartate Antagonist," *The Journal of Pharmacology and Experimental Therapeutics*, vol. 291, No. 1, pp. 399-408 (1999).

Ulbrich, H. et al., "Cyclooxygenase-½ (COX-1/COX-2) and 5-lipoxygenase (5-LOX) inhibitors of the 6,7-diaryl-2,3-1$H$-dihydropyrrolizine type," *European Journal of Medicinal Chemistry*, vol. 37, pp. 953-959 (2002).

Vincent, J., "Definition and Pathogenesis of Septic Shock," *Current Topics in Microbiology and Immunology*, vol. 216, pp. 1-13 (1996).

Walker, N., "Real-Time and Quantitative PCR: Applications to Mechanism-Based Toxicology," *J. Biochem. Molecular Toxicology*, vol. 15, No. 3, pp. 121-127 (2001).

Wang, H. et al., "Quantifying cellular oxidative stress by dichlorofluorescein assay using microplate reader," *Free Radical Biology & Medicine*, vol. 27, Nos. 5/6, pp. 612-616 (1999).

Wang, T. et al., "The role of NF-κB in the regulation of cell stress responses," *International Immunopharmacology*, vol. 2, pp. 1509-1520 (2002).

Weinbroum, A. et al., "The role of dextromethorphan in pain control," *Canadian Journal of Anesthesia*, vol. 47, No. 6, pp. 585-596 (2000).

Wenzel, R. et al., "Current Understanding of Sepsis," *Clinical Infectious Diseases*, vol. 22, pp. 407-412 (Mar. 1996).

Wichterman, K. et al., "Sepsis and Septic Shock—A Review of Laboratory Models and a Proposal," *Journal of Surgical Research*, vol. 29, No. 2, pp. 189-201 (Aug. 1980).

Wilkemeyer, M. et al., "Peptide Antagonists of Ethanol Inhibition of L1-Mediated Cell-Cell Adhesion," *The Journal of Pharmacology and Experimental Therapeutics*, vol. 303 No. 1, pp. 110-116 (2002).

Wu, D. et al., "NADPH oxidase mediates oxidative stress in the 1-methyl-4-phenyl-1,2,3,6-tetrahydropyridine model of Parkinson's disease," *PNAS*, vol. 100, No. 10, pp. 6145-6150 (May 13, 2003).

Xia, Y. et al., "Inducible Nitric-oxide Synthase Generates Superoxide from the Reductase Domain," *The Journal of Biological Chemistry*, vol. 273, No. 35, pp. 22635-22639 (Aug. 28, 1998).

Yin, M. et al., "Alcohol-Induced Free Radicals in Mice: Direct Toxicants or Signaling Molecules?," *Hepatology*, vol. 34, pp. 935-942 (Nov. 2001).

Yoshida, L. et al., "Mutation at Histidine 338 of gp91$^{phox}$ Depletes FAD and Affects Expression of Cytochrome $b_{558}$ of the Human NADPH Oxidase," *The Journal of Biological Chemistry*, vol. 273, No. 43, pp. 27879-27886 (Oct. 23, 1998).

Yu, L. et al., "Biosynthesis of the Phagocyte NADPH Oxidase Cytochrome $b_{558}$," *The Journal of Biological Chemistry*, vol. 272, No. 43, pp. 27288-27294 (Oct. 24, 1997).

Zhang, X. et al., "Redundant function of macrophage inflammatory protein-2 and KC in tumor necrosis factor-α-induced extravasation of neutrophils in vivo," *European Journal of Pharmacology*, vol. 427, pp. 277-283 (2001).

\* cited by examiner

Normal control

LPS/GalN alone

DM + LPS/GalN 6 h

Control

6h

VPA, 0.6 mM 24 h

Control

24h

VPA, 0.6 mM

48 h

Control

48h

VPA, 0.6 mM

METHODS RELATED TO THE TREATMENT OF NEURODEGENERATIVE AND INFLAMMATORY CONDITIONS

This application is application is a National Stage application of PCT/US2005/016691, filed on 12 May 2005, as a PCT International Patent application in the name of The Government of the United States of America, as represented by the Secretary, Department of Health and Human Services, applicant for the designation of all countries except the U.S., and Jau-Shyong Hong, Liya Qin, Guorong Li, Michelle Block, Wei Zhang, Po-See Chen, and Giia-Sheun Peng, applicants for the designation of the U.S. only, and claims priority to U.S. Provisional App. No. 60/570,566, filed May 12, 2004, which is incorporated by reference herein.

This invention is supported by the Department of Health and Human Services. The Government of the United States of America may have certain rights in the invention disclosed and claimed herein below.

FIELD OF THE INVENTION

The invention relates to methods of affecting various biological mechanisms related to inflammation, the resultant inflammation and the disorders that may be caused thereby. More specifically, the invention relates to administration of compounds for neuroprotective and/or neurotrophic effects for treatment and/or prevention of neurodegenerative disorders and diseases caused thereby.

BACKGROUND OF THE INVENTION

Inflammation in the brain is characterized by the activation of microglia and astroglia, and is thought to be associated with the pathogenesis of a number of neurological diseases, including Parkinson's disease (PD), Alzheimer's disease and cerebral ischemia. Epidemiological studies have shown a positive correlation between PD and inflammation early in life. For example, the increase in the incidence of PD in 1945-50's was highly correlated to the flu pandemic in 1910-20's. It was also found that a higher PD incidence appeared among populations who were professional boxers at a young age.

It is thought that such primary insults and inflammation activate glial cells, specifically microglia. The activated microglia secrete various cytokines and free radicals, such as superoxide and nitric oxide (NO), resulting in cerebral inflammation and subsequent neuronal death and damage. Accumulation and/or overproduction of these factors impact neurons to induce their degeneration.

One specific inflammatory agent that is often implicated in inflammatory conditions is lipopolysaccharide (LPS). LPS can activate microglia and other cells to overproduce proinflammatory cytokines and free radicals, such as NO, $PGE_2$, $TNF\alpha$, superoxide, and other reactive oxygen species (ROS). Cerebral inflammation sustained by microglia activation triggered by LPS results in a delayed and progressive degeneration of nigra dopaminergic neurons. Dopaminergic neurons, in particular, can be especially vulnerable to oxidative damage due to antioxidant capacity It is also believed that decreased neurotrophic factor released from astroglia could play a role in susceptibility to inflammation. For example, glial cell line-derived neurotrophic factor (GDNF) is synthesized and released from astroglia. GDNF is believed to at least partly mediate neurotrophic effects on dopaminergic (DA) neurons.

Therefore, there remains a need for a greater understanding of the mechanisms involved in these disease states and inflammation. There is also a need for development of agents and treatments that activate neuronal-survival signaling pathways that may enhance the resilience and plasticity of brain cells.

SUMMARY OF THE INVENTION

The invention includes methods of providing neuroprotective and/or neurotrophic effects by contacting, administering, or treating a mammal with an effective amount of at least one compound of the invention comprising valproic acid, sodium valproate, butyric acid, sodium butyrate, or other salts thereof; opioid peptides; a peptide comprising Gly-Gly-Phe (GGF); or morphinans, such as naloxone, naltrexone, and dextromethorphan.

An embodiment of the invention provides methods for activating neuronal-survival signaling pathways in a mammal that comprise administration of at least one compound of the invention. The invention provides methods of inducing release of neurotrophic factors from astroglial cells by treating the cells with valproic acid, sodium valproate, butyric acid, sodium butyrate, or other salts thereof; and/or 3-hydroxymorphinan.

The invention also provides methods of inhibiting over activation of innate immune cells that comprise contacting an innate immune cell with a therapeutically effective amount of at least one compound of the invention. The inhibition of the over activation of microglia can occur either in vivo or in vitro.

The invention also includes methods of reducing inflammation in a mammal that comprise administration of at least one compound of the invention at an effective dosage.

The invention also includes methods of treating an inflammation-related condition in a mammal that comprises administration of at least one compound of the invention at an effective dosage to the mammal. The inflammation-related condition can include inflammation associated with diseases, such as Alzheimer's disease, Parkinson's disease, ALS, atherosclerosis, diabetes, arthritis, multiple sclerosis, sepsis, septic shock, endotoxemia, multiple organ failure, or organ damage, such as liver damage.

The invention further provides methods for neuroprotection comprising methods for reducing inflammation and methods for activating neuronal-survival signaling pathways.

The invention includes methods of inhibiting the activity of NADPH oxidase that comprise modulating or inhibiting the NADPH oxidase with an effective amount of at least one compound of the invention. The inhibition of the activity of NADPH oxidase can occur either in vivo or in vitro.

The invention also includes methods of inhibiting the activity of NADPH oxidase by affecting the gp91 subunit that comprise contacting the gp91 subunit with an effective amount of at least one compound of the invention. The inhibition of the activity of NADPH oxidase can occur either in vivo or in vitro.

The invention also includes methods of inhibiting the activity of NADPH oxidase; inhibiting the NADPH oxidase activity by affecting the gp91 subunit; inhibiting the over activation of innate immune cells; decreasing the release of one or more of $TNF\alpha$; $PGE_2$, IL-1, nitric oxide or superoxide; attenuating the toxin-induced death and/or damage of tissues; attenuating the toxin-induced deathand/or damage of dopaminergic neurons; reducing inflammation in a mammal; and treating an inflammation-related condition in a mammal that comprise contacting the particular enzyme, subunit, cell, tissue, or neuron; or administering to the mammal an effective amount of a peptide comprising the amino acid sequence GGF (SEQ ID NO:2).

The invention also includes methods of identifying compounds that may be therapeutically effective in treating an inflammation-related condition that comprise contacting NADPH oxidase with at least one candidate compound, and determining whether the candidate inhibits NADPH oxidase as compared to NADPH oxidase without the compound, wherein a compound may be therapeutically effective in treating an inflammation-associated condition if the compound decreases the expression or activity of NADPH oxidase or the gp91 subunit of NADPH oxidase.

The invention also includes methods of decreasing the release of one or more of tumor necrosis factor α (TNFα), prostaglandin $E_2$ ($PGE_2$), interleukin-1 (IL-1), nitric oxide, or superoxide that comprise administration of at least one compound of the invention at an effective dosage. The decrease in the release of one or more of tumor necrosis factor α (TNFα), prostaglandin $E_2$ ($PGE_2$), interleukin-1 (IL-1), nitric oxide, or superoxide can occur either in vivo or in vitro.

An embodiment of the invention provides a polypeptide or peptide comprising an amino acid sequence GGF that can be used in methods of the invention.

The invention also includes compositions that comprise ultra low concentrations of a compound of the invention.

DETAILED DESCRIPTION OF THE INVENTION

Figure 1:
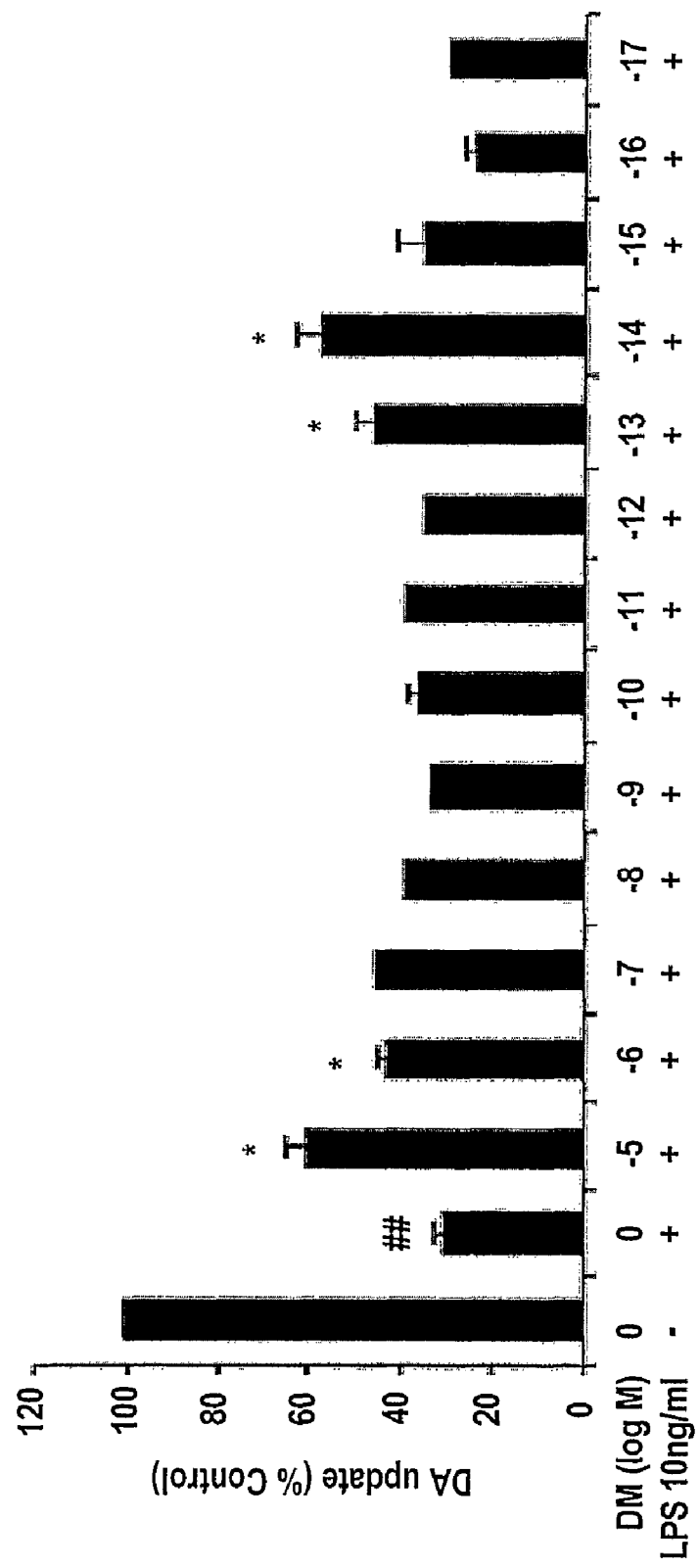
FIG. 1 is a graph depicting the dopamine (DA) uptake as a percentage of the control neuron-glia cells that were pretreated with various concentrations of dextromethorphan (DM) followed by lipopolysaccharide (LPS) treatment.

All scientific and technical terms used in this application have meanings commonly used in the art unless otherwise specified. As used in this application, the following words or phrases have the meanings specified.

As used herein, the term "about" applies to all numeric values, whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Methods of the invention that comprise steps of contacting a compound of the invention with an enzyme or other entity can be accomplished in a solution, or otherwise.

As used herein, "ultra low" amounts or concentrations refers to femtomolar concentrations (from about $10^{-13}$ M to about $10^{-15}$ M) of the compounds of the invention. Concentrations expressed in M generally correspond to a decrease of a dose of about 100 million fold when administered in vivo. Effective concentrations for use in methods of the invention, including ultra low concentrations, are also expressed as grams per kilogram body weight of the mammal being treated. In general 1 mg/kg corresponds to micromolar ($1\times10^{-6}$ M), and 10 pg/kg generally corresponds to femtomolar ($1\times10^{-15}$ M concentrations.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to treat inflammation associated disease or affect the various mechanisms associated therewith, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

1. Inhibition of Activity of NADPH Oxidase

The invention includes methods of inhibiting the activity of NADPH oxidase. As used herein, "inhibiting the activity of NADPH oxidase" refers to processes or methods that decrease the activity of NADPH oxidase either in vivo or in vitro, relative to NADPH oxidase either in vivo or in vitro, that has not been subjected to such a process or method. As used herein "inhibiting the activity of NADPH oxidase" additionally refers to processes or methods that reduce or prevent the over-activity of NADPH oxidase either in vivo or in vitro, relative to NADPH oxidase either in vivo or in vitro, that has not been subjected to such a process or method. "Over activity of NADPH oxidase" refers to activity of this enzyme that is more than that which is commonly seen in an untreated or control subject or cell, whether in vivo or in vitro.

A method of inhibiting the activity of NADPH oxidase comprises a step of contacting NADPH oxidase with an effective amount of at least one compound of the invention. In one embodiment of the invention, the step of contacting the NADPH oxidase with the at least one compound is accomplished in vivo. In another embodiment of the invention, the step of contacting the NADPH oxidase with the at least one compound is accomplished in vitro.

The invention also includes a method of inhibiting the activity of NADPH oxidase that comprises a step of inhibiting the NADPH oxidase with an effective amount of a peptide comprising GGF. In some embodiments, a polypeptide or peptide comprises an amino acid sequence GGF (Gly-Gly-Phe) and is other than or excludes the full length sequence of dynorphin A (SEQ ID NO:1). Preferably, the polypeptide can inhibit the activity of NADPH oxidase. In other embodiments, a peptide comprising GGF has no more than 16 amino acids, more preferably, about 3 to 16 amino acids, more preferably about 3 to 10 amino acids, and more preferably about 3 to 5 amino acids. In other embodiments, a peptide that comprises GGF may be chemically modified or linked to a heterologous polypeptide. In preferred embodiments, a peptide comprising GGF may be linked to a molecule or compound that enhances intracellular transport or transport across the blood brain barrier.

The effective amount of the compound is that amount that provides for inhibition of NADPH oxidase activity by at least 25%, more preferably at least 50%, and most preferably 100%, or to control levels. An inhibition NADPH oxidase activity can be determined by detecting a decrease in reactive oxygen species (ROS) either extracellularly or intracellularly or by other methods known to those of skill in the art. In some embodiments, the effect amount can be from about $10^{-5}$ M to about $10^{-15}$ M. In another embodiment of the invention, the effective amount of the compound is from about $10^{-5}$ M to about $10^{-7}$ M, or about $10^{-13}$ M to about $10^{-15}$ M.

In other embodiments, a compound inhibits the activity of NADPH oxidase if it decreases the activity of NADPH oxidase by at least about 30% when measured by the production of superoxide. In another embodiment of the invention, a compound inhibits the activity of NADPH oxidase if it decreases the activity of NADPH oxidase by at least about 50% when measured by the production of superoxide. In another embodiment of the invention, a compound inhibits the activity of NADPH oxidase if it decreases the activity of NADPH oxidase by at least about 70% when measured by the production of superoxide.

Over activity of NADPH can be caused by a variety of agents, including, but not limited to lippolysaccharide (LPS), β-amyloid peptides, 1-methyl-4-phenyl-1,2,3,6-tetrahydropyridine (MPTP), or environmental toxins. Examples of environmental toxins include, but are not limited to insecticides such as rotenone, pesticides, such as paraquat; and particulate mater (e.g. ubiquitous particulate components of an air pollution).

In other embodiments, other compounds can be utilized to inhibit NADPH oxidase activity. Preferably, the compounds are those that can penetrate the blood brain barrier and act on inflammation in the brain. The other compounds comprise naloxone, naltrexone, dextromethorphan, valproate, valproic acid or salts thereof, butyric acid or salts thereof, an opioid peptide such as Met enkephlin or Leu-enkephalin, or mixtures thereof.

In some embodiments, a compound that inhibits NADPH oxidase activity is administered at an "ultra low" concentration. In some embodiments, the concentration of the compound is at least $10^{-13}$ M, more preferably about $10^{-13}$ M to $10^{-15}$ M, more preferably about $10^{-14}$ M, and more preferably about $10^{-15}$ M. In an embodiment, ultra low concentrations comprise about 10 pg/kg to about 1000 pg/kg, more preferably about 1000 pg/kg, more preferably about 100 pg/kg, and more about preferably 10 pg/kg.

In other embodiments, the concentration of the compound in the µM amount is also effective to inhibit NADPH oxidase. In some embodiments, the compound is administered at about $10^{-5}$ to about $10^{-7}$ M, more preferably $10^{-5}$, more preferably $10^{-6}$ and more preferably about $10^{-7}$ M.

In an embodiment, the method comprises contacting NADPH oxidase with an effective amount of a morphinan or a peptide comprising an amino acid sequence GGF, wherein the effective amount is about $10^{-13}$ to about $10^{-15}$ M. Morphinans include without limitation, dextromethorphan, naloxone, and naltrexone. A peptide comprising an amino acid sequence GGF, preferably, has no more than sixteen amino acids and does not include the full length sequence of dynorphin A (SEQ ID NO:1). Examples of some peptides comprising GGF are shown in Table 1.

NADPH oxidase is a complex enzyme that contains 7 subunits, one of which is gp91. gp91 is the catalytic subunit of NADPH, and therefore may play a significant role in modulating the activity of NADPH.

The invention therefore also includes methods of inhibiting the activity of NADPH oxidase by affecting the gp91 subunit of NADPH oxidase. As used herein, "affecting the gp91 subunit of NADPH oxidase" refers to processes or methods that alter the configuration of one or more regions of the gp91 subunit either in vivo or in vitro, relative to a gp91 subunit either in vivo or in vitro, that has not been subjected to such a process or method; or processes or methods that block at least a portion of the gp91 subunit from binding with another protein or compound either in vivo or in vitro, relative to a gp91 subunit either in vivo or in vitro, that has not been subjected to such a process or method.

A method of affecting the gp91 subunit of NADPH oxidase comprises the step of contacting the gp91 subunit of NADPH oxidase with an effective amount of at least one compound of the invention. In one embodiment of the invention, the step of contacting the gp91 subunit of NADPH oxidase with the at least one compound is accomplished in vivo. In another embodiment of the invention, the step of contacting the gp91 subunit of NADPH oxidase with the at least one compound is accomplished in vitro.

The invention also includes methods of affecting the gp91 subunit of NADPH oxidase that comprises the step of contacting the gp91 subunit with an effective amount of a peptide comprising tripeptide GGF. In some embodiments, a polypeptide or peptide that comprises an amino acid sequence GGF (Gly-Gly-Phe) is other than or excludes the full length sequence of dynorphin A (SEQ ID NO:1). Preferably, the polypeptide can inhibit the activity of NADPH oxidase. In other embodiments, a peptide comprising GGF has no more than 16 amino acids, more preferably, about 3 to 16 amino acids, more preferably about 3 to 10 amino acids, and more preferably about 3 to 5 amino acids. In other embodiments, a peptide that comprises GGF may be chemically modified or linked to a heterologous polypeptide. In preferred embodiments, a peptide comprising GF may be linked to a molecule or compound that enhances intracellular transport or transport across the blood brain barrier. In one embodiment of the invention, the effective amount of the compound can be from about $10^{-5}$ M to about $10^{-15}$ M. In another embodiment of the invention, the effective amount of the compound is from about $10^{-5}$ M to about $10^{-7}$ M, or about $10^{-13}$ M to about $10^{-15}$ M.

NADPH controls the release of pro-inflammatory agents from the innate immune cells within a tissue system. Examples of innate immune cells within particular tissue systems include, but are not limited to microglia in neurological tissues, macrophages in organs, such as for example Kupffer cells in the liver, macrophages in the lungs, masengial cells in the kidney, and the endothelial cells lining the blood. The invention additionally includes methods of inhibiting microglial NADPH oxidase.

It is thought that preventing or reducing the amount of over-activity of NADPH oxidase can reduce the over-activation of the innate immune cells within a particular tissue system. The invention also includes methods of inhibiting activation of at least one innate immune cell within a tissue system. The invention further includes methods of inhibiting microglial activation. Another embodiment of the invention provides methods of inhibiting the activation or over-activation of at least one innate immune cell that comprise contacting the innate immune cell with an therapeutically effective amount of at least one compound of the invention. In one embodiment of the invention, the step of contacting the innate immune cell with the at least one compound is accomplished in vivo. In another embodiment of the invention, the step of contacting the innate immune cell with the at least one compound is accomplished in vitro.

An embodiment of the invention provides methods of inhibiting the activation or over-activation of at least one innate immune cell that comprise contacting the innate immune cell with an effective amount of a peptide or polypeptide comprising tripeptide GGF. In some embodiments, a polypeptide or peptide comprises an amino acid sequence GGF (Gly-Gly-Phe) and is other than or excludes the full length sequence of dynorphin A (SEQ ID NO:1). Preferably, the polypeptide can inhibit the activity of NADPH oxidase and/or the production of reactive oxygen species. In other embodiments, a peptide comprising GGF has no more than 16 amino acids, more preferably, about 3 to 16 amino acids, more preferably about 3 to 10 amino acids, and more preferably about 3 to 5 amino acids. In other embodiments, a peptide that comprises GGF may be chemically modified or linked to a heterologous polypeptide. In preferred embodiments, a peptide comprising GGF may be linked to a molecule or compound that enhances intracellular transport or transport across the blood brain barrier. In one embodiment of the invention, the effective amount of the compound can be from about $10^{-5}$ M to about $10^{-15}$ M. In another embodiment of the invention, the effective amount of the compound is from about $10^{-5}$ M to about $10^{-7}$ M, or ultra low concentrations of about $10^{-13}$ M to about $10^{-15}$ M. In an embodiment, ultra low concentrations comprise about 10 pg/kg to about 1000 pg/kg, more preferably about 1000 pg/kg, more preferably about 100 pg/kg, and more about preferably 10 pg/kg.

Yet another embodiment of the invention provides methods of inhibiting the activation or over-activation of at least one microglial cell that comprises contacting the microglial with an effective amount of at least one compound of the invention. In one embodiment of the invention, the step of contacting the microglial with the at least one compound is accomplished in vivo. In another embodiment of the invention, the step of contacting the microglial with the at least one compound is accomplished in vitro.

In other embodiments, other compounds can be utilized to inhibit activation of innate immune cells. Preferably, the compounds are those that can penetrate the blood brain barrier and act on inflammation in the brain. The other compounds comprise naloxone, naltrexone, dextromethorphan, valproate, valproic acid or salts thereof, butyric acid or salts thereof, an opioid peptide such as Met enkephalin or Leu-enkephalin, or mixtures thereof.

An embodiment of the invention provides methods of inhibiting activation of at least one innate immune cell, comprising contacting the cell with an effective amount of a compound of the invention. In an embodiment, the method of inhibiting activation decreases the activity of the at least one innate immune cell by at least about 30%. In an embodiment, the method of inhibiting activation decreases the activity of the at least one innate immune cell by at least about 50%. In an embodiment, the method of inhibiting activation decreases the activity of the at least one innate immune cell by at least about 70%.

The invention also includes methods of inhibiting the activation or over-activation of at least one microglial cell that comprises contacting the microglial with an effective amount of tripeptide GGF. In one embodiment of the invention, the effective amount of the compound can be from about $10^{-5}$ M to about $10^{-15}$ M. In another embodiment of the invention, the effective amount of the compound is from about $10^{-5}$ M to about $10^{-7}$ M, or about $10^{-13}$ M to about $10^{-15}$ M.

As used herein, the phrase "inhibiting microglial activation" refers to processes or methods that deactivate previously activated microglia either in vivo or in vitro, relative to microglia either in vivo or in vitro, that have not been subjected to such a process or method; processes or methods that slow the activation of microglia either in vivo or in vitro, relative to microglia either in vivo or in vitro, that have not been subjected to such a process or method; processes or methods that limit the number of microglia that are activated, either in vivo or in vitro, relative to microglia either in vivo or in vitro, that have not been subjected to such a process or method; or processes or methods that lessen the level of activation of activated microglia either in vivo or in vitro, relative to microglia either in vivo or in vitro, that have not been subjected to such a process or method.

The activation of innate immune cells, such as microglia or Kupffer cells involves the release of a number of soluble pro-inflammatory factors, including, but not limited to tumor necrosis factor alpha (TNFα), prostaglandin $E_2$ ($PGE_2$), interleukin-1 (IL-1), and free radicals such as nitric oxide and superoxide.

A compound may be determined to have an ability to "inhibit NADPH activity", "affect the gp91 subunit", or "inhibit activation of innate immune cells" by measuring and/or monitoring at least one of the following: tumor necrosis factor alpha (TNFα), prostaglandin $E_2$ ($_{PGE2}$), interleukin-1 (IL-1), free radicals such as nitric oxide (NO) and superoxide ($O_2^-$), and the immunostaining intensity of OX-42 immunoreactivity, which is a marker for the activation of microglia.

In another embodiment, the invention also includes methods of decreasing the release of one or more of TNFα, $PGE_2$, IL-1, NO and $O_2^-$ from innate immune cells, such as microglia.

TNFα

One example of a method of measuring and/or monitoring the amount of TNFα in tissues and or serum includes a TNFα enzyme-linked immunosorbent assay (ELISA) kit. An example of one such kit is TNFα-ELISA kit, which is commercially available from R&D Systems, Minneapolis Minn. One of skill in the art, having read this specification would understand and realize what other methods could be used to monitor the amount of TNFα in tissue, serum, or some combination thereof. The invention also envisions and encompasses use of such other methods to monitor and/or measure the amount of TNFα in samples.

$PGE_2$

One example of a method of measuring and/or monitoring the amount of $PGE_2$ in tissues and or serum includes prostaglandin $E_2$ enzyme immunoassay (EIA) kit. An example of one such kit is $PGE_2$-ELISA kit, which is commercially available from Cyaman, Ann Arbor, Mich. One of skill in the art, having read this specification would understand and realize what other methods could be used to monitor the amount of $PGE_2$ in tissue, serum, or some combination thereof. The invention also envisions and encompasses use of such other methods to monitor and/or measure the amount of $PGE_2$ in samples.

IL-1

One example of a method of measuring and/or monitoring the amount of IL-1 in tissues and or serum includes an IL-1 enzyme-linked immunosorbent assay (ELISA) kit. An example of one such kit is IL-1 ELISA kit, which is commercially available from R&D Systems, Minneapolis Minn. One of skill in the art, having read this specification would understand and realize what other methods could be used to monitor the amount of IL-1 in tissue, serum, or some combination thereof. The invention also envisions and encompasses use of such other methods to monitor and/or measure the amount of IL-1 in samples.

Nitric Oxide

One example of a method of measuring and/or monitoring the amount of nitrite (which relates to nitric oxide) in tissues and or serum includes measuring the accumulated levels of nitrite in the supernatant with the Griess reagent. (Green et al., 1982) Griess reagent kits are available commercially, for example from Promega Corporation, Madison, Wis. One of skill in the art, having read this specification would understand and realize what other methods could be used to monitor the amount of nitric oxide and/or nitrite in tissue, serum, or some combination thereof. The invention also envisions and encompasses use of such other methods to monitor and/or measure the amount of nitric oxide and/or nitrite in samples.

Superoxide Production

A compound may be determined to have an ability to "affect the gp91 subunit" or "inhibit the activity of NADPH oxidase" by monitoring the amount of superoxide in tissues or serum. One example of a method of measuring and/or monitoring the amount of superoxide ($O_2^-$) in tissues and or serum includes a method of measuring the superoxide dismutase (SOD) inhibitable reduction of tetrazolium salt, WST-1.

One example of a specific method to measure the immediate release of superoxide from microglia-enriched or neuron-glia after stimulation, is to grow cultures in for example, a 96-well plate in a 10% maintenance medium, and switch them to phenol red-free HBSS (50 µl/well). To each well 50 µl of HBSS containing the compound whose effect is to be determined is added. The cultures can then be incubated at about 37° C. for about 30 min followed by the addition of about 50 µ of ferricytochrome c (100 µM) in HBSS, with and without 600 U/ml superoxide dismutase (SOD), 50 µl of vehicle or lipopolysacchride (LPS) in HBSS. The absorbance at 550 nm can then be read with a microplate spectrophotometer, such as a SpectraMax Plus device available commercially from Molecular Devices in Sunnyvale, Calif. One of skill in the art will also understand that other similar methods and variants of this method can also be used to measure the superoxide production.

One of skill in the art, having read this specification would understand and realize that other methods could be used to monitor the amount of superoxide in tissue, serum, or some combination thereof. The invention also envisions and encompasses use of such other methods to monitor and/or measure the amount of superoxide in samples.

In one embodiment of a method of the invention, the tissues that can be monitored for the various pro-inflammatory factors mentioned herein (as well as others that have the same indications, as would be known to one of skill in the art having read this specification) include, but are not limited to brain, and liver tissues. In another embodiment of the invention, serum levels can be monitored for the various components mentioned herein (as well as others that have the same indications, as would be known to one of skill in the art having read this specification).

In one embodiment of the invention, a compound inhibits NADPH activity, affects the gp91 subunit, inhibits overactivation or activation of innate immune cells such as microglia if it decreases the release of one or more of TNFα, $PGE_2$, IL-1, NO, or $O_2^-$ by at least about 30% when measured using a method known to those of skill in the art having read this specification. In one embodiment of the invention, a compound inhibits NADPH activity, affects the gp91 subunit, inhibits overactivation or activation of innate immune cells such as microglia if it decreases the release of one or more of TNFα, PGE2, IL-1, $NO_2$, or $O_2^-$ by at least about 50% when measured using a method known to those of skill in the art having read this specification. In one embodiment of the invention, a compound inhibits NADPH activity, affects the gp91 subunit, inhibits overactivation or activation of innate immune cells such as microglia if it decreases the release of one or more of TNFα, $PGE_2$, IL-1, NO, or $O_2^-$ by at least about 70% when measured using a method known to those of skill in the art having read this specification.

2. Methods of Inhibiting Toxin-Induced Death or Damage of Dopaminergic Neurons

The invention also includes methods of attenuating or inhibiting toxin-induced death and/or damage of cells, such as neurons, liver cells, lung cells, and kidney cells. Examples of toxins that can induce dopaminergic neuron death and/or damage include, but are not limited to LPS, Aβ peptides (amyloid peptides), and environmental toxins.

LPS is an endotoxin from the outer membrane of the majority of the gram-negative bacteria, and may have implications in sepsis, organ failure and shock. LPS can induce septic shock in laboratory animals. Kupffer cells, resident macrophages in the liver, remove bacteria and their related endotoxins from the body when activated. In turn, the activated Kupffer cells release active substances, such as free radicals, and inflammatory cytokines. Examples of such free radicals and inflammatory cytokines include, but are not limited to tumor necrosis factor alpha (TNFα), prostaglandin $E_2$ ($PGE_2$), interleukin-1 (IL-1), and free radicals such as nitric oxide and superoxide. Reduction of such free radicals and inflammatory cytokines may therefore assist in decreasing the likelihood, occurrence, or severity of endotoxemia, septic shock, and multiple organ failure.

As used herein, the phrase attenuating toxin-induced death and/or damage of cells, such as neurons, refers to processes or methods that lessen the number of cells that die and/or are damaged as a result of one or more toxins either in vivo or in vitro, relative to cells either in vivo or in vitro, that have not been subjected to such a process or method; or processes or methods that lessen the severity of the effects of one or more toxins on the cells either in vivo or in vitro, relative to cells either in vivo or in vitro, that have not been subjected to such a process or method.

In one embodiment of the invention, a compound attenuates toxin-induced death and/or damage of cells if it decreases the percentage of cells that die and/or are damaged as a result of the toxin, relative to tissues not treated with the compound by a statistically significant amount. In another embodiment of the invention, a compound attenuates toxin-induced death and/or damage of cells if it decreases the percentage of cells that die as a result of the toxin, relative to cells not treated with the compound by at least about 30%. In yet another embodiment of the invention, a compound attenuates toxin-induced death of cells if it decreases the percentage of cells that die as a result of the toxin, relative to cells not treated with the compound by at least about 50%. In yet another embodiment of the invention, a compound attenuates toxin-induced death of cells if it decreases the percentage of cells that die as a result of the toxin, relative to cells not treated with the compound by at least about 70%.

Methods of attenuating or inhibiting toxin-induced death and/or damage of cells comprise the step of contacting at least one cell with an effective amount of at least one compound of the invention. In a further embodiment, the method comprises contacting at least one immune or inflammatory cell with an effective amount of at least one compound of the invention. In one embodiment of the invention, the step of contacting the at least one immune cell with the at least one compound is accomplished in vivo. In another embodiment of the invention, the step of contacting the at least one immune cell with the at least one compound is accomplished in vitro.

The invention also includes methods of attenuating toxin-induced death of innate immune cells that comprise the step of contacting at least one innate immune cell with an effective amount of a peptide comprising an amino acid sequence tripeptide GGF. In some embodiments, a polypeptide or peptide comprises an amino acid sequence GGF (Gly-Gly-Phe) and is other than or excludes the full length sequence of dynorphin A (SEQ ID NO:1). Preferably, the polypeptide can inhibit the activity of NADPH oxidase. In other embodiments, a peptide comprising GGF has no more than 16 amino acids, more preferably, about 3 to 16 amino acids, more preferably about 3 to 10 amino acids, and more preferably about 3 to 5 amino acids. In other embodiments, a peptide that comprises GGF may be chemically modified or linked to a heterologous polypeptide. In preferred embodiments, a peptide comprising GGF may be linked to a molecule or compound that enhances intracellular transport or transport across the blood brain barrier.

In one embodiment of the invention, the effective amount of the compound can be from about $10^{-5}$ M to about $10^{-15}$ M. In another embodiment of the invention, the effective amount of the compound is from about $10^{-5}$ to about $10^{-7}$, or about $10^{-13}$ to about $10^{-15}$ M. In some embodiments, the effective amount of the compound is at least about 10 pg/kg. In additional embodiments, the effective amount of the compound is at least about 100 pg/kg to about 10 mg/kg. In a further embodiment, the effective amount is at least about 100 pg/kg to about 1 µg/kg. In another embodiment the effective amount is from about 1 µg/kg to about 10 mg/kg. In a still further embodiment, the effective amount is from about 5 mg/kg, more preferably about 6 mg/kg to about 25 mg/kg.

In other embodiments, other compounds can be utilized to inhibit or attenuate toxin induced death and/or damage of cells. Reduction of reactive oxygen species and/or clearance of TNF-α are factors in protecting cells and tissues from toxin associated damage. Compounds that inhibit production and/or activity of these mediators are useful to treat or inhibit toxin induced death or damage of cells. Such compounds comprise naloxone, naltrexone, dextromethorphan, valproate, valproic acid or salts thereof, butyric acid or salts thereof, an opioid peptide such as Met enkephalin or Leu-enkephalin, or mixtures thereof.

3. Reduction of Inflammation

The invention also includes methods of reducing inflammation that comprise administering an effective amount of at least one of the compounds of the invention to a mammal.

The invention also includes methods of reducing inflammation that comprise administering to a mammal or human subject in need thereof an effective amount of a peptide comprising an amino acid sequence GGF. In some embodiments, a polypeptide or peptide comprises an amino acid sequence GGF (Gly-Gly-Phe) and is other than or excludes the full length sequence of dynorphin A (SEQ ID NO:1). Preferably, the polypeptide can inhibit the activity of NADPH oxidase. In other embodiments, a peptide comprising GGF has no more than 16 amino acids, more preferably, about 3 to 16 amino acids, more preferably about 3 to 10 amino acids, and more preferably about 3 to 5 amino acids. In other embodiments, a peptide that comprises GGF may be chemically modified or linked to a heterologous polypeptide. In preferred embodiments, a peptide comprising GGF may be linked to a molecule or compound that enhances intracellular transport or transport across the blood brain barrier.

In one embodiment of the invention, the effective amount of the compound can be from about $10^{-5}$ M to about $10^{-15}$ M. In another embodiment of the invention, the effective amount of the compound is from about $10^{-5}$ M to about $10^{-7}$ M, or about $10^{-13}$ M to about $10^{-15}$ M.

In some embodiments, the method of reducing inflammation comprises administering an effective amount at least one morphinan to a mammal or human subject in need thereof. Morphinans include, without limitation, dextromethorphan, naloxone, and naltrexone. In further embodiments, the effective amount is an ultra low concentration. Examples of ultra low concentration comprise about $10^{-13}$ to $10^{-15}$ M, more preferably $10^{-13}$ M, more preferably $10^{-14}$ M, and more preferably $10^{-15}$ M. In an embodiment, ultra low concentrations comprise about 10 pg/kg to about 1000 pg/kg, more preferably about 1000 pg/kg, more preferably about 100 pg/kg, and more about preferably 10 pg/kg.

In some embodiments, the method of reducing inflammation comprises administering an effective amount of valproate, valproic acid, butyric acid, sodium valproate, sodium butyrate or other salts thereof, to a mammal or human subject in need thereof. In further embodiments, the effective amount is an ultra low concentration. Examples of ultra low concentration comprise about $10^{-13}$ to $10^{-15}$ M, more preferably $10^{-13}$ M, more preferably $10^{-14}$ M, and more preferably $10^{-15}$ M. In an embodiment, ultra low concentrations comprise about 10 pg/kg to about 1000 pg/kg, more preferably about 1000 pg/kg, more preferably about 100 pg/kg, and more about preferably 10 pg/kg.

In some embodiments, the method of reducing inflammation comprises administering to a mammal or human subject in need thereof at least one opioid peptide. Opioid peptides, include, without limitation, leu enkephalin and/or met enkephalin. In further embodiments, the effective amount is an ultra low concentration. Examples of ultra low concentration comprise about $10^{-13}$ to $10^{-15}$ M, more preferably $10^{-13}$ M, more preferably $10^{-14}$ M, and more preferably $10^{-15}$ M. In an embodiment, ultra low concentrations comprise about 10 pg/kg to about 1000 pg/kg, more preferably about 1000 pg/kg, more preferably about 100 pg/kg, and more about preferably 10 pg/kg.

In some embodiments, a method of reducing inflammation comprises administering to a mammal or human subject in need thereof a peptide comprising an amino acid sequence GGF. Peptides comprising GGF, preferably do not include the full length sequence of dynorphin A (SEQ ID NO:1). Examples of some peptide comprising GGF are shown in Table 1. In some embodiments, peptides comprise no more than 16 amino acids, preferably about 3 to 16 amino acids, more preferably about 3 to 10 amino acids, and more preferably about 3-5 amino acids. In some embodiments, a peptide comprising GGF, further comprises another compound or a heterologous polypeptide. In further embodiments, the effective amount is an ultra low concentration. Examples of ultra low concentration comprise about $10^{-13}$ to $10^{-15}$ M, more preferably $10^{-13}$ M, more preferably $10^{-14}$ M, and more preferably $10^{-15}$ M. In an embodiment, ultra low concentrations comprise about 10 pg/kg to about 1000 pg/kg, more preferably about 1000 pg/kg, more preferably about 100 pg/kg, and more about preferably 10 pg/kg.

An inflammatory condition can exist as a result of many factors. In some embodiments, the inflammatory condition is associated or related to disease or disorder including Alzheimer's disease, Parkinson's disease, ALS, MS, atherosclerosis, diabetes, arthritis, sepsis, septic shock, endotoxemia, multiple organ failure or organ damage.

As used herein, the phrase "reduce inflammation" includes lessening at least one physiological effect of inflammation, lessening at least one symptom associated with inflammation, or some combination thereof.

In one embodiment of the invention, the inflammation to be reduced may be associated with an inflammation-related condition, as that term is utilized below. The inflammation may be a precursor of, a causative effect of, or a symptom of the inflammation-related condition. In another embodiment of the invention, the cause of the inflammation to be reduced may be unknown, and its relation to an inflammation-related condition also unknown.

A compound may be determined to have reduced inflammation by monitoring the symptoms of a patient exhibiting inflammation in one or more tissues or organs. In one embodiment of the invention, a compound has reduced inflammation if the physiological indications of inflammation are reduced or the symptoms are lessened.

4. Neurotrophic Activity

In an embodiment, the invention includes methods of inducing release of neurotrophic factors that exhibit neurotrophic effects on neurons. In a further embodiment, the neurotrophic effects are on dopaminergic neurons. The invention further includes methods for mediating release of neurotrophic factors from astroglia.

An embodiment of the invention provides methods for activating neuronal-survival signaling pathways in a mammal or human subject in need thereof that comprise administration of at least one compound of the invention. In a further embodiment, the compound is valproic acid (VPA) or salts thereof or valproate. In additional embodiment, the compound comprises butyric acid and salts thereof. In other embodiment, the compound comprises 3-hydroxy-morphinan.

In an embodiment, the invention includes any of the methods for neuroprotection comprising methods for reducing inflammation described above in combination with methods for activating neuronal-survival signaling pathways.

In an embodiment, one or more compounds of the invention exhibit both neurotrophic and neuroprotective activities. In a further embodiment, the compound is valproic acid.

In an embodiment, the invention includes methods for induction of release of glial cell-line-derived neurotrophic factor (GDNF). GDNF is several orders of magnitude more potent than other neurotrophins. A further embodiment provides methods for induction of GDNF to promote survival and protection of nerve cells. A still further embodiment provides methods including administration of at least one compound of the invention to induce release of GDNF. In a further embodiment, the compound is valproic acid (VPA) or valproate.

In an embodiment, a method comprises administering an effective amount of an inhibitor of histone deacetylase to a cell or tissue that is capable of producing glial-derived neurotrophic factor. In some embodiments, the tissue is nerve tissue comprising astroglial cells. In other embodiments, the inhibitor of histone deacetylase comprises valproic acid, butyric acid and/or salts thereof. In some embodiments, an effective amount is about 0.1 to about 1 µM, more preferably about 0.2 to about 0.8 µM, more preferably about 0.4 to about 0.6 µM.

In another embodiment, a method of providing a neurotrophic effect comprises administering to a cell or tissue an effective amount of 3-hydroxymorphinan. In some embodiments, the tissue or cells comprise astroglia cells. In some embodiments, an effective amount comprises about 1 to 10 µM, more preferably about 1 to about 5 µM, and more preferably about 2.5 to 5 µM.

5. Treatment of Disorders or Conditions

One aspect of the invention includes methods of treating inflammation in the brain characterized by activation of microglia and astroglia. Another aspect of the invention includes methods of treating Parkinson's disease, Alzheimer's disease, ALS, MS, atherosclerosis, diabetes, arthritis, sepsis, septic shock, endotoxemia, multiple organ failure, or organ damage.

The invention also includes methods of treating an inflammation-related or other neurological condition that comprises administering an effective amount of a peptide comprising an amino acid sequence GGF. In some embodiments, a polypeptide or peptide comprises an amino acid sequence GGF (Gly-Gly-Phe) and is other than or excludes the full length sequence of dynorphin A (SEQ ID NO:1). Preferably, the polypeptide can inhibit the activity of NADPH oxidase and/or the generation of reactive oxygen species. In other embodiments, a peptide comprising GGF has no more than 16 amino acids, more preferably, about 3 to 16 amino acids, more preferably about 3 to 10 amino acids, and more preferably about 3 to 5 amino acids. In other embodiments, a peptide that comprises GGF may be chemically modified or linked to a heterologous polypeptide. In preferred embodiments, a peptide comprising GGF may be linked to a molecule or compound that enhances intracellular transport or transport across the blood brain barrier.

In one embodiment of the invention, the effective amount of the compound can be from about $10^{-5}$ M to about $10^{-15}$ M. In another embodiment of the invention, the effective amount of the compound is from about $10^{-5}$ M to about $10^{-7}$ M, or about $10^{-13}$ M to about $10^{-15}$ M.

The invention also includes methods of treating an inflammation-related or other neurological condition that comprises administering an effective amount of valproic acid (VPA), valproate, butyric acid, or other salts thereof. Valproic acid is a short chain fatty acid, previously used for treatment of bipolar disorders and seizures. In an embodiment, the therapeutically effective amount of valproic acid is from about $10^{-3}$ to about $10^{-6}$ M. In an embodiment of the invention, the effective amount of valproic acid or salts thereof (e.g., valproate) is from about 0.35 to 1 mM.

In other embodiments, other compounds can be utilized to treat inflammation associated conditions and/or other neurological conditions such as Alzheimers, Parkinsons, multiple sclerosis, and ALS. Preferably, the compounds are those that can penetrate the blood brain barrier and act on inflammation in the brain. The other compounds comprise naloxone, naltrexone, dextromethorphan, an opioid peptide such as Met enkephalin or Leu-enkephalin, or mixtures thereof. In some embodiments the compounds can be administered in an ultra low concentration, so as to achieve a concentration of about $10^{-13}$ M to about $10^{-15}$ M. In an embodiment, ultra low concentrations comprise about 10 pg/kg to about 1000 pg/kg, more preferably about 1000 pg/kg, more preferably about 100 pg/kg, and more about preferably 10 pg/kg.

As used herein, the word "treating" includes, but is not limited to, alleviating or relieving symptoms associated with the disease; inhibiting the progression of the disease, i.e., arresting its development; lessening the likelihood of the occurrence of the disease; reversing or limiting or lessening the deleterious effects of the disease on the diseased and related tissue.

As used herein, the phrase "inflammation-related condition" includes any disease, disorder, or condition that is caused by or related to an inflammatory process within one or more tissue or serum of the body of a mammal. In another embodiment, an "inflammation-related condition" includes inflammation-related diseases that are caused by or related to an inflammatory process within neurological tissue. Examples of inflammation-related condition that are caused by or related to an inflammatory process within neurological tissue include, but are not limited to Alzheimer's disease, Parkinson's disease, amytrophic lateral sclerosis (ALS), and multiple sclerosis (MS). Examples of inflammation-related condition that are caused by or related to an inflammatory process within tissues other than neurological tissues include, but are not limited to atherosclerosis, diabetes, arthritis, sepsis, septic shock, endotoxemia, multiple organ failure, cardiovascular disease, and organ damage, such as liver damage for example.

Included in the invention are methods of treating Alzheimer's disease, Parkinson's disease, ALS, MS, atherosclerosis, diabetes, arthritis, sepsis, septic shock, endotoxemia, multiple organ failure, and organ damage that comprise administering an ultra-low dose of at least one of the compounds of the invention to a mammal.

The mammal to be treated may be already diagnosed with the inflammation-related condition, may be at risk of developing the inflammation-related condition, may have experienced a trauma that may increase the chances of the inflammation-related condition occurring, or may have no heightened risk of developing the inflammation-related condition.

6. Methods of Identifying Therapeutic Targets

The invention also includes methods of identifying compounds that may be effective in treating an inflammation-related condition that comprise contacting NADPH oxidase or a solution containing the gp91 subunit of NADPH oxidase with a candidate compound, and determining whether the candidate compound inhibits NADPH oxidase as compared to NADPH oxidase in the absence of the compound, wherein a compound may be therapeutically effective in treating an inflammation-related condition if the compound decreases the activity of the NADPH oxidase or its gp91 subunit.

The invention also includes methods of identifying compounds that may be effective in treating an inflammation-related condition that comprise monitoring the behavior of the gp91 subunit NADPH oxidase and/or contacting the NADPH oxidase or a solution containing NADPH oxidase with a compound, monitoring the effect of the compound on the activity of the gp91 subunit NADPH oxidase, and comparing that effect with the activity gp91 subunit of the NADPH oxidase without the compound, wherein a compound may be therapeutically effective in treating an inflammation-related condition if the compound decreases the activity of the gp91 subunit NADPH oxidase.

The invention also includes methods of identifying compounds that may be effective in treating an inflammation-related condition that comprise contacting the innate immune cell with a compound, and comparing that effect in the presence of the compound with the activity, or overactivity of an innate immune cell without the compound, wherein a compound may be therapeutically effective in treating an inflammation-related condition if the compound decreases the activity, or overactivity of the innate immune cell.

The monitoring steps referred to in the methods of identifying targets can be accomplished by monitoring one or more of the pro-inflammatory factors discussed above.

7. Compounds of the Invention

It has previously been shown that dynorphin A (DYNA (1-17) Tyr-Gly-Gly-Phe-Leu-Arg-Arg-Ile-Arg-Pro-Lys-Leu-Lys-Trp-Asp-Asn-Gln (SEQ ID NO:1) a kappa receptor agonist, protects mesencephalic dopaminergic neurons from microglia-mediated neurotoxicity.

It was unexpectedly discovered that the minimal, and novel fragment glycine-glycine-phenylalanine (GGF) (SEQ ID NO. 2), can be used to effectuate methods of the invention. The observation that this particular peptide fragment could be utilized was surprising because as seen above, it does not need the initial amino acid of dynorphin A, which was commonly thought necessary for binding to the active site of the Kappa receptor. In one aspect of the invention, a peptide comprises, or consists of an amino acid sequence GGF. In some embodiments, a polypeptide or peptide comprises an amino acid sequence GGF (Gly-Gly-Phe) and is other than or excludes the full length sequence of dynorphin A (SEQ ID NO:1). Examples of such peptides are provided in Table 1. Preferably, the polypeptide can inhibit the activity of NADPH oxidase and/or the generation of reactive oxygen species. In other embodiments, a peptide comprising GGF has no more than 16 amino acids, more preferably, about 3 to 16 amino acids, more preferably about 3 to 10 amino acids, and more preferably about 3 to 5 amino acids. In other embodiments, a peptide that comprises GGF may be chemically modified or linked to a heterologous polypeptide. In preferred embodiments, a peptide that comprises GGF may be linked to a molecule or compound that enhances intracellular transport or transport across the blood brain barrier.

Other compounds that can be used in the invention include morphinans. Exemplary morphinans include, but are not limited to naloxone, naltrexone, dextromethorphan. Opioid peptides including {Met 5}-enkephalin, and {Leu 5}-enkephalin can also be used in the invention. In one embodiment of the invention, either naloxone or dextromethorphan are used in methods of the invention.

Naloxone is commonly known as Narcan, and refers to the chemical compound: (5α)-4,5-Epoxy-3,14-dihydroxy-17-(2-propenyl)morphinan-6-one, or 17-allyl-4,5α-epoxy-3,14-dihydroxymorphinan-6-one. The structure of which is given below.

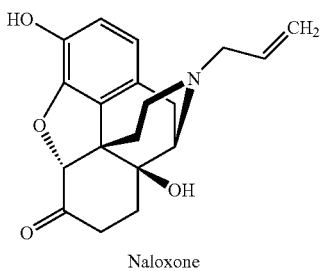

Naloxone

Dextromethorphan (DM), which refers to the compound, d-3-methoxy-N-methylmorphinan, is commonly used as an antitussive, and is commercially available in Robitussin® and Sucrets®. The structure of dextromethorphan is given below.

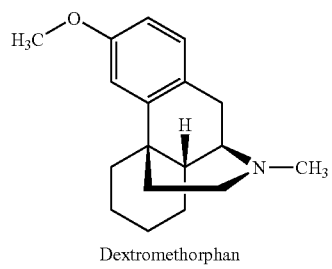

Dextromethorphan

In various embodiments, methods of the invention utilize ultra low amounts, dosages, or concentrations of one or more compounds of the invention. As used herein, the phrase "ultra low" refers to concentrations between and inclusive of about $10^{-13}$ M to $10^{-15}$ molar or moles/liter ("M"). In one embodiment, compounds of the invention are utilized in concentrations between and inclusive of about $10^{-13}$ M to $10^{-14}$ M. In another embodiment of the invention, compounds of the invention are utilized in concentrations between and inclusive of about $10^{-14}$ M. In an embodiment, ultra low concentrations comprise about 10 pg/kg to about 1000 pg/kg, more preferably about 1000 pg/kg, more preferably about 100 pg/kg, and more about preferably 10 pg/kg.

The novel tripeptide fragment, GGF and peptides comprising GGF, has at least two ranges at which it is "effective" in methods of the invention. GGF can be used at concentrations of about $10^{-5}$ to about $10^{-7}$ M, or about $10^{-13}$ to about $10^{-16}$ M.

Valproic acid (VPA), a simple eight-carbon branched-chain fatty acid. VPA is available either as the free acid, or in a salt form. One salt form of VPA is sodium valproate. Butyric acid is a four-carbon fatty acid. Butyric acid is available as a free acid, or in a salt form, for example Sodium Butyrate. Valproic acid, sodium butyrate and related compounds are effective in neurotrophic methods of the invention at concentrations from about 0.35 to 1 mM.

Compounds of the invention can be prepared by any method known to those of skill in the art, having read this specification. Furthermore, compounds of the invention are commercially available through a number of different sources. For example, the tripeptide, GGF, can be obtained from BACHEM, (Torrance Calif.).

Valproic acid is available from Sigma-Aldrich (St. Louis, Mo.).

Salts

Some of the compounds of the invention may be capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as, for example, silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms can be regenerated by treating the salt form with a base. For example, dilute solutions of aqueous base can be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

One example of a pharmaceutically acceptable salt includes a hydrochloride salt of a compound of the invention.

8. Compositions and Administration Methods

The compounds of the present invention can be formulated as pharmaceutical compositions and administered to a mammalian host, including a human patient, in a variety of forms adapted to the chosen route of administration.

The compounds are preferably administered in combination with a pharmaceutically acceptable carrier, and can be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents, and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons, or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Solutions or suspensions of the compounds can be prepared in water, isotonic saline (PBS), and optionally mixed with a nontoxic surfactant. Dispersions can also be prepared in glycerol, liquid polyethylene, glycols, DNA, vegetable oils, triacetin and mixtures thereof. Under ordinary conditions of storage and use, these preparations can contain a preservative to prevent the growth of microorganisms.

The pharmaceutical dosage form suitable for injection or infusion use can include sterile, aqueous solutions, dispersions, or sterile powders comprising an active ingredient which are adapted for the extemporaneous preparation of sterile injectable or infusible solutions or dispersions. The final dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols, and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption such as, for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

The dose of the compound to be administered can depend at least in part upon the patient, the patient's medical history, and the severity of the disease or disorder. Dosages for adult humans may range from between about 10 pg/kg to 1 mg/kg. In another embodiment of the invention, the dosage for an adult human may range from about 10 pg/kg to about 1 mg/kg. These doses may be repeated up to several times per day. In addition, lower and higher doses may be more appropriate depending on the individual patient and the disease or condition to be treated.

WORKING EXAMPLES

The following examples provide nonlimiting illustrations of various embodiments of the invention.

Cell culture ingredients were obtained from Invitrogen (Carlsbad, Calif.). [$^3$H]Dopamine (DA, 30 Ci/mmol) was purchased from PerkinElmer Life Sciences (Boston, Mass.). The monoclonal antibody against the CR3 complement receptor (OX-42) was obtained from BD PharMingen (San Diego, Calif.). The polyclonal anti-tyrosine hydroxylase (TH) antibody was a generous gift from Dr. John Reinhard (GlaxoSmithKline, Research Triangle Park, N.C.) (The antibody is also commercially available.). The monoclonal antibody against the CR3 complement receptor (OX-42) was obtained from BD PharMingen (San Diego, Calif.). The Vectastain ABC kit and biotinylated secondary antibodies were purchased from Vector Laboratories (Burlingame, Calif.). The CyQUANT cell proliferation assay kit was purchased from Molecular Probes, Inc. (Eugene, Oreg.). Griess Reagent is available from Promega Corporation (Madison, Wis.).

NADPH oxidase-deficient (gp91phox$^{-/-}$) and wild-type C57BL/6J (gp91phox$^{+/+}$) mice were obtained from The Jackson Laboratory (Bar Harbor, Me.). Breeding of the mice was performed to achieve timed pregnancy with the accuracy of ±0.5 d. Timed-pregnant Fisher F344 rats were obtained from Charles River Laboratories (Raleigh, N.C.). Housing and breeding of the animals were performed in strict accordance with the National Institutes of Health guidelines.

Data are presented as the mean ±S.E.M. for multiple comparisons of groups using ANOVA. Statistical significance between groups was assessed by paired or unpaired Student's t-test, with Bonferroni's correction. A value of p<0.05 was considered statistically significant.

Example 1

Femtomolar Concentrations Of DM Protect LPS-Induced Dopaminergic Neurodegeneration In order to explore whether DM at femtomolar concentrations is neuroprotective against inflammation-mediated dopaminergic neuron degeneration, a wide range of concentrations of DM ($10^{-5}$ M to $10^{-17}$ M) were tested.

Neuron-glia cultures were prepared from the ventral mesencephalic tissues of embryonic day 13-14 Fisher F344 rats or day 12-13 wild-type C57BL/6J (gp91phox$^{+/+}$) mice. Dissociated cells were seeded at $1\times10^5$/well and $5\times10^5$/well to poly-D-lysine-coated 96-well and 24-well plates, respectively. Cells were maintained at about 37° C. in a humidified atmosphere of 5% $CO_2$ and 95% air, in minimal essential medium (MEM) containing 10% fetal bovine serum (FBS), 10% horse serum (HS), 1 gm/l glucose, 2 mM L-glutamine, 1 mM sodium pyruvate, 100 µM nonessential amino acids, 50 U/ml penicillin, and 50 µg/ml streptomycin. Seven-day-old cultures were used for treatment. At the time of treatment, immunocytochemical analysis indicated that the rat neuron-glia cultures were made up of 11% microglia, 48% astrocytes, 41% neurons, and 1% tyrosine hydroxylase-immunoractive (TH-IR) neurons. The composition of the neuron-glia cultures of NADPH oxidase-deficient mice was very similar to that of the wild-type mice in that there were 12% microglia, 48% astrocytes, 40% neurons, and 1% TH-IR) neurons.

Dextromethorphan (obtained from Sigma-Aldrich (St. Louis, Mo.) as dextromethorphan hydrobromide) was freshly prepared as a stock solution (1 mM) in dd$H_2O$ and sterile-filtered right before use. For treatment of the cultures, the DM was serially diluted (10×) with fresh culture medium containing 2% of fetal bovine and horse serum. The neuron-glia cultures were pretreated with $10^{-5}$-$10^{-17}$ M DM 30 minutes prior to treatment with 10 ng/ml of LPS.

Seven days after treatment, the degeneration of dopaminergic neurons was assessed by [$^3$H]-dopamine (DA) uptake assays. The [$^3$H]-DA uptake assays were performed as follows. Cultures were washed twice with warm Krebs-Ringer buffer (KRB, 16 mM sodium phosphate, 119 mM NaCl, 4.7 mM KCl, 1.8 mM $CaCl_2$, 1.2 mM $MgSO_4$, 1.3 mM EDTA, and 5.6 mM glucose; pH7.4) and then incubated for about 20 minutes at about 37° C. with 1 µM [$^3$H]-DA in KRB in order to allow for the uptake of DA. Afterwards, the cultures were washed (three times) with ice-cold KRB and the cells were collected in 1 N NaOH. Radioactivity was determined by liquid scintillation counting. Nonspecific DA uptake observed in the presence of mazindol (10 µM) was subtracted as a control.

The results are expressed as a percentage of the control cultures and are the mean ±S.E.M of three to six individual experiments with triplicates in each experiment. ##, P<0.01 compared with the control culture; *, P<0.05 compared with the LPS-treated culture.

As shown in FIG. 1, DM at micromolar ($10^{-5}$ and $10^{-6}$ M) concentrations attenuated the LPS-induced decrease in [$^3$H]-dopamine uptake. However, it was surprising that femtomolar ($10^{-13}$ M and $10^{-14}$ M) concentrations of DM showed equipotent neuroprotective effect as that of DM at micromolar concentrations. It is interesting to note that nanomolar and picomolar concentrations of DM ($10^{-8}$ M to $10^{-12}$M) showed no protective effects. It appears that this dose-response curve can be divided into three regions: 1) micromolar responsive region, 2) non-response region and 3) femtomolar responsive region. Thus, $10^{-5}$ M, $10^{-10}$ M and $10^{-14}$M were selected as representative concentrations of each of the three regions for further study.

Example 2

Morphological Analysis of DM-Elicited Neuroprotection

The degeneration of dopaminergic neurons was assessed by the observation of changes in tyrosine hydroxylase-immunoreactivity (TH-IR) neuron morphology and a count of the number of TH-IR neurons in neuron/glia cultures prepared and treated with LPS and $10^{-5}$ M, $10^{-10}$ M, and $10^{-14}$ M DM as in Example 1 (counting was performed in a double-blind manner by three individuals).

Dopaminergic neurons were recognized with the anti-TH antibody and microglia were detected with the OX-42 antibody, which recognizes the CR3 receptor. This was accomplished as follows: 3.7% formaldehyde-fixed cultures were treated with 1% hydrogen peroxide for about 10 minutes followed by sequential incubation with a blocking solution (30 min), primary antibody (overnight, 4° C.), biotinylated secondary antibody (2 hours), and ABC reagents (40 min). The color was developed with 3,3'-diaminobenzidine.

For morphological analysis, the images were recorded with an inverted microscope (Nikon, Tokyo, Japan) connected to a charge-coupled device camera (DAGE-MTI, Michigan City, Ind.) operated with the MetaMorph software (Universal Imaging Corporation, Downingtown, Pa.). For visual counting of TH-IR neurons, three wells with the same treatment in the 24-well plate were counted under the microscope at 100× magnification by three different individuals. The average of these scores was reported.

Figure 2A:
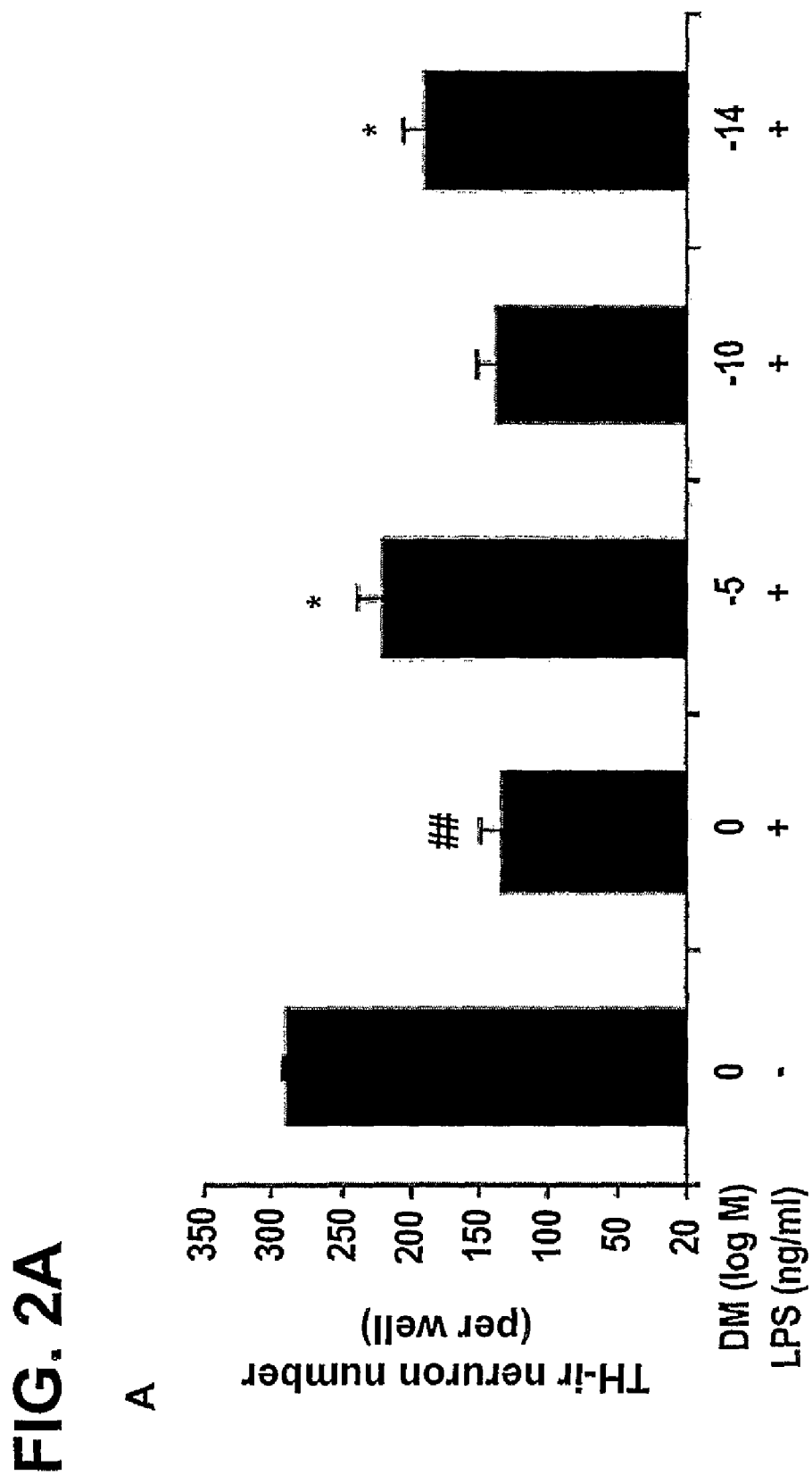
FIG. 2A is a graph representing the number of tyrosine hydroxylase (TH)-immunoreactive neurons in neuron-glia cultures pretreated with various concentrations of DM followed by treatment with LPS.

FIG. 2A shows the results as a percentage of the control cultures, and are the mean ±S.E.M of five individual experiments. ##, P<0.01 compared with the control culture. *, P<0.05 compared with the LPS-treated culture. As seen there, treatment with 10 ng/ml LPS alone caused a significant reduction in the loss of TH-IR neurons (60%) compared with vehicle-treated control cultures. Thirty minute pretreatment with DM $10^{-5}$ and $10^{-14}$ M significantly attenuated the LPS-induced reduction in the number of TH-IR neurons by 37 and 28%, respectively. DM at $10^{-10}$ M had no protective effects on dopaminergic neuron degeneration. The results from the cell counts (FIG. 2A) were comparable to that of the [$^3$H]-dopamine uptake study of Example 1 (FIG. 1).

Figure 2B:
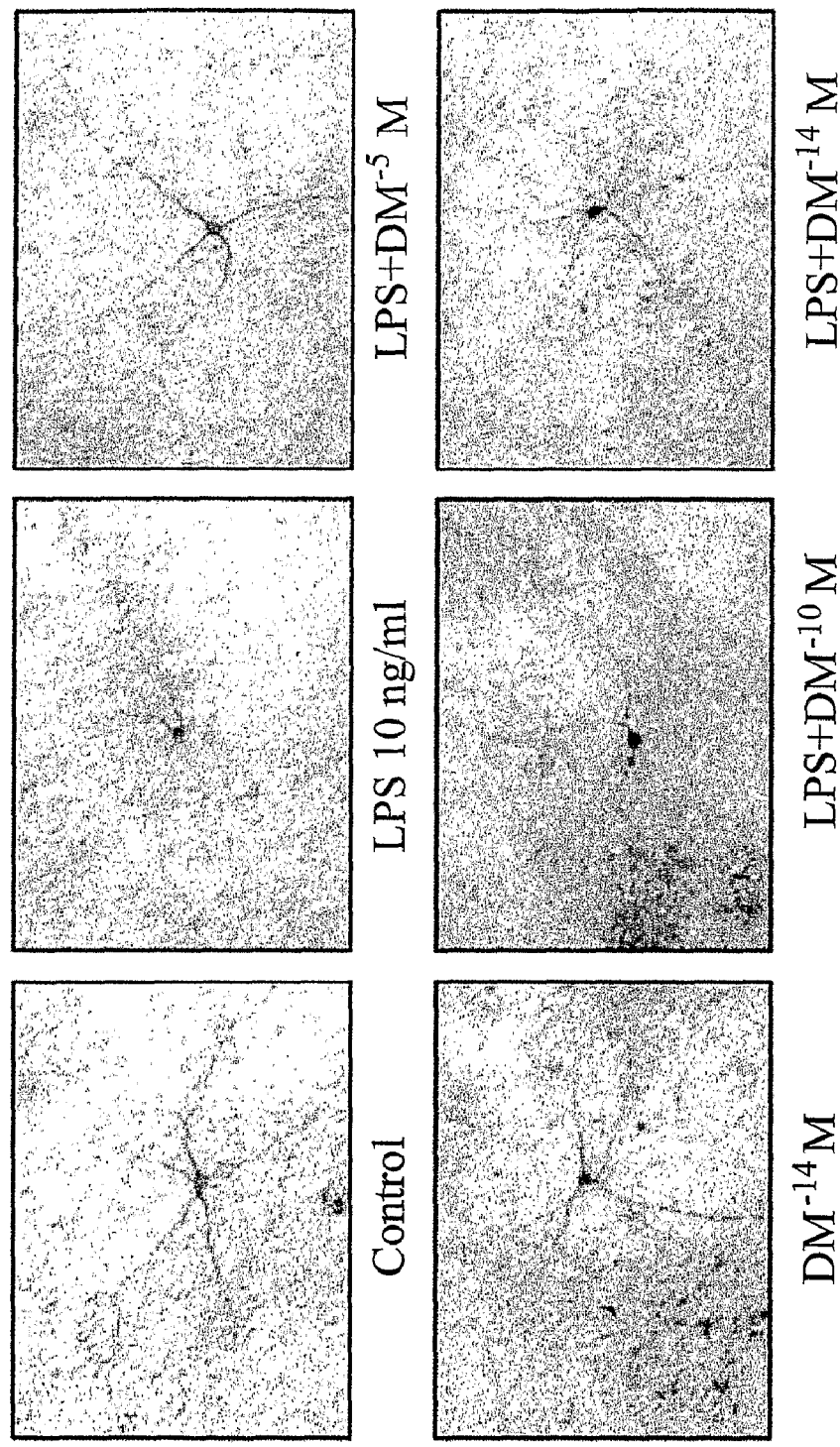
FIG. 2B shows images of immunocytochemically stained dendrite networks that have and have not been pretreated with various concentrations of DM.

Immunocytochemical analysis, shown in FIG. 2B shows the loss of the intricate dendrite network in the LPS-treated group. A more elaborate dendrite network was observed in $10^{-5}$ M and $10^{-14}$ M DM-treated groups, while DM $10^{-10}$ M failed to show improvement. This observation is also consistent with the DA uptake and neuron numeration analysis.

Example 3

Femtomolar Concentrations of DM Protect Aβ-Induced Dopaminergic Neurodegeneration The neuroprotective effects of DM both at micro- and femtomolar concentrations against Aβ-induced neurotoxicity were also investigated.

Neuron-glia co-cultures were prepared and treated with vehicle alone, Aβ 0.75 µM alone, or DM 30 min prior to treatment with Aβ 0.75 µM similar to Example 1. Amyloid-β peptide (25-35 and 1-42) was obtained from American Peptide Co., Inc (Sunnyvale, Calif.). Neurotoxicity was assessed by DA uptake as in Example 1. Results are expressed as a percentage of the control cultures and are the mean ±S.E.M. of three to eight individual experiments with triplicates in each experiment. ##, P<0.01 compared with the control culture; *, P<0.05 compared with Aβ-treated culture.

Figure 3:
FIG. 3 is a graph showing DA uptake as a percentage of the control for neuron-glia cells pretreated with various concentrations of DM followed by sequential treatment with Amyloid-β peptide (Aβ).

Results are shown in FIG. 3, where the neuroprotective effect of DM at both micro- and femtomolar concentrations can be seen against Aβ-induced neurotoxicity.

Example 4

Protective Effect of DM in Aβ- or 1-methyl-4-phenylpyridinium (MPP$^+$)-Induced Dopaminergic Neurodegeneration Neuron-enriched culture were prepared from the ventral mesencephalic tissues of embryonic day 13-14 Fisher F344 rats (Charles River Laboratories, Raleigh, N.C.) as follows. Dissociated cells were seeded at 1×10$^5$/well in 96-well and 5×10$^5$/well to poly-D-lysine-coated 96-well and 24-well plates, respectively. Glial proliferation was suppressed by the inclusion of cytosine β-D-arabinocide (5-10 µM). Seven day old cultures were used for treatment, which were composed of 91% neurons, 9% astrocytes, and <0.1% microglia. The cultures were pre-treated with OM, $10^{-5}$ M, $10^{-10}$ M, and $10^{-14}$ M DM 30 minutes before treatment with vehicle alone, 4 µM Aβ or 0.5 µM MPP$^{+5}$ as in Example 1. DA uptake was also measured as in Example 1 and the results are expressed in both FIGS. 4A and B as a percentage of the control cultures and are the mean ±S.E.M. of four individual experiments with triplicates in each experiment.

Figure 4A:
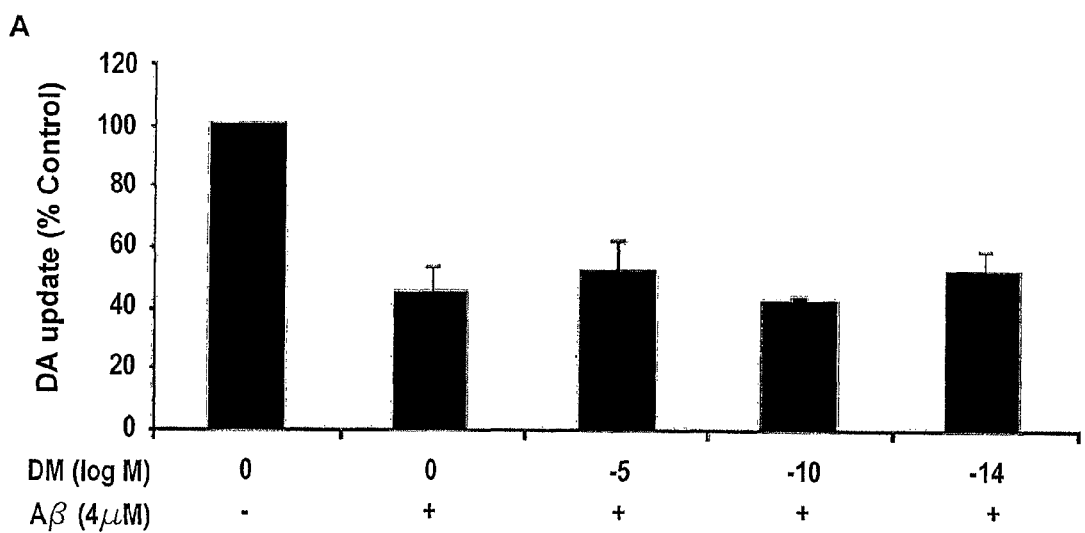
FIG. 4A is a graph depicting DA uptake as a percentage of the control of neuron enriched cultures pretreated with various concentrations of DM followed by Aβ.
Figure 4B:
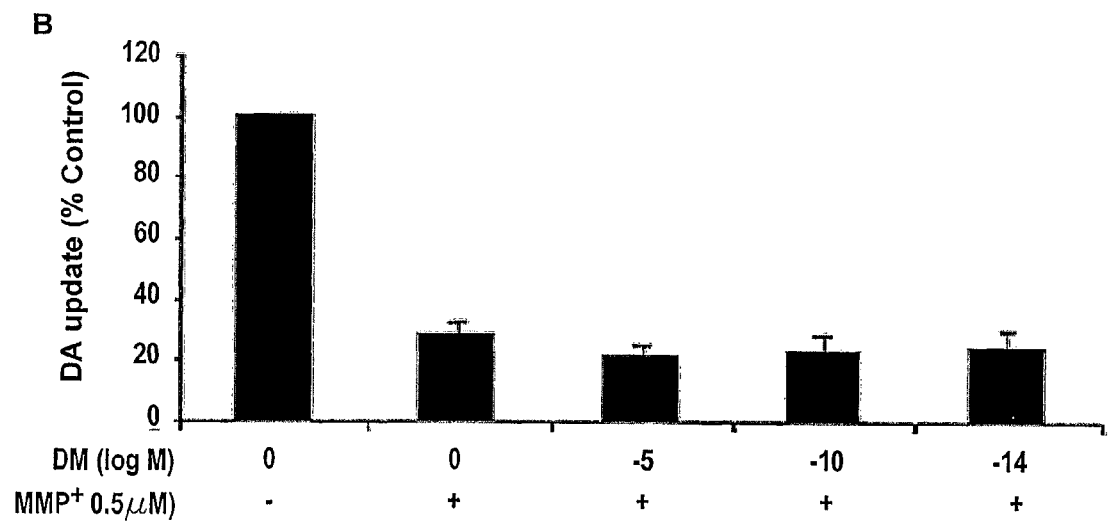
FIG. 4B is a graph depicting DA uptake as a percentage of control of neuron enriched cultures pretreated with various concentrations of DM followed by $MPP^+$.
Figure 9A:
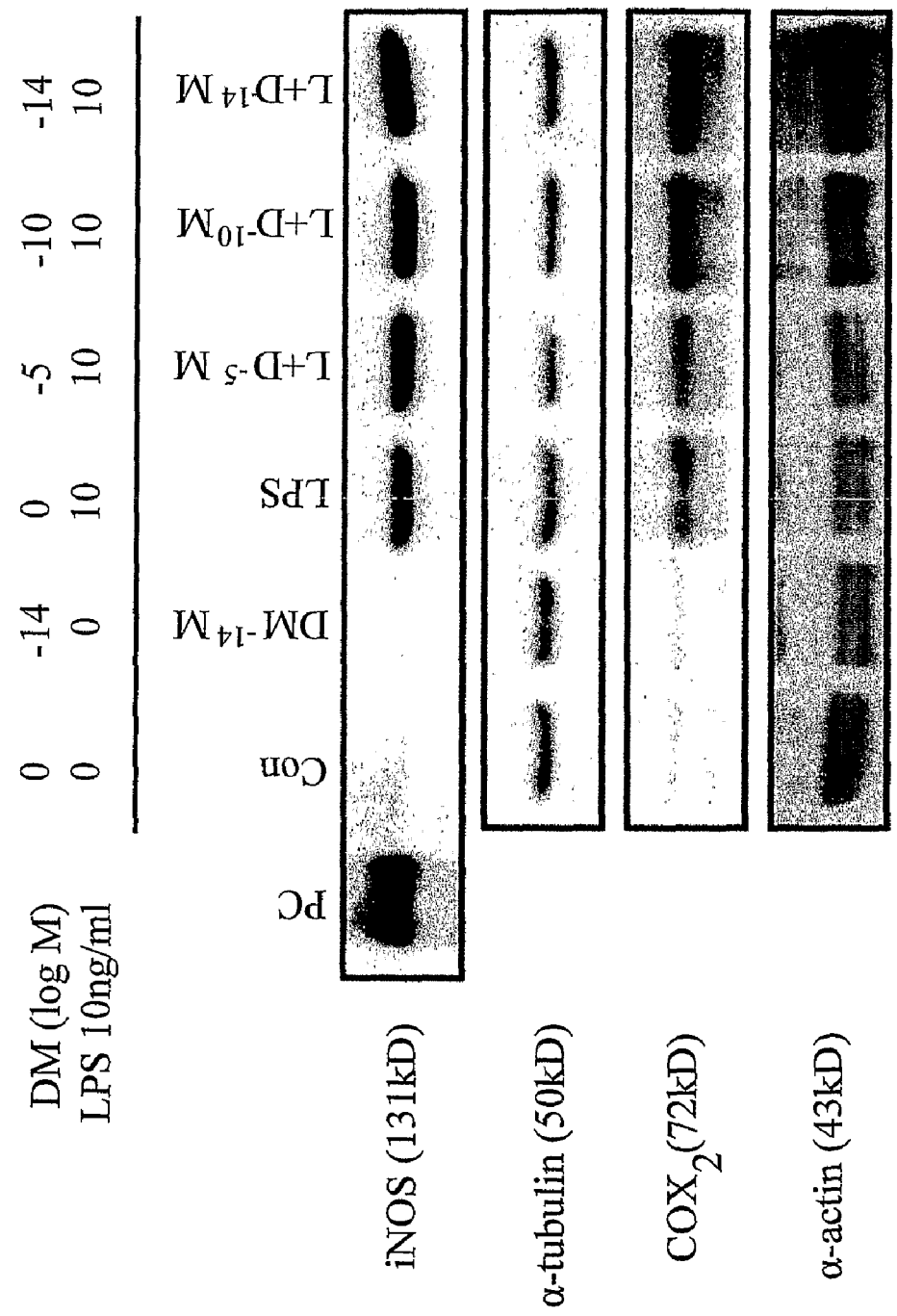
FIG. 9A is an image depicting a Western Blot analysis of iNOS and $COX_2$ production in rat microglia enriched cultures.

As shown in FIG. 4A, 9 days after treatment with 4 µM Aβ (1-42), DA uptake was reduced by 50% compared with the control cultures. Pretreatment of the neuronal cultures with DM ($10^{-5}$ M, $10^{-10}$ M, and $10^{-14}$ M) before Aβ (1-42) treatment did not significantly alter the magnitude of the Aβ (1-42)-induced reduction of DA uptake in the cultures. A similar effect was observed in the samples treated with MPP$^+$ (FIG. 4B). These results suggested that the presence of glial cells may be necessary for DM to express its neuroprotective effect.

In comparing the results from the above examples, the protective effect is only observed in neuron-glia cultures, but not in neuron-enriched cultures, since the DM failed to show a protective effect against Aβ- or MPP$^+$-induced dopaminergic neurotoxicity in neuron-enriched culture regardless of the concentration of DM. This comparison may indicate that femtomolar DM-elicited protection against inflammation-mediated dopaminergic neurotoxicity is dependent on the presence of microglia.

Example 5

Femtomolar DM Inhibits LPS-Induced Microglia Activation

LPS can activate microglia to overproduce pro-inflammatory cytokines and free radicals, such as NO, PGE$_2$, TNFα, superoxide, and other reactive oxygen species (ROS), which in turn can cause neurodegeneration.

Neuron-glia cultures were prepared and treated with vehicle, LPS (5 ng/ml), or LPS plus DM respectively as in Example 1. Twelve hours later, cultures were immunostained with anti-OX-42 antibody. Images shown are representative of three separate experiments. The immunostaining and morphological analysis was accomplished as in Example 2.

Figure 5:
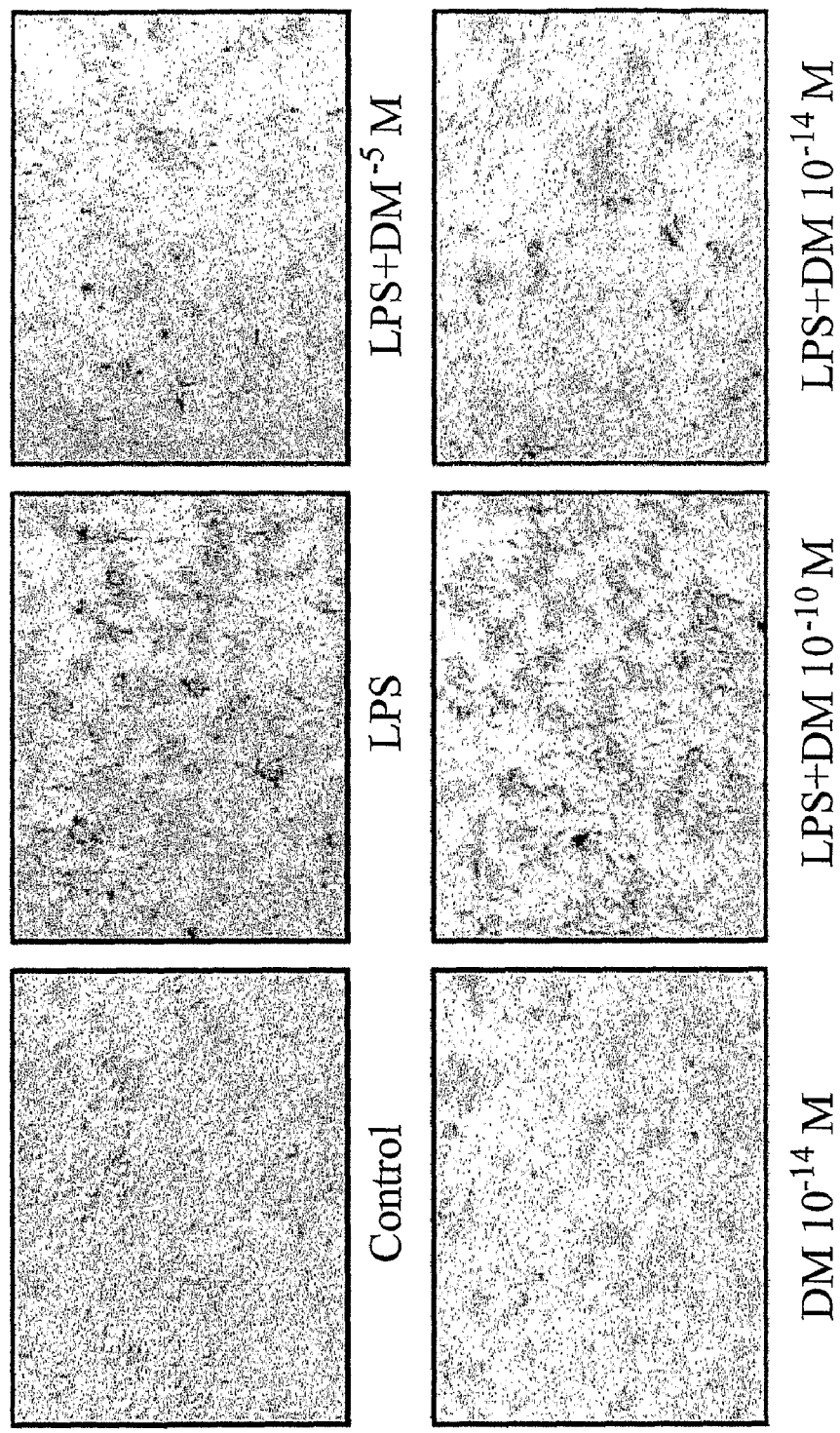
FIG. 5 is a graph depicting photomicrographs of microglia that are pretreated with various concentrations of DM followed by treatment with LPS.

As shown in FIG. 5, LPS treatment transformed the resting, round shape of microglia into the enlarged, irregular shape of activated microglia. Pre-treatment with DM at $10^{-5}$ M and $10^{-14}$ M prevented the LPS-induced activation of microglia. In contrast, DM at $10^{-10}$ M didn't significantly inhibit microglia activation by LPS.

FIG. 5 depicts photomicrographs of microglia showing the inhibitory effect of DM on LPS-induced microglial activation.

Different pro-inflammatory factors that are released from microglia were also monitored. The production of NO was determined by measuring the accumulated levels of nitrite in the supernatant with the Griess reagent, and release of TNFα was measured with a rat TNFα enzyme-linked immunosorbent assay kit from R & D System (Minneapolis, Minn.).

PGE$_2$ in supernatant was measured with a prostaglandin E$_2$ EIA kit from Cayman (Ann Arbor, Mich.) according to the manufacturer's instructions.

The release of superoxide was determined by measuring the superoxide dismutase (SOD)-inhibitable reduction of cytochrome c. To measure the immediate release of superoxide from microglia-enriched or neuron-glia after stimulation, cultures grown in 96-well plates were switched to phenol red-free HBSS (50 µl/well). To each well was added 50 µl of HBSS containing vehicle or DM. The cultures were then incubated at about 37° C. for about 30 min followed by 50 µL of ferricytochrome c (100 µM) in HBSS, with and without 600 U/ml SOD, 50 µl of vehicle or LPS in HBSS. The absorbance at 550 nm was read with a SpectraMax Plus microplate spectrophotometer (Molecular Devices, Sunnyvale, Calif.).

The production of intracellular reactive oxygen species was measured by DCFH oxidation. The DCFH-DA (Molecular Probes, Eugene, Oreg.) reagent passively diffuses into cells in which it is hydrolyzed by intracellular esterase to liberate 2'-7'-dichlorofluoressein which, during reaction with oxidizing species, yields a highly fluorescent compound 2'-7'-dichlorofluorescein (DCF) that is trapped inside the cell. For each measurement, a fresh stock solution of CM-H2-DCFDA (5 mM) was prepared in dimethylsulfoxide. CM-H2-DCFDA, diluted to a final concentration of 1 µM in phenol red-free HBSS containing 2% FBS and 2% HS, was added to cultures and incubated for about 30 min at about 37° C. After washing two times with warm HBSS, vehicle or stimulators in HBSS were added to cultures. After incubation for about 30 min at about 37° C., fluorescence intensity was measured at 485 nm for excitation and 530 nm for emission using a SpectraMax Gemini XS fluorescence microplate reader (Molecular Devices).

Figure 6A:
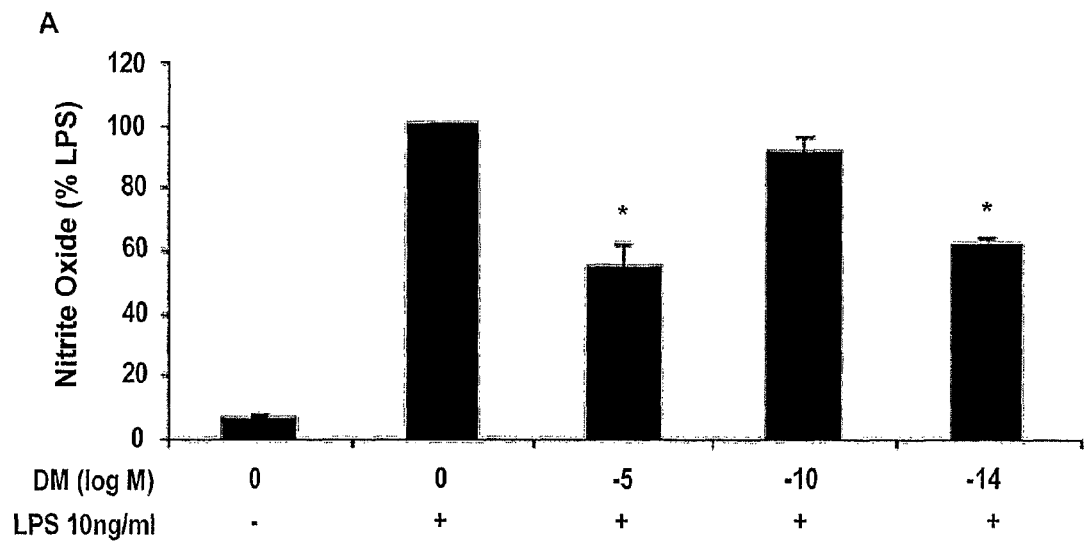
FIGS. 6A, 6B, 6C, 6D, and 6E are graphs depicting the percentage of LPS-induced increase in the release of nitric oxide (FIG. 6A), $PGE_2$ (FIG. 6B), TNFα (FIG. 6C), superoxide (FIG. 6D), and intracellular reactive oxygen species (iROS) (FIG. 6E) that are pretreated with various concentrations of DM.
Figure 6B:
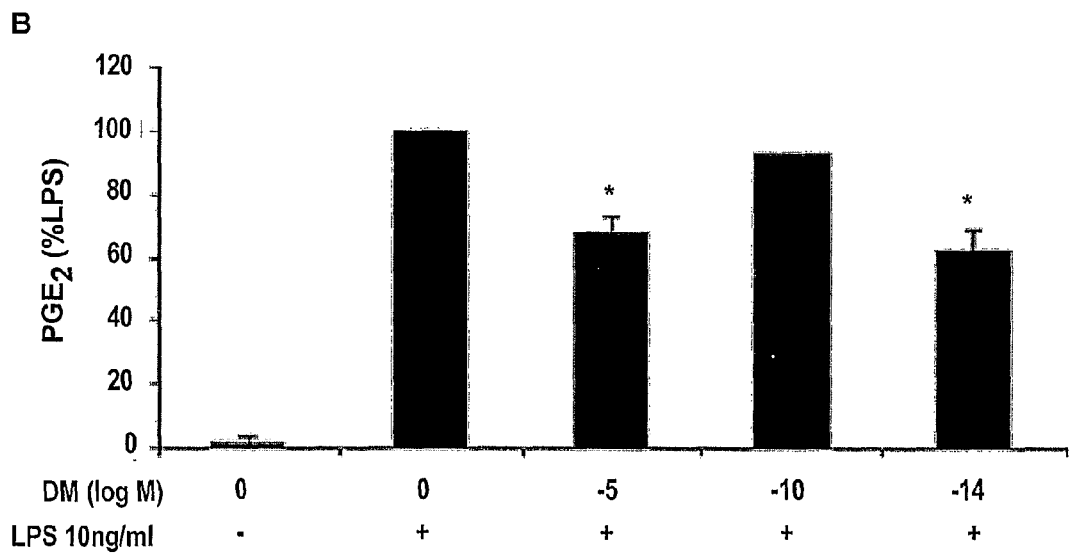
Figure 6C:
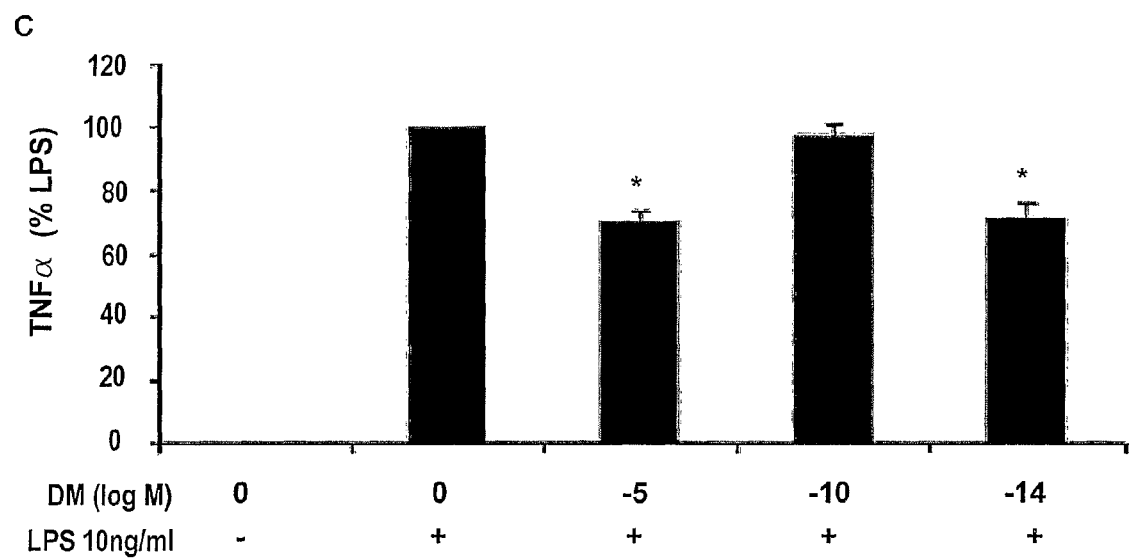

Results are expressed in FIGS. 6A, 6B, and 6C as a percentage of the LPS cultures, in 6D as a percentage of control, and in 6E as absorbance difference above control value. The results are the mean ±S.E.M. of four individual experiments with triplicates in each experiment. *, P<0.05 compared with LPS culture.

Figure 6D:
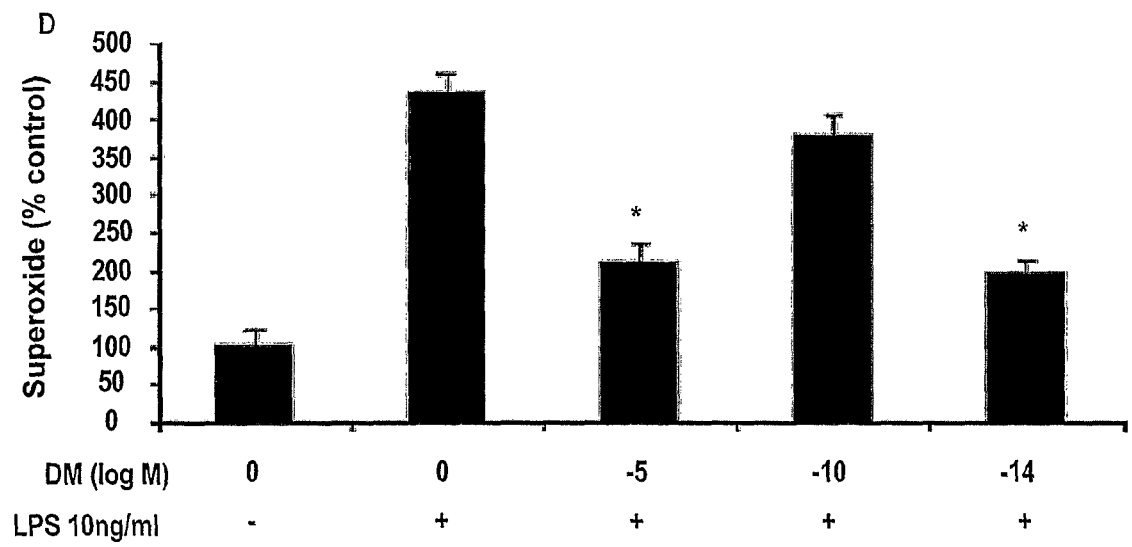
Figure 6E:
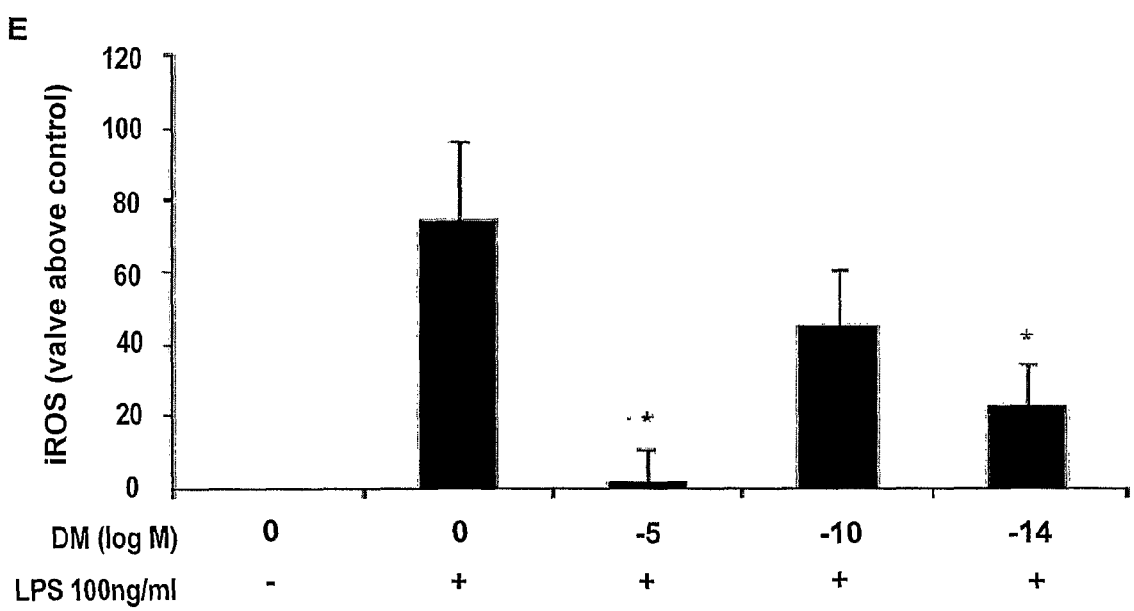

As seen in FIGS. 6A-6C, pre-treatment with DM at $10^{-5}$ M and $10^{-14}$ M significantly decreased the LPS-induced increase in the release of NO, PGE$_2$, TNFα, (FIG. 6C), superoxide (FIG. 6D), and intracellular reactive oxygen species (FIG. 6E) whereas DM at $10^{-10}$ M showed no significant reduction of any of the species.

Example 6

Role of ROS in Mediating DM-Elicited Neuroprotective Effect

To further study the role of ROS in DM-elicited neuroprotection, neuron-glia cultures were prepared from NADPH oxidase-deficient (PHOX$^{-/-}$) and wild-type (PHOX$^{+/+}$) mice.

Microglia were prepared from the whole brains of 1-day-old Fisher F344 rats or NADPH oxidase-deficient (gp91phox$^{-/-}$) (Jackson Laboratory, Bar Harbor Me.) or wild-type mice (C57 BL/6J (gp91phox$^{+/+}$) (Jackson Laboratory, Br Harbor, Me.), as in the above examples. Immunocytochemical analysis accomplished as above indicated that the cultures were 95-98% pure for microglia. Cells were seeded at 1×10$^5$/well in 96-well plates and used for treatment the following day.

The neuron-glia cultures were treated with vehicle, LPS 10 ng/ml alone, and DM ($10^{-14}$ M) 30 min pretreatment followed by LPS treatment as in Example 1. Neurotoxicity was assessed by DA uptake as described in Example 1. TNFα production was measured by ELISA and iROS was determined by DCFDA as in Example 5. Results are expressed as a percentage of the control culture in FIG. 7A, pg/ml in FIG. 7B, and difference from control in FIG. 7C, respectively, and are the mean ±S.E.M. of five individual experiments with triplicates in each experiment. *, P<0.05 compared with LPS culture.

Figure 7A:
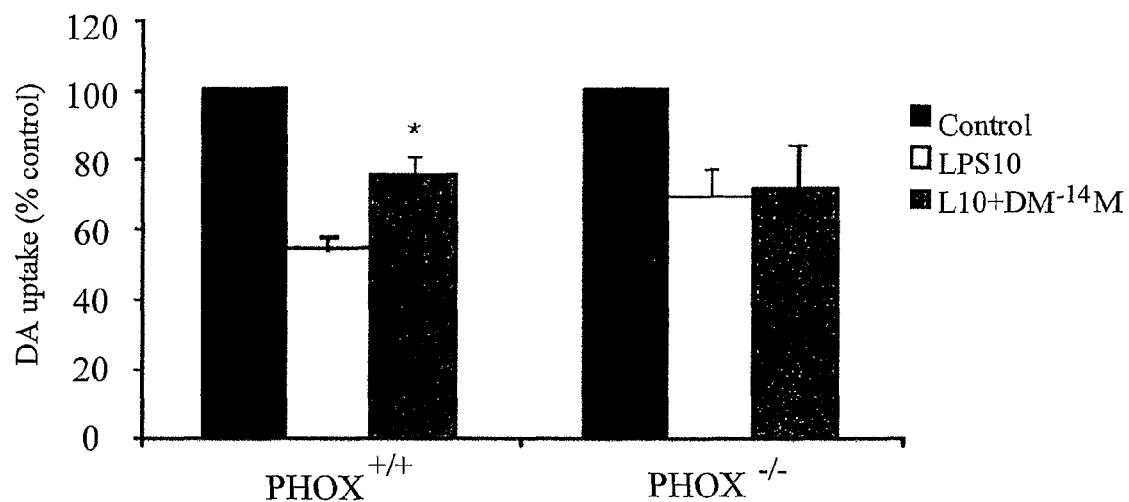
FIGS. 7A, 7B, and 7C are graphs depicting DA uptake (FIG. 7A), TNF-α (FIG. 7B), and iROS production (FIG. 7C) in DM pretreated and non-pretreated $PHOX^{+/+}$ and $PHOX^{-/-}$ mice neuron-glia cultures.
Figure 7B:
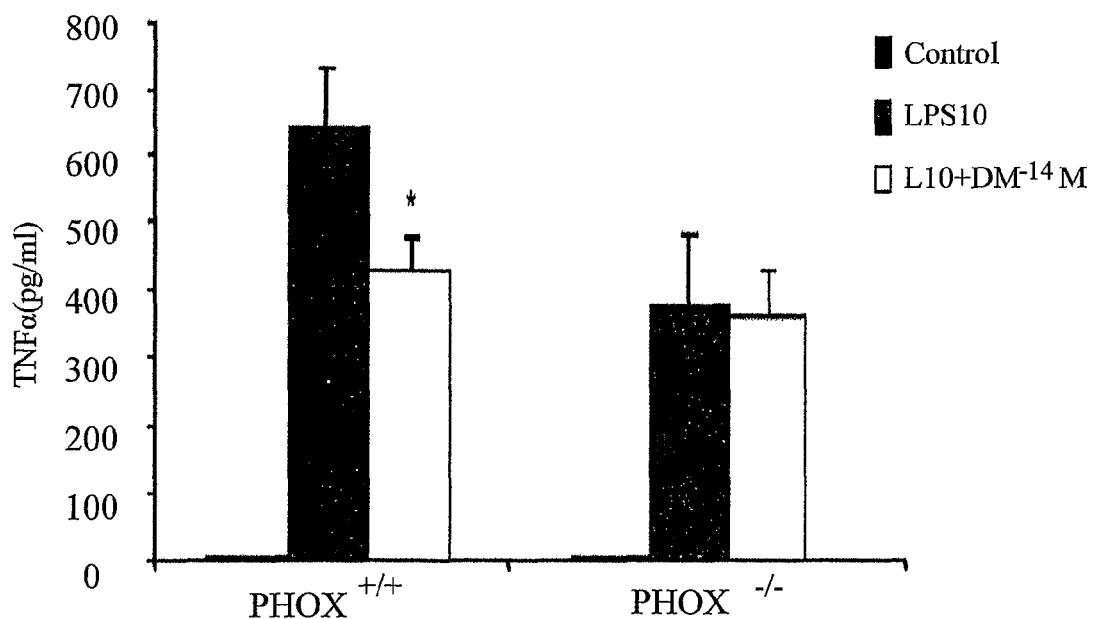
Figure 7C:
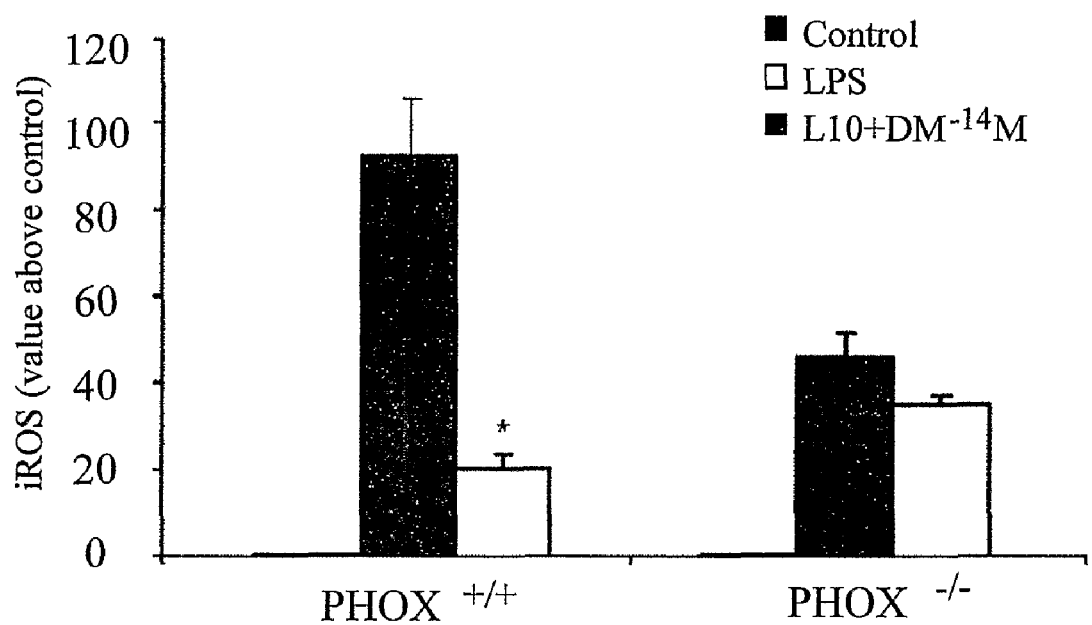

As shown in FIG. 7A, in neuron-glia cultures prepared from PHOX$^{+/+}$ mice, LPS treatment reduced [$^3$H]-dopamine uptake by 46%; $10^{-14}$M significantly attenuated this decrease. In contrast, LPS treatment reduced the uptake capacity by only 25% in PHOX$^{-/-}$ mice and DM ($10^{-14}$M) failed to show any protective effect. Similar to DA uptake result, LPS-induced iROS production in PHOX$^{-/-}$ mice is only half of that in PHOX$^{+/+}$ mice, and DM at $10^{-14}$ M significantly inhibited iROS production in PHOX$^{+/+}$ mice, while failed to show any effect in PHOX$^{-/-}$ mice (FIG. 7C). Consistently, LPS-induced TNFα production in PHOX$^{-/-}$ mice is two thirds of that in PHOX$^{+/+}$ mice, and DM at $10^{-14}$ M was able to significantly reduce TNFα production, which was not seen in PHOX$^{-/-}$ mice (FIG. 7B). These results strongly support the possibility that inhibition of ROS production and subsequently TNFα production may be associated with the neuroprotective effect of DM at femtomolar concentrations.

PHOX is the major superoxide-producing enzyme in microglia and the major contributor to the increase in iROS concentrations in response to a variety of immune stimulants such as LPS, β-amyloid peptides (Aβ). For example, through the activation of PHOX, Aβ at low concentrations increases the production of neurotoxic superoxide, but not the other factors, such as nitrite and TNFα. The findings that micromolar and femtomolar concentrations of DM could protect Aβ-induced dopaminergic neurotoxicity may suggest that DM affords its neuroprotection by inhibiting PHOX activity. Femtomolar DM, while significantly lessening the LPS-induced DA uptake reduction in wild-type mice, has no significant protective effect in PHOX$^{-/-}$ mice (FIG. 7A). These observations support the contention that the protective effect of femtomolar DM may be mediated through the inhibition of PHOX activity. Activation of PHOX in microglia not only increases the production of superoxide, but also indirectly increases the intracellular ROS concentration, possibly through the conversion of superoxide to $H_2O_2$, which is membrane permeable. Increase of iROS can intensify the activation of NFκB, which leads to higher TNFα, PGE$_2$ production. The result that femtomolar DM inhibited TNFα production in wild type while not in PHOX$^{-/-}$ mice further supports the notion that femtomolar DM may be acting on PHOX.

Example 7

Effect of Post-Treatment with DM on LPS-Induced Dopaminergic Neurodegeneration

This example tests whether or not post-treatment with DM is still neuroprotective in LPS-induced neurotoxicity. Neuron-glia co-cultures as prepared in Example 1 were first treated with LPS (20 ng/ml) for twelve hours, and then LPS was removed by removing the media from the cultures and washing twice with PBS.

Different concentrations of DM ($10^{-5}$, $10^{-1}$, and $10^{-14}$ M) were then added to the cultures and incubation was continued for another 6 or 7 days. The DA uptake and the superoxide production were measured as in Example 1 and 5. Results are expressed as a percentage of the control cultures and are the mean ±S.E.M of three to six experiments with triplicates in each experiment. ##, P<0.01 compared with control culture; *, P<0.05 compared with the LPS-treated culture.

Figure 8A:
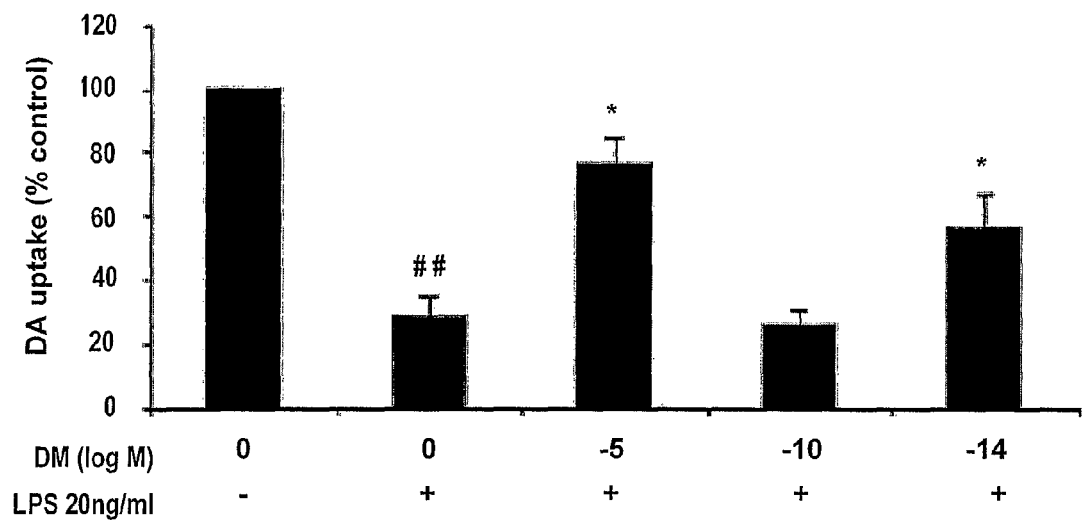
FIGS. 8A and 8B are graphs depicting DA uptake (FIG. 8A), and superoxide production (FIG. 8B) in neuron-glia cultures treated with LPS and various concentrations of DM post-treatment.
Figure 8B:
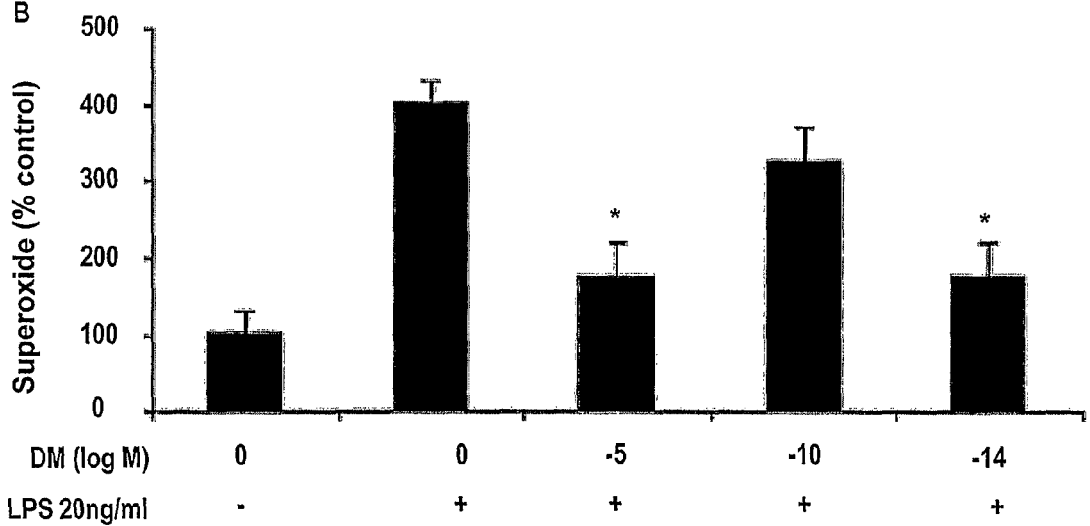

As seen in FIG. 8A, the presence of LPS in the media for only 12 hours was capable of reducing the dopamine uptake capacity by 70%. Post-treatment with DM showed a protective effect at concentrations of $10^{-5}$ and $10^{-14}$ M, but not at $10^{-10}$ M. In the same experiment, superoxide levels were measured in companion cultures 24 hours after LPS treatment. Consistent with pre-treatment studies, post-treatment with DM at $10^{-5}$ and $10^{-14}$ M concentrations significantly inhibited LPS-induced increase in superoxide production. In contrast, neither pre-treatment nor post-treatment with DM at $10^{-10}$ M significantly affected the production of superoxide, as seen in FIG. 8B.

Example 8

Determination of Possibility of Direct Action of DM on iNOS and COX 2 Enzymes

Figure 9B:
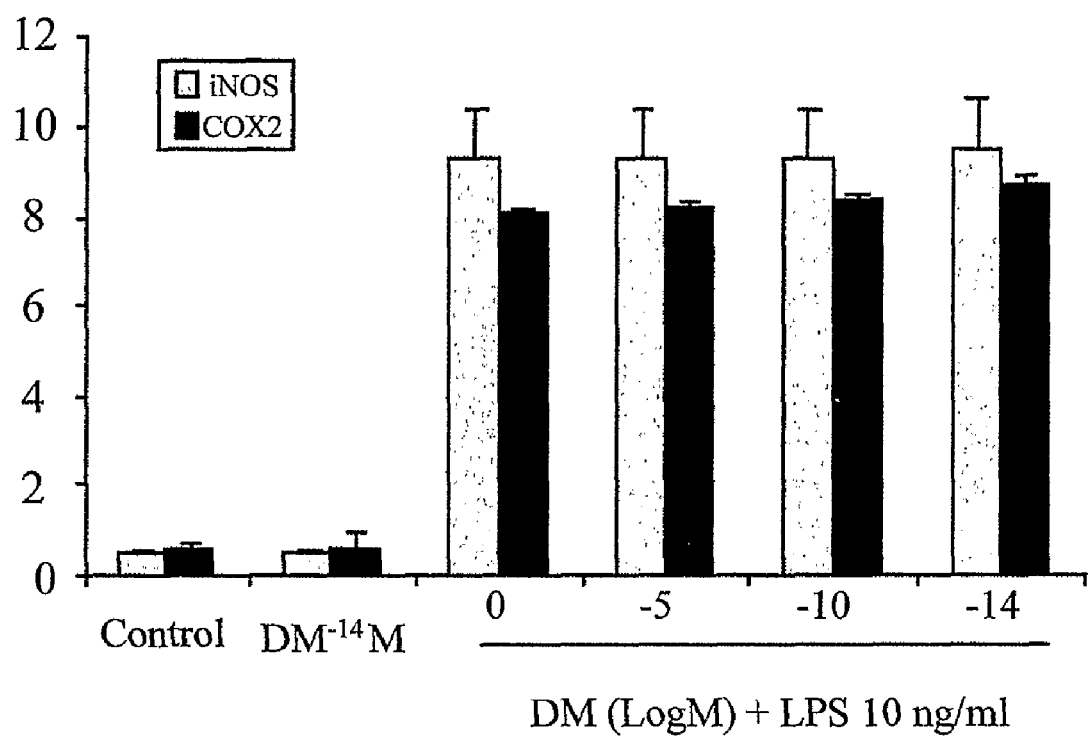
FIG. 9B is a graph quantifying the protein levels of FIG. 9A.

Western blots were used to analyze possible effects of DM on iNOS and COX2 production in rat microglia enriched cultures. The cultures were prepared and treated with vehicle, 0M DM, $10^{-14}$DM, LPS alone, and LPS with different concentrations of DM. The production of iNOS (inducible nitric oxide synthenase) and COX2 (cycloxyase 2) in the culture extracts were detected by Western Blot assay. Protein levels of iNOS were quantified by a densitometer system (n=3) and are reported in FIG. 9B. Data in FIG. 9B represent the mean ±S.E.

Our speculation that femto-molar DM could reduce NO and PGE$_2$ production by directly acting on enzymes iNOS and COX2 was strongly supported by the observation that femto-molar DM 30 min pretreatment reduced NO and PGE$_2$ production while failing to affect the protein content of iNOS and COX2 (FIG. 9).

After the LPS-LBP complex is bound to the membrane protein CD14/TLR4, NFκB is triggered through cascading signaling pathway to regulate the mRNAs encoding iNOS and COX2, which produce NO and PGE$_2$ respectively.

Example 9

Effect of Post Treatment DM on LPS-Treated Micro-Glia Cultures

The cultures were prepared as in Example 1 and were first treated with LPS 20 ng/ml or vehicle; 12 hours later the LPS was removed and the cultures were treated with $10^{-5}$ M, $10^{-10}$ M, and $10^{-14}$ M DM. Twenty four hours later, nitrite oxide and PGE$_2$ production were assessed as in Example 5. The results are expressed as a percentage of LPS treated culture and are the mean ±S.E.M of four and three experiments with triplicates in each experiment. *, p<0.05 compared with the LPS-treated culture. ###, P<0.001 compared with the control culture.

Figure 10A:
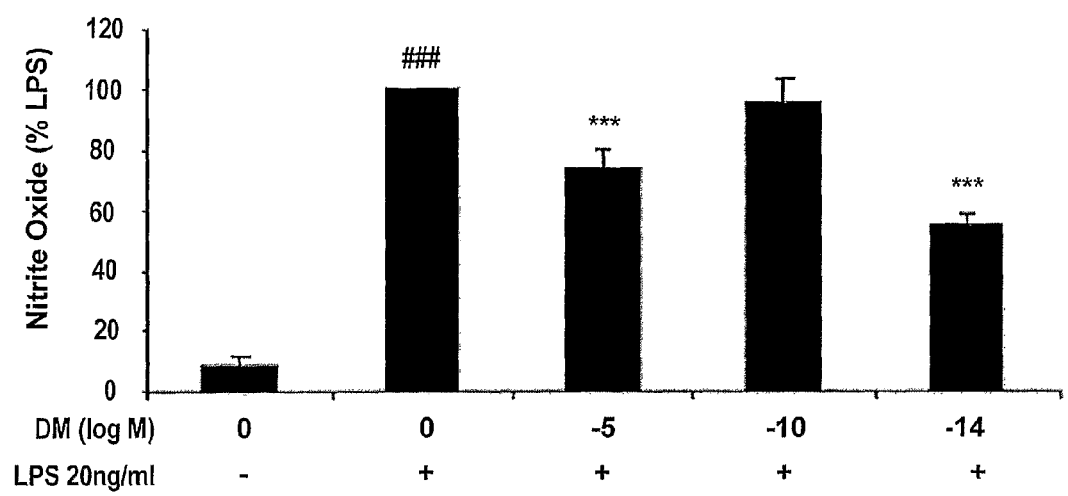
FIGS. 10A and 10B are graphs demonstrating nitrite oxide production (FIG. 10A) and $PGE_2$ production (FIG. 10B) in neuron-glia cultures treated with various concentrations of DM after LPS treatment.
Figure 10B:
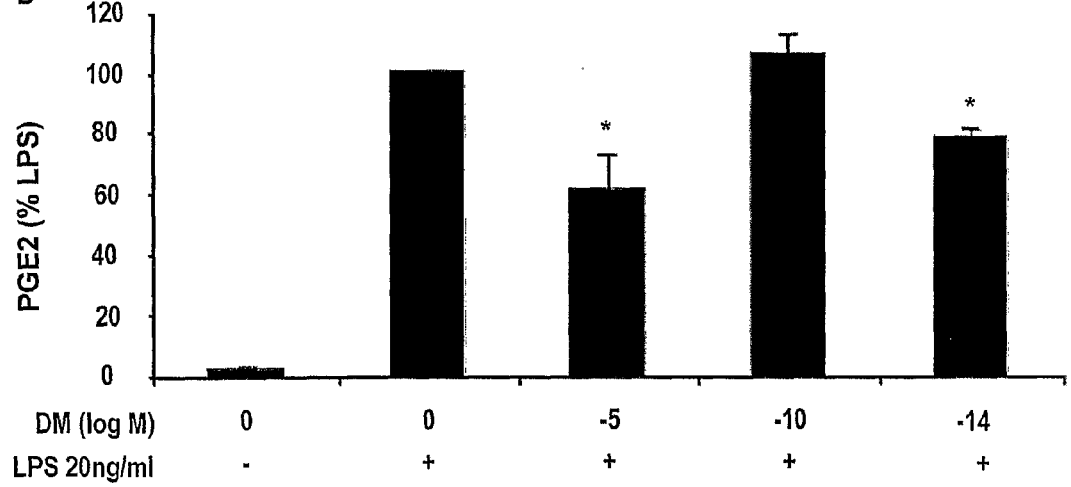

FIGS. 10A and 10B demonstrate that femtomolar DM post treatment following removal of LPS after 12 hours LPS treatment on neuron/glia culture resulted in reduction of NO and PGE$_2$ production without affecting iNOS and COX2 protein levels as evidenced by FIG. 9. Since iNOS and COX2 accumulated within the 12 hours of LPS treatment are sufficient for continuing the production of NO and PGE$_2$ even in the absence of LPS, it was concluded that DM decreased NO and PGE$_2$ production by directly inhibiting the activities of these enzymes. Reduction in the production of nitrite, PGE$_2$ and TNFα, together with the drastic suppression of ROS production, is thought to be one of the mechanisms underlying the potent neuroprotective effect of femto-molar DM.

Example 10

Effect of Various Peptides on LPS-Induced Dopaminergic Neurodegeneration

Femtomolar concentrations of several small peptide fragments of varying lengths and sequences were tested for their ability to protect DA neurons from LPS-induced neurodegeneration in vitro.

Neuron-glia cell cultures were prepared as in Example 1, and pretreated with the various peptide fragments of Table 1 (peptide fragments were obtained from BACHEM) for 30 minutes followed by addition of 5 ng/ml of LPS. DA neurotoxicity was measured as an Example 1 at 7 days post treatment.

The data in Table 1 are expressed as the percent of the control cultures and are the mean ±SEM of 3 experiments performed in triplicate. *P<0.05, **P<0.01, compared to control.

The Dyn A (2-4) peptide, glycine-glycine-phenylalanine (GGF), was found to be the minimal peptide sequence required for neuroprotection, where scrambling the sequence (GFG) proved to be ineffective.

TABLE 1

| Peptide | Control | LPS (5 ng/ml) | LPS + Peptide $10^{-15}$ | LPS + Peptide $10^{-14}$ | LPS + Peptide $10^{-13}$ |
|---|---|---|---|---|---|
| DynA 1-17 | 100 ± 3.9 | 40.1 ± 3.2 | 51.0 ± 9.4* | 58.0 ± 6.5** | 52.1 ± 6.2* |
| DynA 2-17 | 100 ± 3.9 | 40.1 ± 3.2 | 50.2 ± 6.9* | 62.7 ± 8.0** | 44.3 ± 8.2 |
| DynA 1-5 | 100 ± 3.9 | 40.1 ± 3.2 | 54.5 ± 4.6* | 63.5 ± 3.2** | 51.4 ± 4.1* |
| DynA 2-5 | 100 ± 3.9 | 40.1 ± 3.2 | 50.5 ± 5.3* | 58.9 ± 3.9** | 59.4 ± 9.0* |
| DynA 3-8 | 100 ± 3.9 | 40.1 ± 3.2 | 40.9 ± 5.9 | 43.5 ± 1.5 | 39.8 ± 6.2 |
| DynA 6-17 | 100 ± 3.9 | 40.1 ± 3.2 | 38.4 ± 3.9 | 41.9 ± 2.7 | 39.6 ± 5.3 |
| DynA 1-3 | 100 ± 3.9 | 40.1 ± 3.2 | 55.3 ± 3.54* | 70.3 ± 3.38** | 62 ± 3.73** |
| GFG | 100 ± 3.9 | 40.1 ± 3.2 | 40.5 ± 7.3 | 37.1 ± 7.4 | 35.8 ± 5.6 |
| GG | 100 ± 3.9 | 40.1 ± 3.2 | 40.2 ± 5.8 | 42.6 ± 4.8 | 38.9 ± 4.6 |
| GF | 100 ± 3.9 | 40.1 ± 3.2 | 40.2 ± 6.3 | 41.3 ± 4.7 | 40.6 ± 5.5 |

Dynorphin A: YGGFLRRIRPKLKWDNQ

Example 11

Effect of Femtomolar Concentrations of Naloxone and GGF on LPS-Induced Dopaminergic Neurons Mesencephalic neuron-glia cultures were prepared as in Example 1 and were treated with either vehicle, LPS (5 ng/ml) or were pretreated for 30 minutes with naloxone or GGF ($10^{-12}$–$10^{-16}$M) followed by addition of LPS (5 ng/ml) as described in Example 1. DA neurotoxicity was measured at 7 days post treatment as in Example 1. Dopaminergic neuronal death was determined at 7 days post treatment using immunocytochemical staining as in Example 2. The ability of GGF and naloxone to protect DA neurons from LPS-induced damage is depicted by immunocytochemical analysis with anti-TH antibody as in Example 2. The data are expressed as the percentage of the control cultures and are the mean ±SEM from three independent experiments, each performed with triplicate samples. * P<0.05, ** P<0.01 compared to control.

Figure 11A:
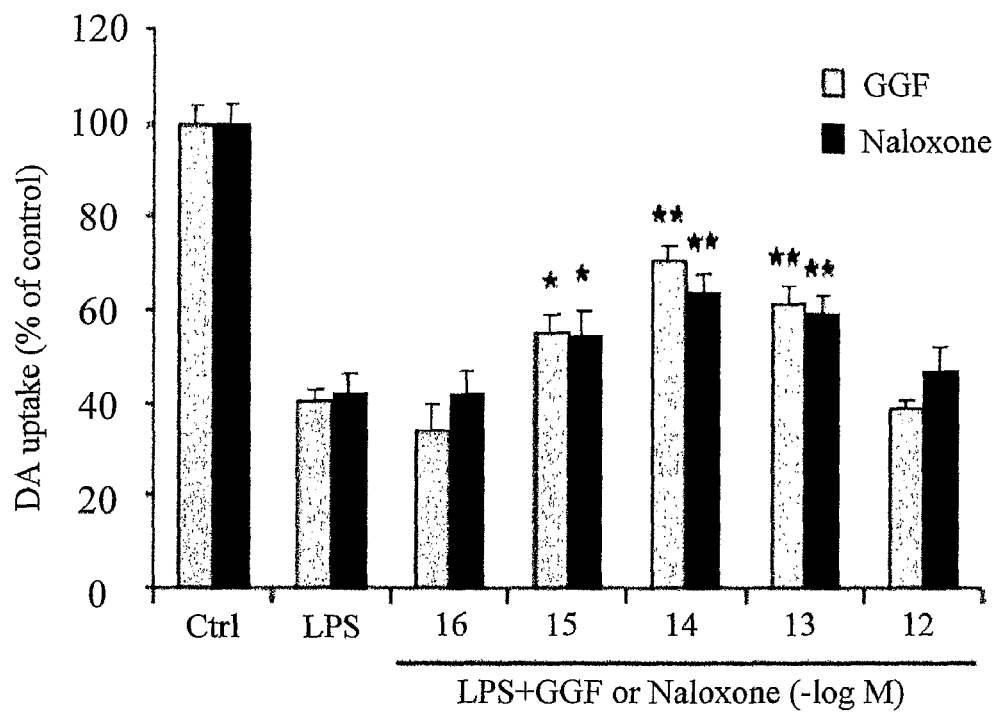
FIG. 11A is a graph illustrating DA uptake of neuron-glia cells with and without pretreatment by varying concentrations of the tripeptide GGF and naloxone followed by treatment with LPS.

FIG. 11A shows that both the peptide GGF and naloxone exhibit similar neuroprotective qualities at femtomolar concentrations. The ability of DA neurons in mesencephalic cultures to take up [$^3$H] DA after exposure to LPS was enhanced by approximately 35% with 30 minute pretreatment of either naloxone or GGF, with the greatest level of protection conferred at the concentration of $10^{-14}$M for both compounds.

Figure 11B:
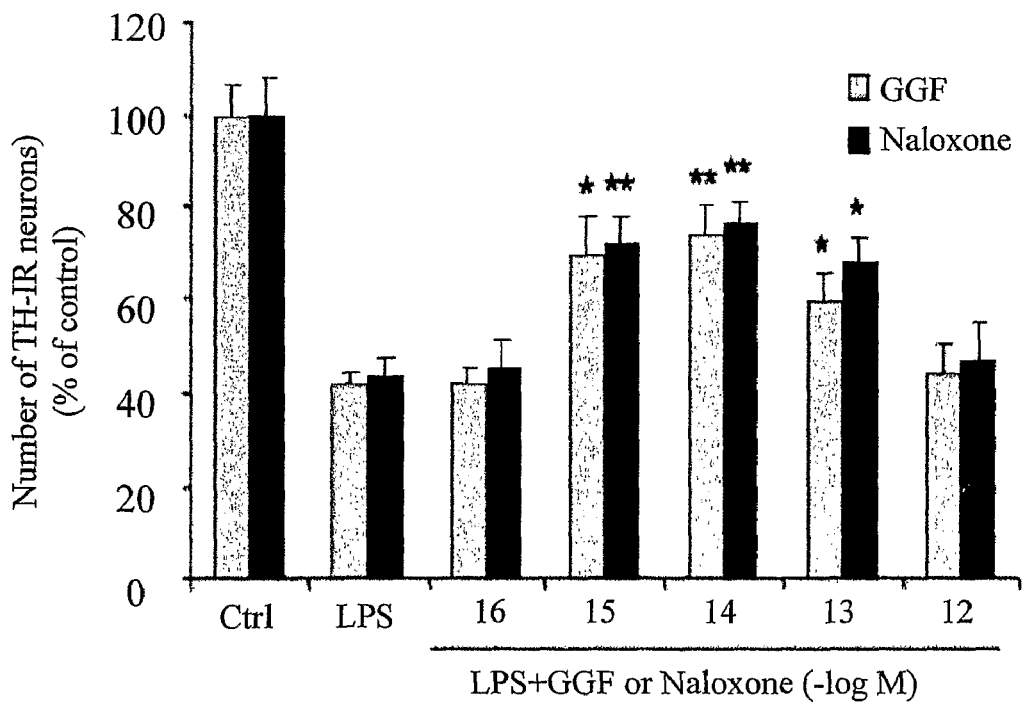
FIG. 11B is a graph illustrating the number of TH-IR neurons after treatment with varying concentrations of the tripeptide GGF and naloxone followed by LPS treatment.
Figure 11C:
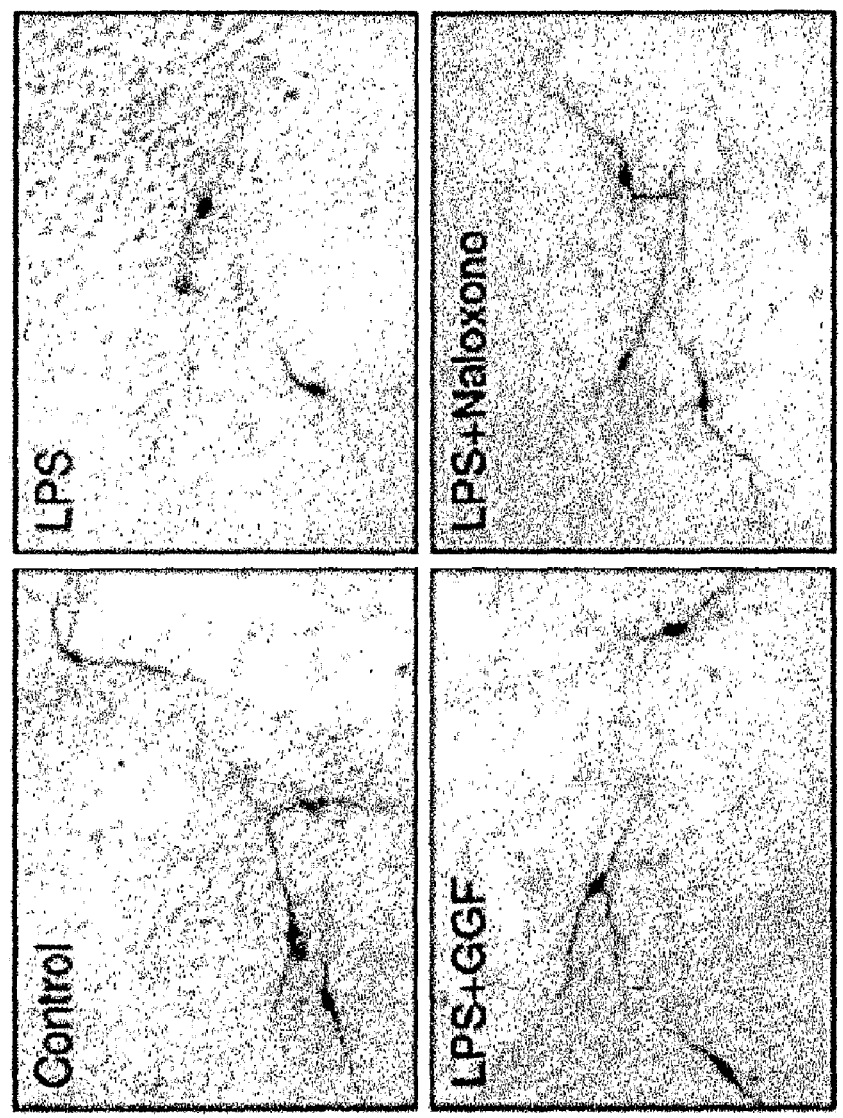
FIG. 11C are photomicrographs of immuno-reactive neurons treated with LPS, LPS plus the tripeptide GGF, and LPS plus naloxone.

FIG. 11C shows that both $10^{-14}$M naloxone and $10^{-14}$M GGF protected TH immuno-reactive neurons from LPS-induced damage, such as loss of dendrites, axon disintegration, and loss of DA neurons. FIG. 11B evidences that GGF and naloxone pretreatment protected against LPS-induced DA neuron cell loss, with the peak protection occurring at $10^{-14}$M for both GGF and naloxone. Taken together, these results indicate that both the peptide, GGF, and the naloxone protected neurons from LPS-induced DA neuron cell death and loss of function with a similar efficacy and dose response.

Example 12

Effects of Femtomolar Concentrations of GGF and Naloxone on the Production of Various Species by Neuron-Glia Cultures Primary enriched-microglia cultures were prepared as in Example 1. The cultures were pretreated with varying concentrations of naloxone for about 30 minutes and GGF followed by treatment with 10 ng/ml LPS as in Example 1. The intracellular ROS concentrations and superoxide amounts were measured as in Example 5. The data are expressed as the percent of the control cultures and are the mean ±SEM of three experiments performed in triplicate. *P<0.05, **P<0.01, compared to control.

Figure 12A:
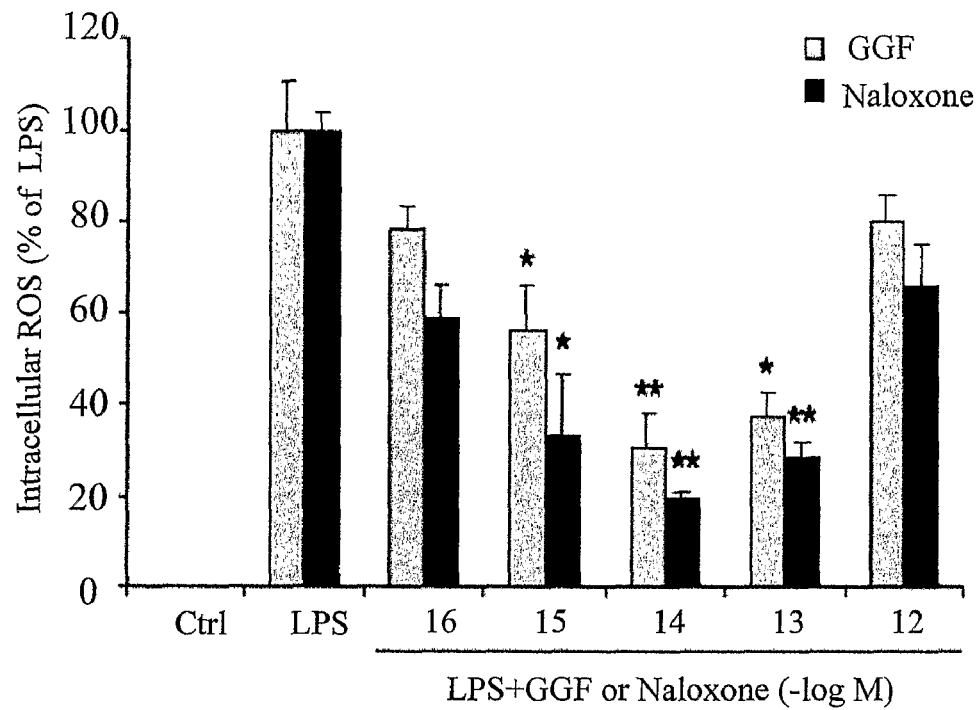
FIGS. 12A and 12B are graphs showing the production of iROS (FIG. 12A) and extracellular superoxide (FIG. 12B) of neuron-glia cultures treated with GGF or naloxone followed LPS treatment.
Figure 12B:
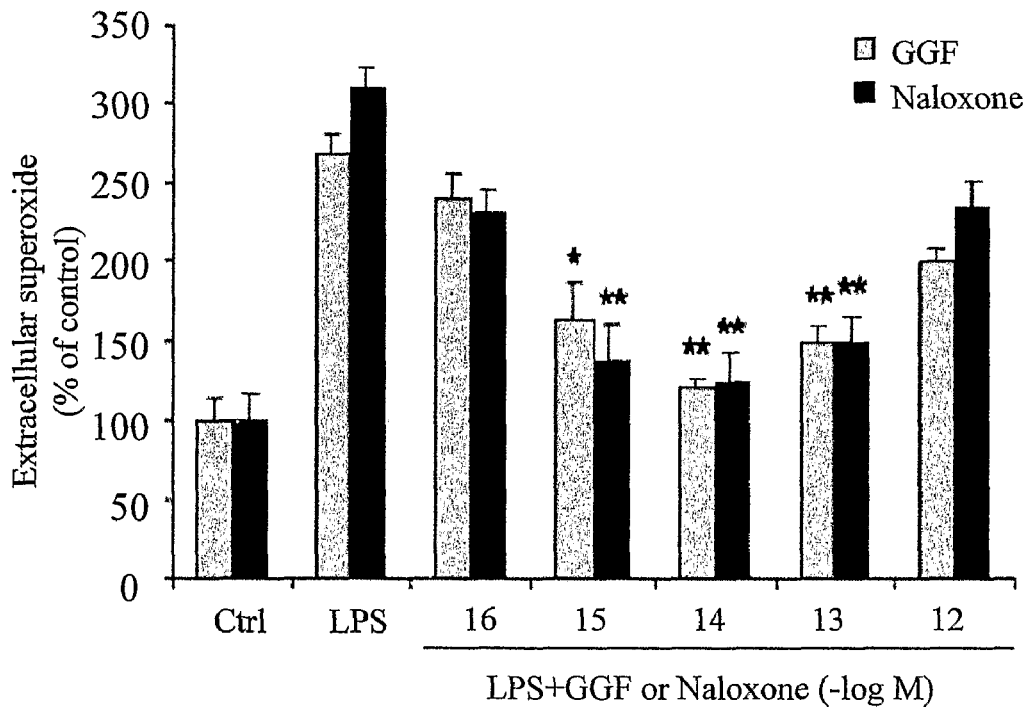

Both $10^{-14}$M Nal and $10^{-14}$M GGF reduced intracellular ROS concentrations by 65% (FIG. 12A) and reduced microglial superoxide response to nearly control levels (FIG. 12B). These results demonstrate a similar efficacy and dose response of GGF and naloxone on microglial ROS levels, one of the pivotal signaling mechanisms governing microglia-mediated neurotoxicity.

Example 13

Effect of Femtomolar Concentrations of GGF and Naloxone on Mesencephalic Cultures from NADPH Oxidase Deficient Mice The rat and mouse ventral mesencephalic neuron-glia cultures were prepared as in Example 1. Mesencephalic neuron-glia cultures from PHOX$^{-/-}$ and PHOX$^{+/+}$ mice were treated with either vehicle, LPS (5 ng/ml), or were pretreated for 30 minutes with Naloxone or GGF ($10^{-13}$ M-$10^{-14}$M) followed by addition of LPS (5 ng/ml) as in Example 1. DA neurotoxicity was measured by using the [$^3$H] DA uptake assay as in Example 1. The data are expressed as the percent of the control cultures and are the mean ±SEM. The release of TNFα was measured with a commercially available enzyme-linked immunosorbent assay kit. *P<0.05, **P<0.01, compared to control. The amount of TNFα was measured as in Example 2.

Figure 13A:
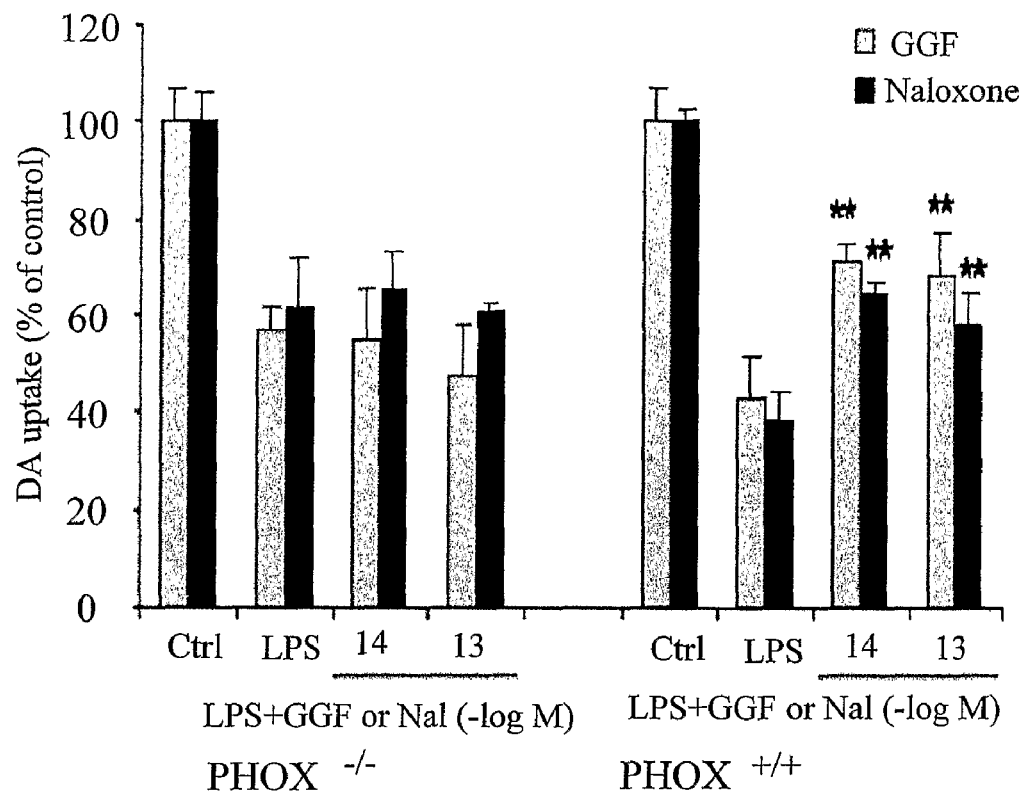
FIGS. 13A and 13B are graphs showing DA uptake (FIG. 13A) and TNFα production (FIG. 13B) for mesencephalic cultures from $PHOX^{+/+}$ and $PHOX^{-/-}$ mice pretreated with varying concentrations of GGF or naloxone followed by treatment with LPS.

Both naloxone and GGF failed to show neuroprotection in PHOX$^{-/-}$ cultures (FIG. 13A), supporting that inhibition of this enzyme is critical to the mechanism of action. The TNFα production was measured in response to LPS in PHOX$^{-/-}$ and PHOX$^{+/+}$ mesencephalic neuron/glia cultures pretreated for 30 minutes with GGF and Nal.

Figure 13B:
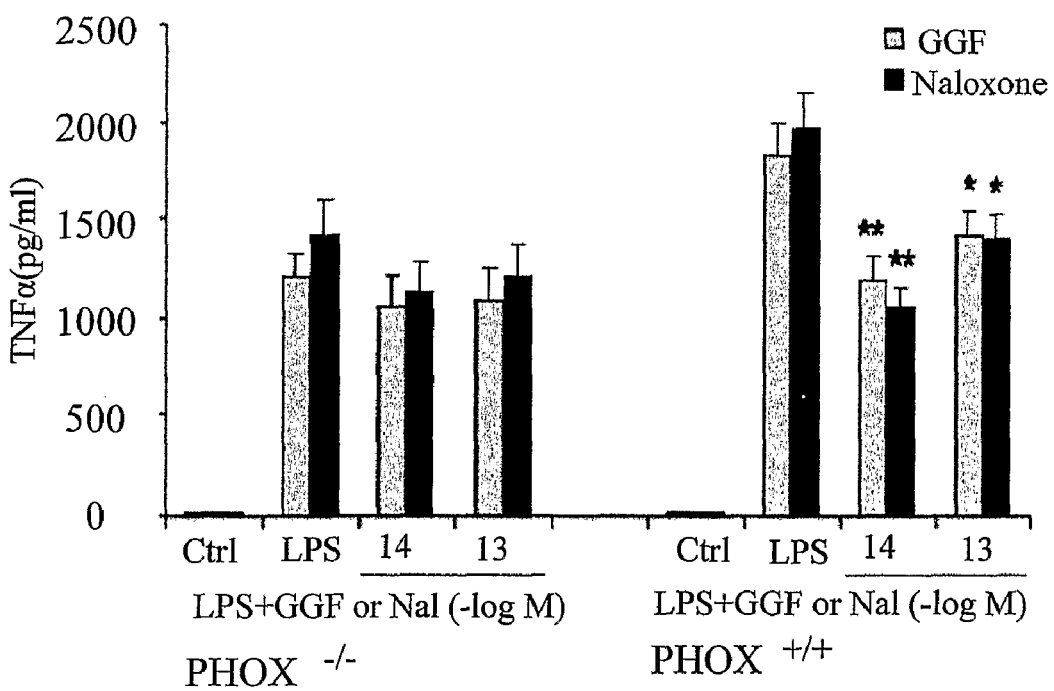

Again, PHOX$^{-/-}$ mice failed to show any TNFα reduction in response to LPS with pretreatment of either neuroprotective compound, while the control mice showed a reduction of TNFα with Nal and GGF treatment ($10^{-14}$M) (FIG. 13B), demonstrating that these femtomolar acting compounds also inhibit the ROS-induced amplification of TNFα expression. Together, these results support the conclusion that GGF and Nal afford neuroprotection through inactivation of NADPH oxidase.

The failure of Nal or GGF to protect against LPS-induced neurotoxicity in PHOX$^{-/-}$ cultures indicates that NADPH oxidase may be a component to the mechanism of neuroprotection.

Example 14

Molecular Modeling of Naloxone and GGF

Given the striking functional and mechanistic similarity between naloxone and GGF at femtomolar doses, it was thought these two compounds might act on the same site. To investigate this hypothesis, both compounds were compared for structural and chemical similarities. The Search Compare Module of the Accelrys Insight II software package was used to provide a systematic conformational search of sterically permitted conformations for both naloxone and the tripeptide, Gly-Gly-Phe. Accessible conformations of both molecules were then compared and superimposed based on electrostatic potential similarity (as defined by the program Good, A. C., Hodgkin, E. E., Richards, W. G., "Utilization of Gaussian Function for the Rapid Evaluation of Molecular Similarity", J. Chem. Inf. Comput. Sci, 32, 188-191, 1992) and steric shape similarity (as defined in the Search_Compare User Guide, Oct. 1995, San Diego: Accelrys/Biosym/MSI, 1995) p. 2-3). The GGF peptide was built within the InsightII software suite using the Biopolymer builder.

A conformational search was defined based on rotatable bonds, where 166 conformations were identified (66 of which were redundant) resulting in 100 uniquely defined conformations. (The Phe ring was kept in one planar orientation and conformations rotating this ring were not explored). These conformations were energy minimized resulting in 42 distinct energy-minimized conformations. These 42 GGF peptide conformations were compared in terms of electrostatic and steric-shape similarity with naloxone. Naloxone, as a fused ring compound, has less conformational flexibility than the GGF tripeptide.

Figure 14:
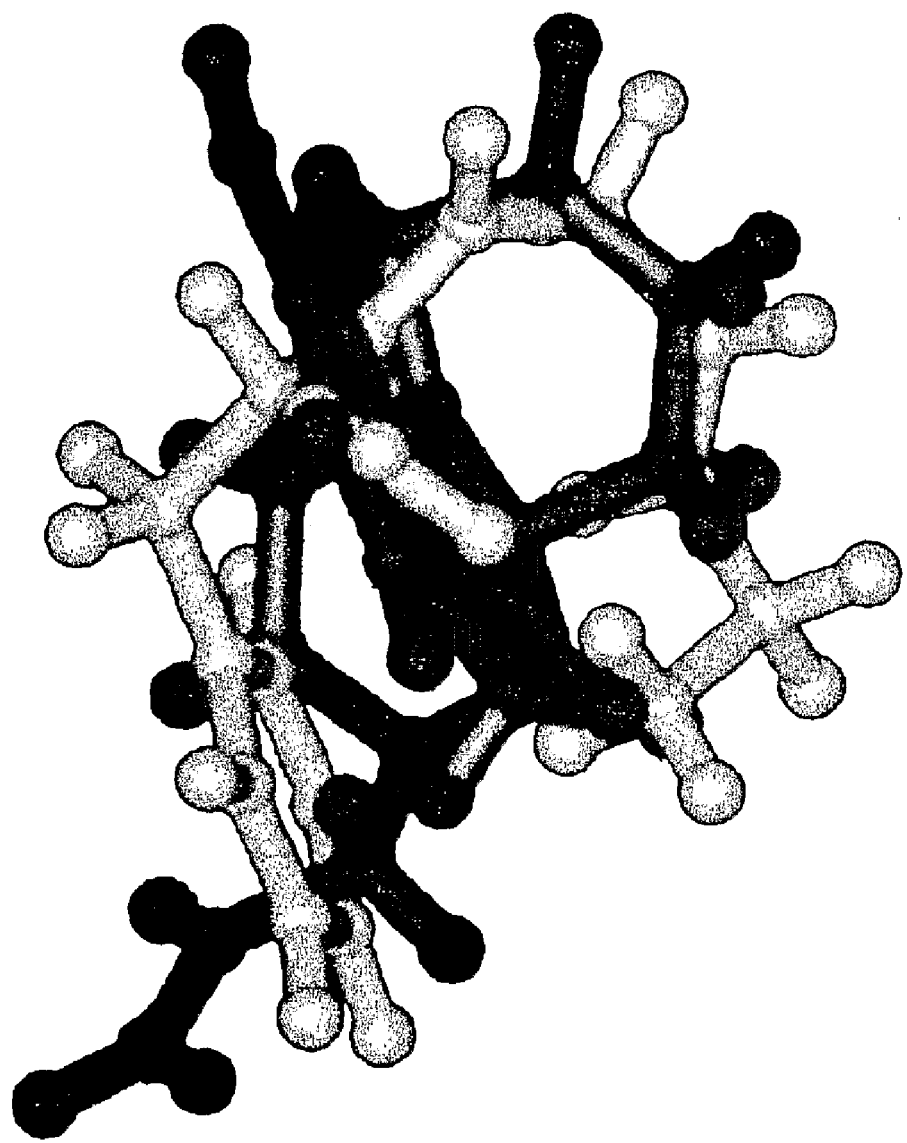
FIG. 14 is a structural representation comparing of one of the GGF tripeptide conformations (light) superimposed on one of the conformations of naloxone (dark).

The steric similarity function for two low energy stable conformations of naloxone and GGF was 0.854, (i.e. identical molecules would share steric similarity function=1.0; most dissimilar molecules, -1.0), indicating that the two molecules have the potential for exhibiting similar steric interactions and therefore could fit within a similarly shaped binding pocket depicted in FIG. 14. This is particularly intriguing and surprising because while both DynA (the full length sequence from which GGF is derived), and naloxone are known to bind the kappa opioid receptor, GGF is missing the first amino acid (tyrosine) required to bind the kappa receptor, suggesting that the similarity in steric conformations and interactions is critical to a site of action independent of the opiate receptors.

Example 15

Binding of Naloxone to NADPH

Binding affinities of naloxone for COS-7 cells transfected with gp91/p22 was determined using either [$^3$H]-(+)Naloxone or [$^3$H]-(-)Naloxone (2 nM; PerkinElmer Life Sciences) as ligands and displaced with 10 μM of cold (-)Naloxone in HBBS containing 0.1% (W/V) fatty acids free albumin (lot B22558, Calbiochem). COS-7 cells transfected with gp91/p22 and COS-7 cells that were not transfected (WT) were detached using Versene (1:5000, GibcoBRL, Life technologies). For intact cell assays, after washing twice with HBSS, cells were transferred to micro centrifuge tubes at $10^6$ cells per tube.

To acquire membrane preparations, cells were lysed in buffer (20 nM Tris, pH=7.4, 2 mM EDTA, 10 μg/ml CLAP) and homogenized. Lysate was transferred to a 50 ml conical tube, where there were centrifuged at 250 g for about 10 minutes at about 4 C. The supernatant was then transferred to another tube and spun at 100,000 G for about 90 minutes. The supernatant was then discarded and the protein pellet was re-suspended in 2 ml of lysis buffer. Finally, 50 μg of protein was aliquoted into a 1.5 ml tube for further assay.

All competition reactions of either intact cells or membrane preparations were allowed to proceed at 4° C. Cells or membrane preparations were incubated with either [$^3$H]-(+) Naloxone or [$^3$H]-(-)Naloxone with gentle mixing in a roller drum for one hour. Experiments were terminated by rapid filtration through Glass fiber filters (F4144-100EA, Sigma-Aldrich) using a sampling manifold (XX2702550, Millipore). After washing with HBSS four times, the filters were collected and radioactivity retained on the filters was determined by liquid Scintillation counting. All values are expressed as percentages relative to the binding capacity of the wild type control. To determine whether COS-7$^{gp91/p22}$ transfected cells had an increased level of general non-specific binding, binding affinities of LPS for COS-7 cells transfected with gp91/p22 was determined either with [$^3$H]-naloxone (2 nM; PerkinElmer Life Sciences) as ligands displaced with 10 μM of cold naloxonein HBBS containing 0.1% (W/V) fatty acids free albumin (lot B22558, Calbiochem).

Figure 15:
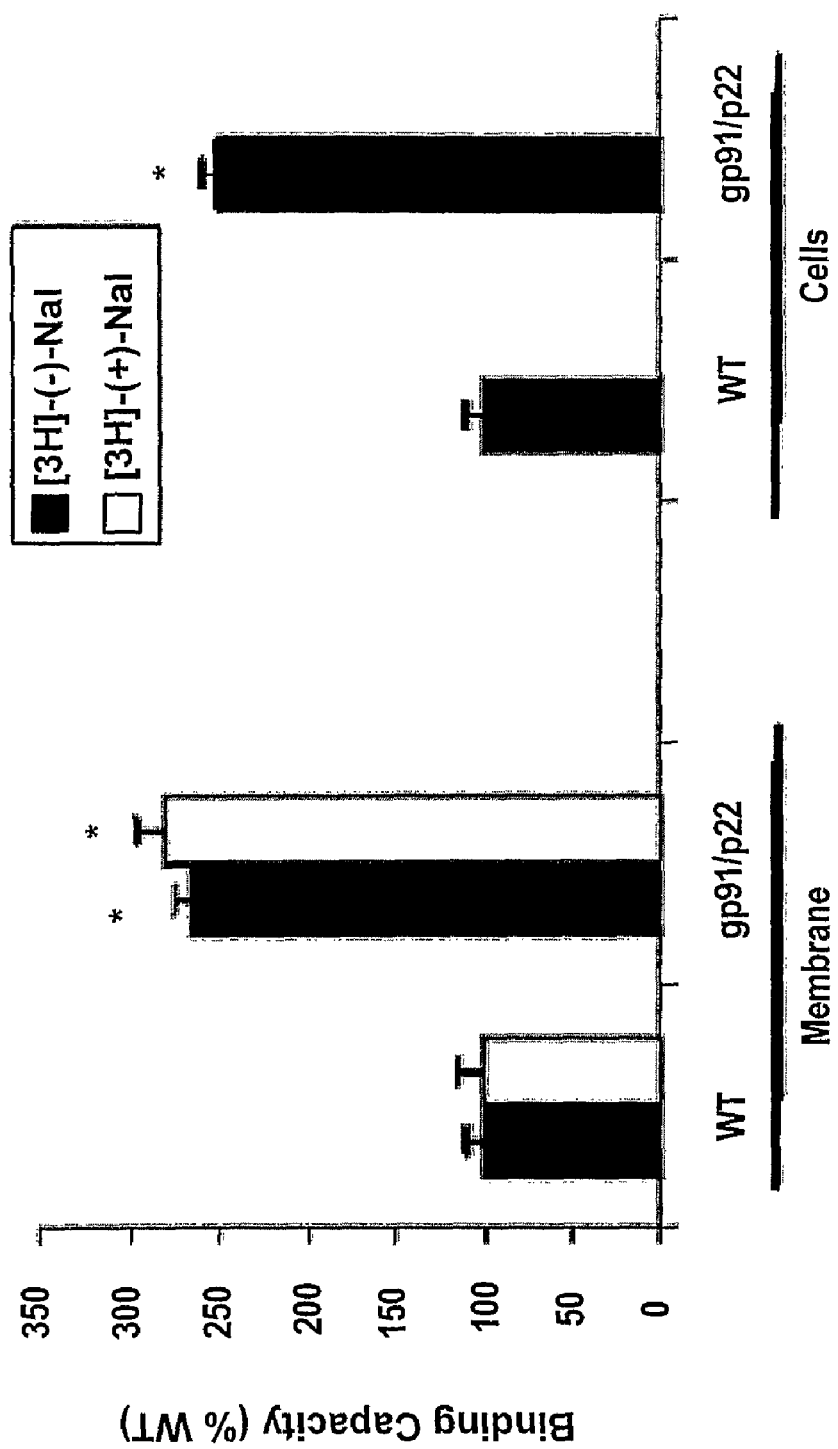
FIG. 15 is a graph comparing the binding capacity of naloxone to wild type cells and cells that do not express the gp91 subunit of NADPH.

The study showed that COS-7$^{gp91/p22}$ cells, an immortal kidney cell line stably transfected with gp91/p22, have an increased binding capacity (150-180%) above the control COS-7 cells, which do not express gp91 (NADPH oxidase membrane bound catalytic subunit) or p22 (NADPH oxidase membrane anchor protein) (FIG. 15). This data offers support for the hypothesis that naloxone binds to the gp91 protein.

Example 16

In Vivo Effect of Dextromethorphan on TNFα(iROS, and alanine aminotransferase (ALT)

Animal studies were performed in accordance with National Institutes of Health Guidelines and with the approval of the Institute's Animal Care and Use Committee, and followed NIH guidelines. Male, CD-1 mice (6-week-old) were purchased from Charles River laboratories, fed on a standard diet and with tap water ad libitum for two weeks. Environmental conditions were standardized, including a room temperature of 21° C. and 12 hours artificial lighting. Mice were fasted 12 hrs before use.

Endotoxic shock was induced in the mice by administering a single intraperitoneal dose of lipopolysaccharide/D-(+/−) Glactosomine (Sigma, St. Louis, Mo.) (LPS/GalN) (20 μg/700 mg/kg) in saline. To test whether DM has protective effects on septic shock, varying concentrations (6.25, 12.5 and 25 mg/kg) of DM were injected into the mice subcutaneously 30 min before, and 2, and 4 hr after the injection of LPS/GalN. Control mice received the same amount of saline. At different time points, the animals were killed, and serum and liver samples were collected.

To examine the therapeutic effects of DM, animals were treated with 12.5 mg/ml DM at 30 min before LPS/GalN injection, and 30, 60 and 120 min after LPS/GalN administration. Serum ALT was measured to evaluate the therapeutic effects of the DM. Survival rate was evaluated within 12 hours after endotoxin administration.

Blood was collected from the eye while the mice were anesthetized, and then perfused with saline. Perfused liver samples were collected and frozen at −70° C. The blood samples were stored at 4° C. overnight and then centrifuged at 1500×g at 4° C. for 15 min. Serum was collected and stored at −70° C. for ALT, and TNFα ELISA assays. The frozen liver samples were homogenized in 10 mg/ml cold lysis buffer (20 mM Tris, 0.25 M sucrose, 2 mM EDTA, 10 mM EGTA, 1% Triton X-100 and protein cocktail inhibitor), and then centrifuged at 35,000×g for 40 min. The supernatant was then collected for protein assay using BCA Protein Assay Reagent Kit (Prod# 23227, PIERCE), and ELISA for TNFα.

Serum alanine aminotransferase (ALT) activity was assayed as a marker of hepatocellular death using a commercially available kit (Infinite ALT, Sigma, St. Louis, Mo.). A portion of the liver was fixed in 10% neutral formalin, processed by standard histological techniques, stained with hematoxylin and eosin, and examined for morphological evidence of liver injury.

The levels of TNFα in the serum and liver were determined as in Example 1.

Kupffer cell samples were collected by anesthetizing the CD-1 mice with pentobarbital anesthesia [60 mg/kg intraperitoneally (i.p.)]. The abdomen of the animals was shaved and opened, the portal vein was cannulated and perfused with $Ca^{2+}$- and $Mg^{2+}$-free Hanks' balanced salt solution (HBSS) at 37° C. for 5 min at a flow rate of 13 ml/min. Subsequently, the liver was perfused with HBSS containing 0.05% collagenase IV (Sigma Chemical, St. Louis, Mo.) at 37° C. for 5 min. After the liver was digested, it was excised and cut into small pieces in collagenase buffer. The suspension was filtered through nylon gauze mesh, and the filtrate was centrifuged at 450×g for 10 min at 4° C. Cell pellets were resuspended in buffer, parenchymal cells were removed by centrifugation at 50×g for 3 min, and the nonparenchymal cell fraction was washed twice with buffer. Cells were centrifuged on a density cushion of 50% of Percoll (Pharmacia, Upsala, Sweden) at 1,000×g for 15 min, and the Kupffer cell fraction was collected and washed again with buffer. The viability of the cells was determined by tryptan blue exclusion at >90%. The cells were seeded onto 24-well culture plates and cultured in RPMI 1640 (GIBCO Laboratories Life Technologies, Grand Island, N.Y.) supplemented with 10% fetal bovine serum and antibiotics (100 U/ml penicillin G and 100 μg/ml streptomycin sulfate) at 37° C. with 5% $CO_2$. Non-adherent cells were removed after 2 hours by replacing media, and cells were cultured for 24 hours before the experiments.

The production of superoxide and intracellular ROS by the Kupffer cells were measured as in Example 5.

The survival rate of the mice at 12 hours post-LPS/GalN treatment are presented in Table 2.

TABLE 2

| Dextromethorphan (mg/kg) | Animal number (n) | Survived animal | Rate of survival (%) |
|---|---|---|---|
| 0 | 61 | 28 | 45.9 |
| 6.25 | 12 | 8 | 66.6 |
| 12.5 | 56 | 50 | 89.3 |
| 25 | 12 | 11 | 91.6 |

About 44% percent of animals in LPS/GalN alone group died within 12 hours of LPS/GalN challenge. Pretreatment with DM (25 and 12.5 mg/kg, i.c.) significantly increased the survival rate up to about 90% (11/12 and 50/56 mice survived). Even at the lower concentration (6.25 mg/kg, i.c.), DM pretreatment increased survival rate to 67%. This clearly shows that DM is effective in protecting LPS/GalN-induced lethal shock in mice. This effect was also observed with DM i.c. 30 min post LPS/GalN challenge.

Figure 16A:
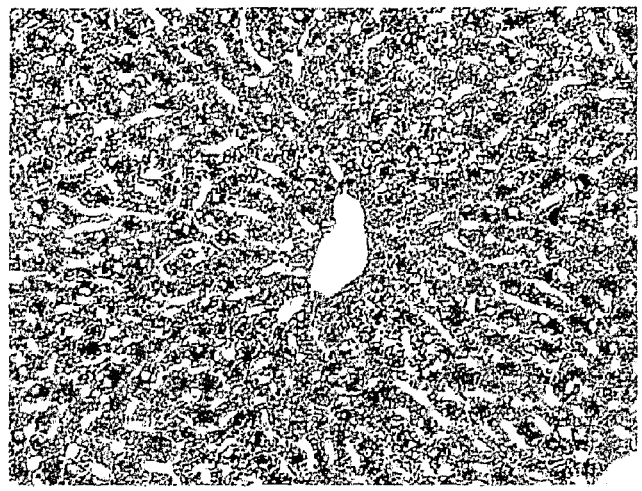
FIGS. 16A, 16B, and 16C are photomicrographs of a control mouse liver sample (FIG. 16A), a mouse liver sample 12 hours after LPS/galactosamine (GalN) treatment (FIG. 16B), and a mouse treated with DM plus LPS/g GalN (FIG. 16C).
Figure 16B:
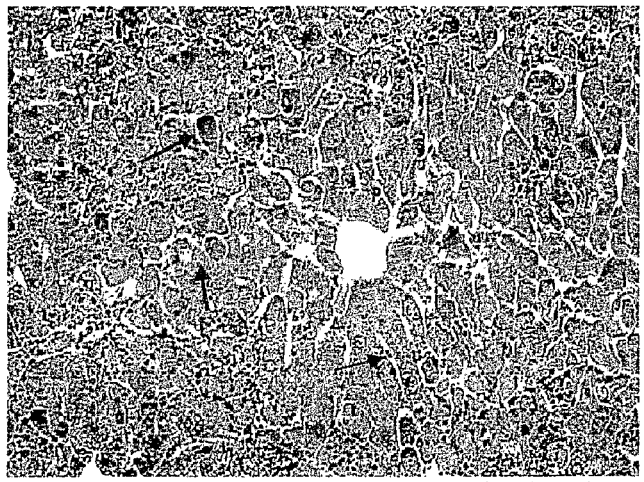
Figure 16C:
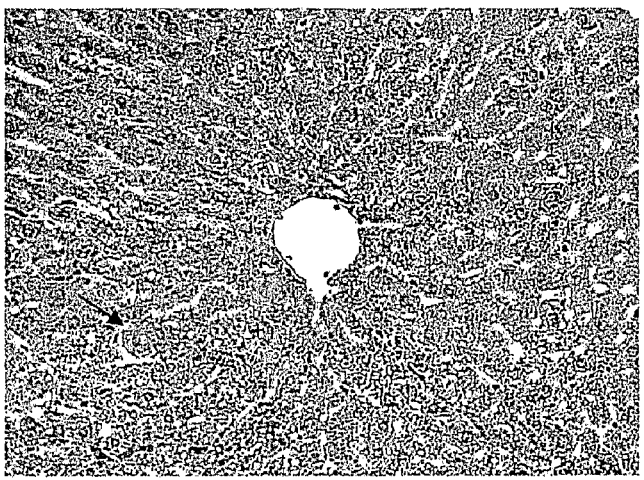

The liver samples collected from the LPS/GalN-induced mice are shown in FIGS. 16A (control), 16B (12 hours after LPS/GalN) and 16C (animal treated with DM). The liver histology was examined to evaluate the effect of DM treatment on LPS/GalN hepatotoxicity. In the LPS/GalN and saline treated mice, the liver sections showed apparently broad hemorrhagic necrosis and apoptosis, and severe hepatocyte swelling 12 hours after LPS/GalN challenge (FIG. 16B, arrows). These pathological alterations were dramatically ameliorated in the liver of animals receiving DM treatments (FIG. 16C). In the LPS/GalN plus DM-treated animals, hepatic congestion and hepatocellular necrosis were rare events.

Figure 17:
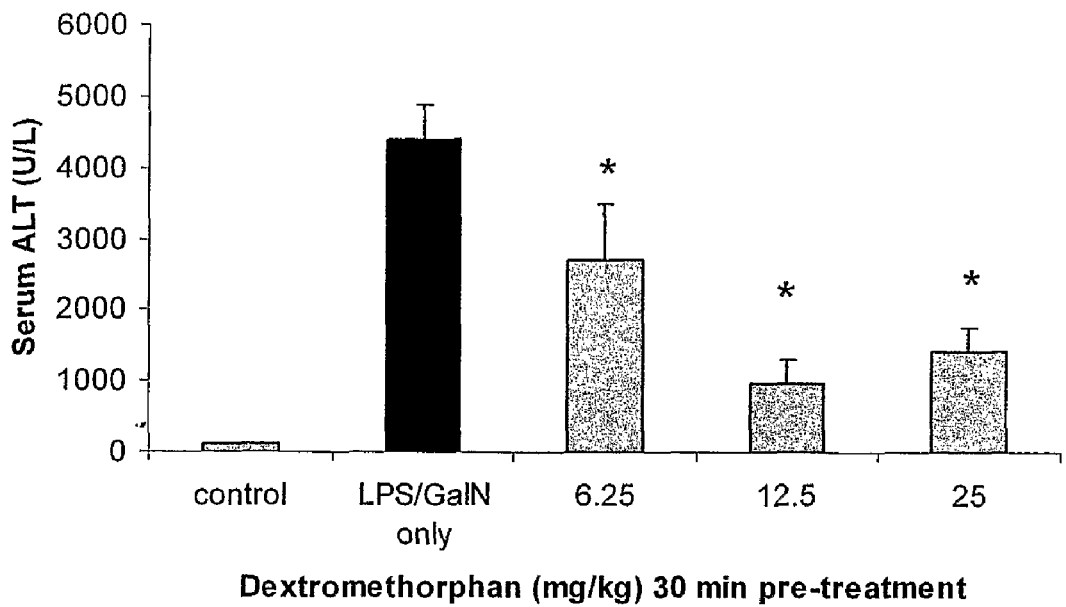
FIG. 17 is a graph showing the level of serum alanine aminotransferase (ALT) in CD-1 mice treated with different amounts of DM.
Figure 18:
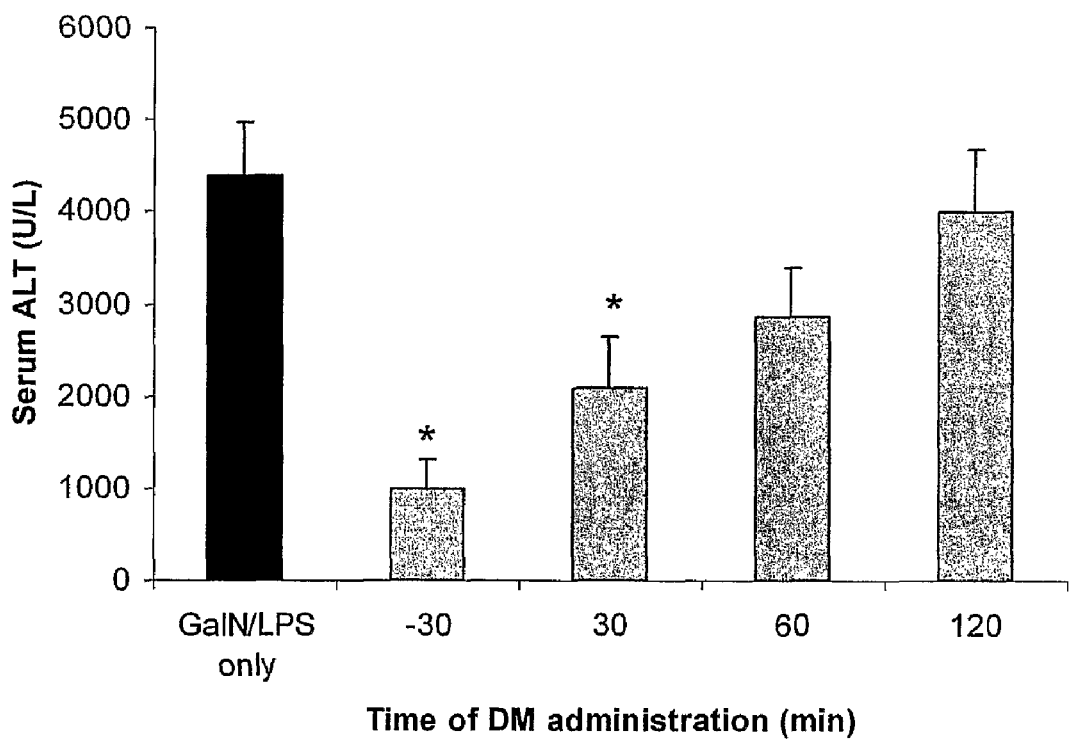
FIG. 18 is a graph showing the level of serum ALT at different times in CD-1 mice treated with DM.

Serum alanine aminotransferase (ALT), an indicator of acute hepatocellular death, was examined on DM treated mice to determine the protective effect of DM. Serum ALT increased ~35-fold over controls by 12 hrs after LPS/GalN administration (FIG. 17), DM dramatically decreased serum ALT level in a dose-dependent manner and reduced to about 25% of LPS/GalN group at 12.5 and 25 mg/kg of DM. Time-dependent reduction of serum ALT level is shown in FIG. 18, DM administrated at different time points, including 30 min pre-treatment and 30, 60, 120 min post-treatments shows protective effects to various extracts, the later the DM treatment, the less protective.

Figure 19A:
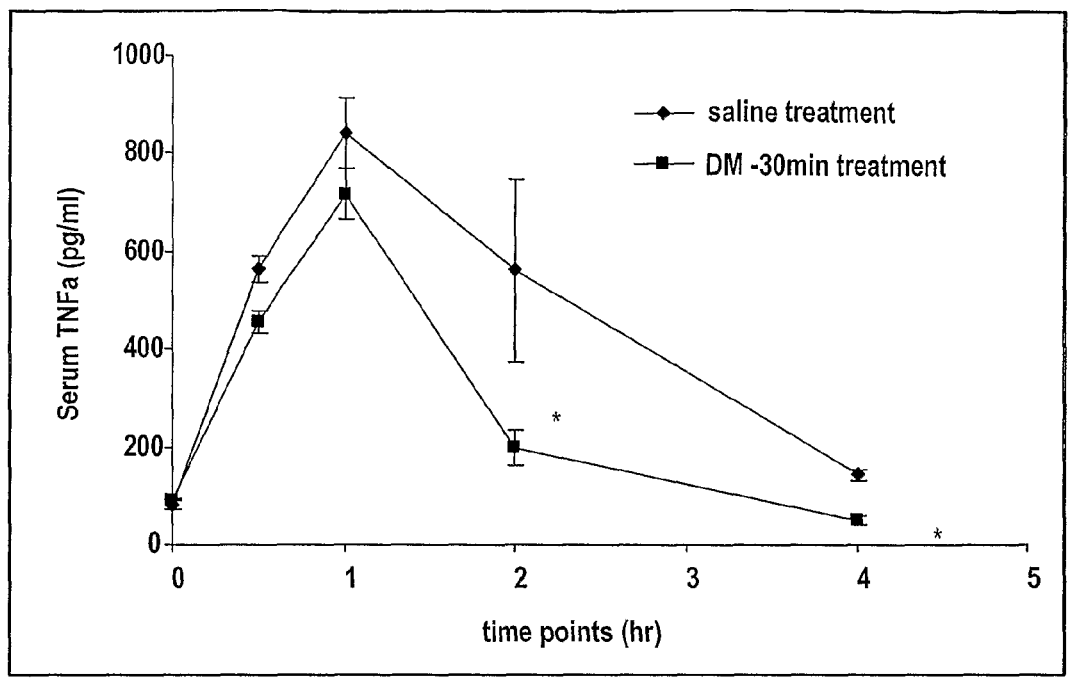
FIGS. 19A and 19B are graphs depicting serum TNFα (FIG. 19A) and liver TNFα (FIG. 19B) at subsequent times after LPS/GalN injection.
Figure 19B:
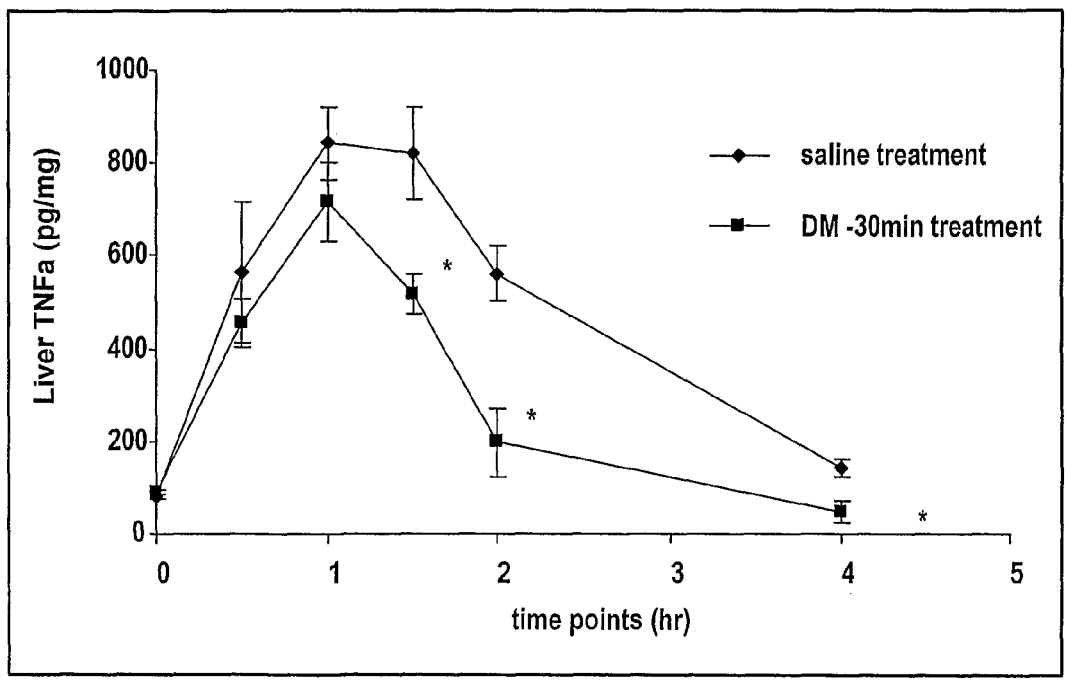

TNFα, an important factor that plays an important role in sepsis, was studied as a mechanism of the protective effect of DM in LPS/GalN-challenge mice. DM (12.5 mg/kg, i.c.) was administered to mice, followed by LPS/GalN challenge 30 min later. Serum and liver TNFα level was assessed using ELISA at the indicated time points. As shown in FIGS. 19A and 19B, DM significantly decreased TNFα level in both serum and liver at 1.5 and 2 hours after LPS/GalN challenge. The suppression of TNFα level was also found in DM 30 min post LPS/GalN treatment (data not shown). The reduction of hepatic TNFα paralleled the reduction of serum TNFα, indicating that decrease TNFα is an important mechanism of protection.

Activation of Kupffer cells by LPS is a critical event in the endotoxemia or sepsis. Therefore Kupffer cells were isolated to study the possible mechanism of DM in protection liver injury and sepsis. Endotoxin activates Kupffer cells to release inflammatory mediators such as free radicals and TNFα.

Figure 20A:
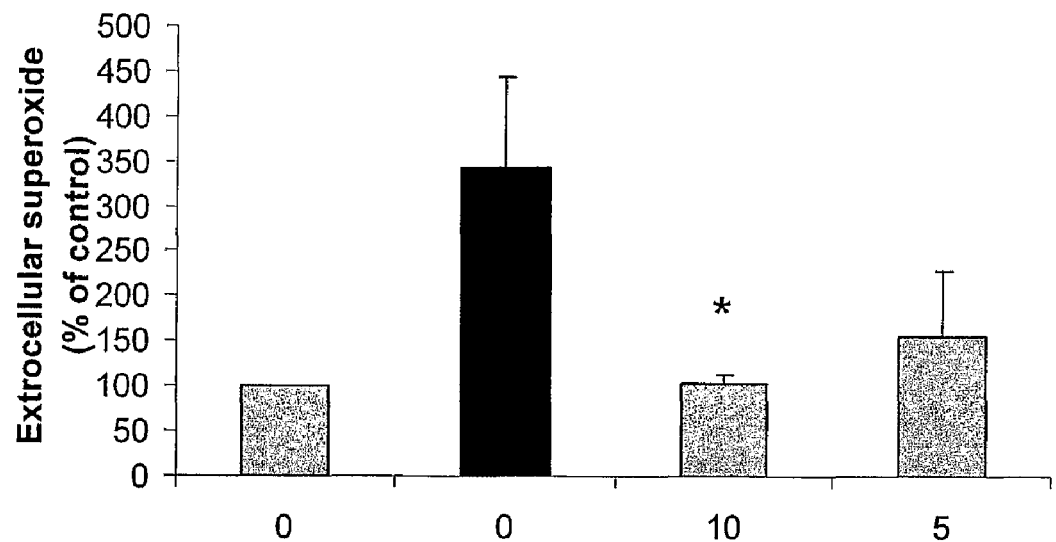
FIGS. 20A and 20B are graphs depicting extracellular superoxide (FIG. 20A) and iROS (FIG. 20B) in cells treated with various levels of DM.
Figure 20B:
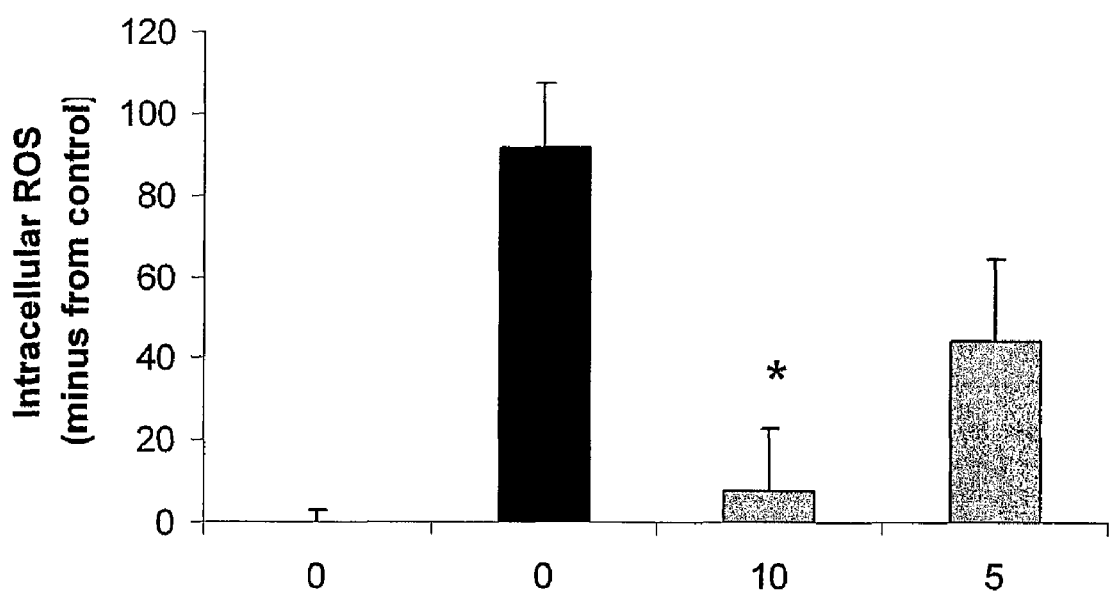

This study showed that both extracellular and intracellular superoxide production in CD-1 mouse Kupffer cells was increased significantly by LPS 10 ng/ml stimulation. This increase was significantly blunted by DM at dosage of 10 μM, and attenuated by 5 μM DM, as seen in FIGS. 20A and 20B.

Example 17

Gene Expression Studies

Total RNA was extracted from liver tissues (n=4 to 5) by Trizol reagent (Sigma, St. Louis, Mo.) and purified with an RNeasy column (Qiagen, Valencia, Calif.). Expression of the selected genes was quantified using real-time RT-PCR analysis that began by reverse transcribing the samples with MuLV reverse transcriptase and oligo-dT primers. The forward and reverse primers for the selected genes were designed using Primer Express software and are listed in Table 3.

TABLE 3

| Gene | Accession Number | Forward Primer | Reverse Primer |
| --- | --- | --- | --- |
| MIP-2 | NM_009140 | CCTCAACGGAA GAACCAAAGAG (Seq. ID No. 3) | CTCAGACAGCG AGGCACATC (Seq. ID No. 4) |
| TSP1 | M87276 | GCCGGATGACA AGTTCCAA (Seq. ID No. 5) | GCCTCAAGGAA GCCAAGAAGA (Seq. ID No. 6) |
| mKC | NM_008176 | TGGCTGGGATT CACCTCAAG (Seq. ID No. 7) | GTGGCTATGAC TTCGGTTTGG (Seq. ID No. 8) |
| ICAM-1 | NM_010493 | GTCTCGGAAGG GAGCCAAGTA (Seq. ID No. 9) | CGACGCCGCTC AGAAGAA (Seq. ID No. 10) |
| IL-6 | J03783 | GCCCACCAAGA ACGATAGTCA (Seq. ID No. 11) | GAAGGCAACTG GATGGAAGTCT (Seq. ID No. 12) |
| IL-10 | M37897 | CCAAGCCTTAT CGGAAATGATC (Seq. ID No. 13) | GATTTCTGGGC CATGCTTCTC (Seq. ID No. 14) |
| c-jun/AP-1 | J04115 | ACTCCGAGCTG GCATCCA (Seq. ID No. 15) | CCCACTGTTAA CGTGGTTCATG (Seq. ID No. 16) |
| c-myc | X01023 | CGCCGCTGGGA AACTTT (Seq. ID No. 17) | TCCTGGCTCGC AGATTGTAA (Seq. ID No. 18) |
| GADD45 | L28177 | CAGATCCATTT CACCCTCATCC (Seq. ID No. 19) | TCCAGTAGCAG CAGCTCAGC (Seq. ID No. 20) |
| GADD153 | X67083 | CTCCTGTCTGT CTCTCCGGAA (Seq. ID No. 21) | TACCCTCAGTC CCCTCCTCA (Seq. ID No. 22) |
| beta-actin | M12481 | GTATGACTCCA CTCACGGCAAA (Seq. ID No. 23) | GGTCTCGCTCC TGGAAGATG (Seq. ID No. 24) |

Abbreviation are: MIP-2, Macrophage Inflammatory Protein-2; TSP-1, thrombospondin1; mKC, a mouse CXC chemokine; ICAM-1, Intercellular Cell Adhesion Molecule-1; IL-6, Interleukin-6; IL-10, Interleukin-10; GADD153, Growth Arrest and DNA Damage inducible protein 153; GADD45, Growth Arrest and DNA Damage inducible protein 45.

The SYBR green DNA PCR kit (Applied Biosystems, Foster City, Calif.) was used for real-time PCR analysis. The relative differences in expression between groups were expressed using cycle time (Ct) values and the relative differences between groups were expressed as relative increases setting control as 100%. Assuming that the Ct value is reflective of the initial starting copy and that there is 100% efficacy, a difference of one cycle is equivalent to a two-fold difference in starting copy.

The results of the gene expression studies can be seen in Table 4 below.

TABLE 4

| | Control | LPS/GalN alone | LPS/Cont | LPS + DM | LPS + DM/Cont |
|---|---|---|---|---|---|
| Inflammatory Markers | | | | | |
| MIP-2 | 1.0 ± 0.3 | 153.3 ± 6.4 | 153.3 | 39.0 ± 2.1* | 39.0 |
| Thrombospondin-1 | 1.0 ± 0.1 | 94.2 ± 2.5 | 94.2 | 56.0 ± 1.57* | 56.0 |
| mKC | 1.0 ± 0.2 | 13.7 ± 2.9 | 13.7 | 5.8 ± 1.6* | 5.8 |
| ICAM-1 | 1.0 ± 0.1 | 8.45 ± 1.3 | 8.45 | 5.05 ± 2.7* | 5.05 |
| IL-6 | 1.0 ± 0.2 | 153.4 ± 13.3 | 153.4 | 43.6 ± 6.3* | 43.6 |
| IL-10 | 1.0 ± 0.1 | 25.3 ± 2.9 | 25.3 | 15.0 ± 3.3* | 15 |
| AcutePhase Protein genes & Cell-Death Markers | | | | | |
| c-jun/AP-1 | 1.0 ± 0.1 | 28.0 ± 7.5 | 28.0 | 9.1 ± 0.8* | 9.1 |
| c-myc | 1.0 ± 0.07 | 45.4 ± 3.6 | 45.4 | 18.4 ± 2.1* | 18.4 |
| GADD45 | 1.0 ± 0.2 | 24.6 ± 12.4 | 24.6 | 5.3 ± 2.4* | 5.3 |
| GADD153 | 1.0 ± 0.1 | 7.4 ± 0.3 | 7.4 | 2.7 ± 1.3* | 2.7 |

Mice were given GalN/LPS (700 mg/20 μg/kg, ip), or GalN/LPS + DM (12.5 mg/kg, sc, x2). Liver samples were taken at 12 hr after GalN/LPS administration, and total RNA was isolated for real-time RT-PCR analysis. In each individual sample, the expression level of each gene was first normalized with that of β-actin and then the relative differences between groups were expressed as relative increases setting controls as 1.0. Data represent means ± SE of n = 4-5 animals per group.
*P < 0.05 (compared to GalN/LPS alone.) Gene abbreviations are listed in Table 3.

As shown in Table 4, 12 hrs after GalN/LPS, there were dramatic increases in the expression of mouse macrophage inflammatory protein (MIP-2, 153.3-fold), thrombospondin-1 (TSP1, 94.2-fold), mouse chemokine (mKC, 13.7-fold), intracellular adhesion molecule-1 (ICAM-1, 8.45-fold), interleukin-6 (IL-6, 153.4-fold), and interleukin-10 (IL-10, 25.3-fold) genes. DM significantly diminished the GalN/LPS-induced enhanced expression for the MIP-2, TSP1, mKC, ICAM-1, IL-6 and IL-10 genes.

GalN/LPS acute hepatotoxicity also greatly enhanced the expression of c-jun/AP-1 (28-fold), c-myc (45.4-fold), while the expression of both genes was diminished to 9.1- and 18.4-fold, respectively with DM treatment. As a result of GalN/LPS toxicity, the DNA damage responsible proteins such as GADD45 and GADD153 were also increased by 24.6 and 7.4-fold respectively. There was a significant suppression of GalN/LPS-induced GADD45 and GADD153 protein genes by DM to 5.3 and 2.7-fold respectively.

Example 18

In Vitro Effects of DM on Septic Shock

Figure 21:
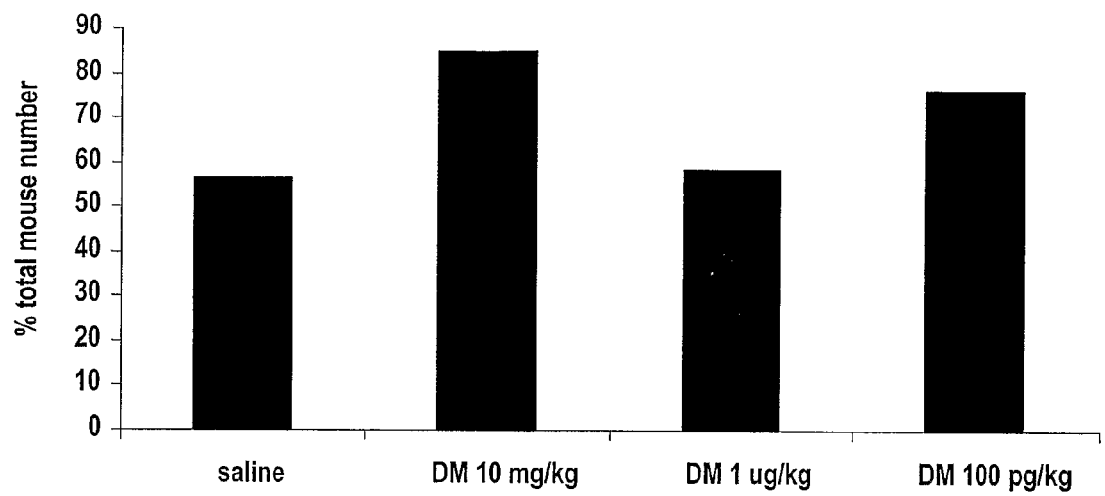
FIG. 21 is a graph showing the survival rate of another group of CD-1 mice given LPS/GalN and various amounts of DM.

Endotoxic shock were induced in mice in the same was as Example 16. The mice were given LPS/GalN (20 μg/700 mg/kg, ip) with or without the administration of DM (10 mg/kg, 1 μg/kg and 100 pg/kg, s.c.) 30 min before LPS/GalN. The survival rate of the animals was evaluated 12 hrs after LPS/GalN treatment. The results are shown in Table 5 below and are displayed in FIG. 21.

TABLE 5

| Amount of dextromethorphan administered | Number of animals in group | No. of animals survived | Rate of survival % |
|---|---|---|---|
| 0 | 30 | 17 | 56.7 |
| 10 mg/kg | 26 | 22 | 84.6 |
| 1 ug/kg | 17 | 10 | 58.8 |
| 100 pg/kg | 47 | 36 | 76.6 |

Figure 22:
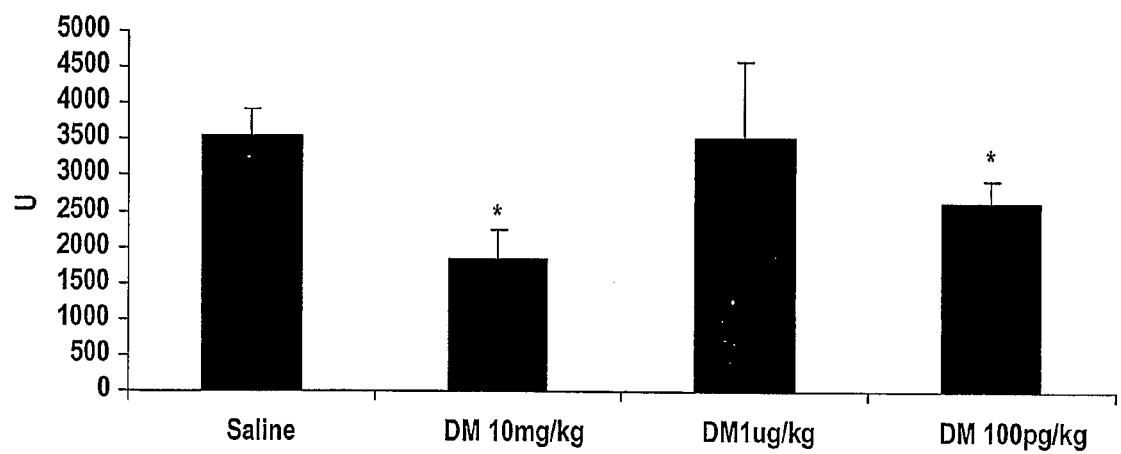
FIG. 22 is a graph showing the levels of serum ALT in the group of CD-1 mice from FIG. 21.

FIG. 22 shows the levels of serum ALT, measured as in Example 16.

Figure 23A:
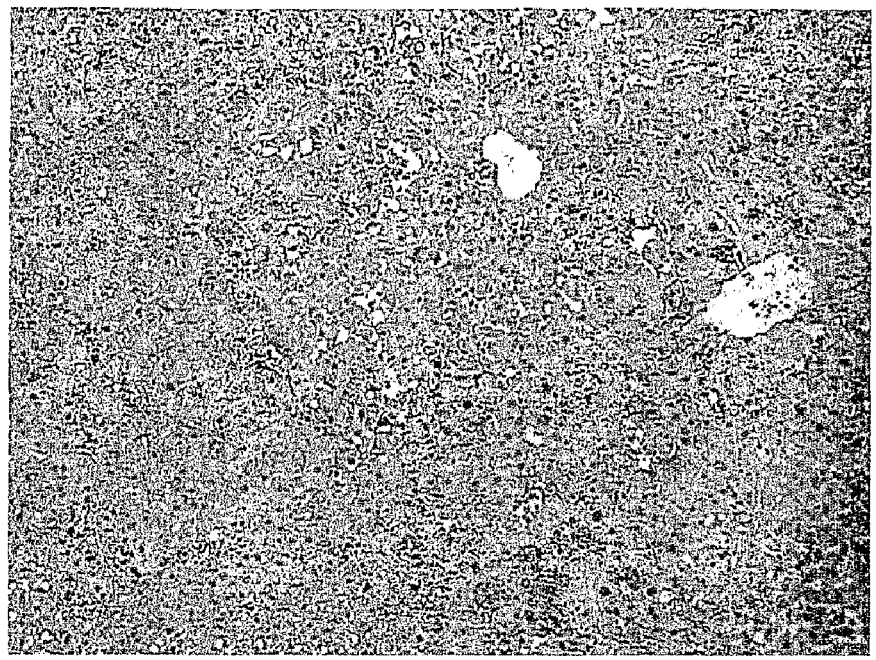
FIGS. 23A, 23B, 23C, and 23D are photomicrographs of a mouse liver sample treated with LPS/GalN alone (FIG. 23A), a mouse liver sample treated with 10 mg/kg DM plus LPS/GalN (FIG. 23B), a mouse liver sample treated with 1 µg/kg DM plus LPS/GalN (FIG. 23C), and a mouse liver sample treated with 100 pg/kg DM plus LPS/GalN (FIG. 23D).
Figure 23B:
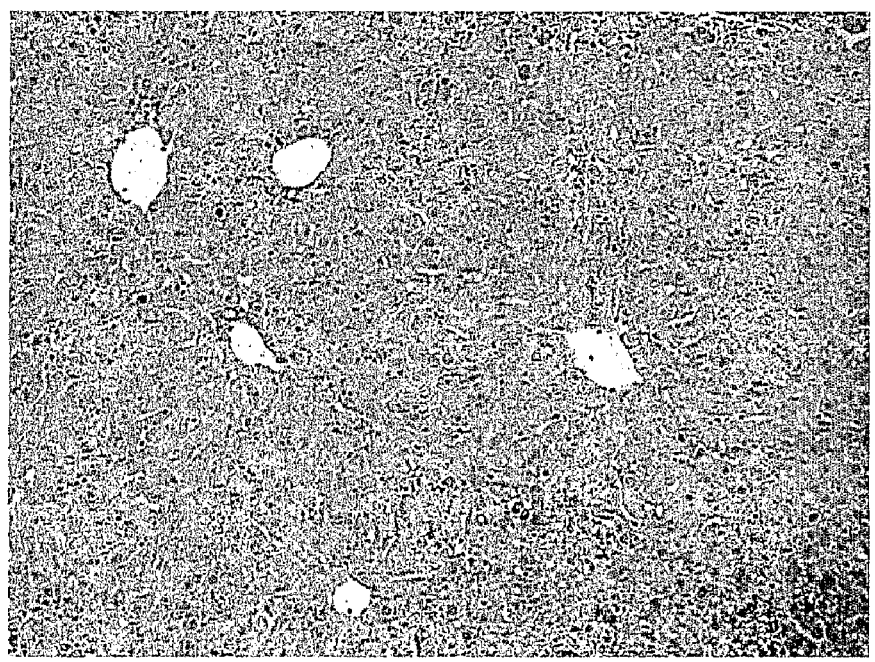
Figure 23C:
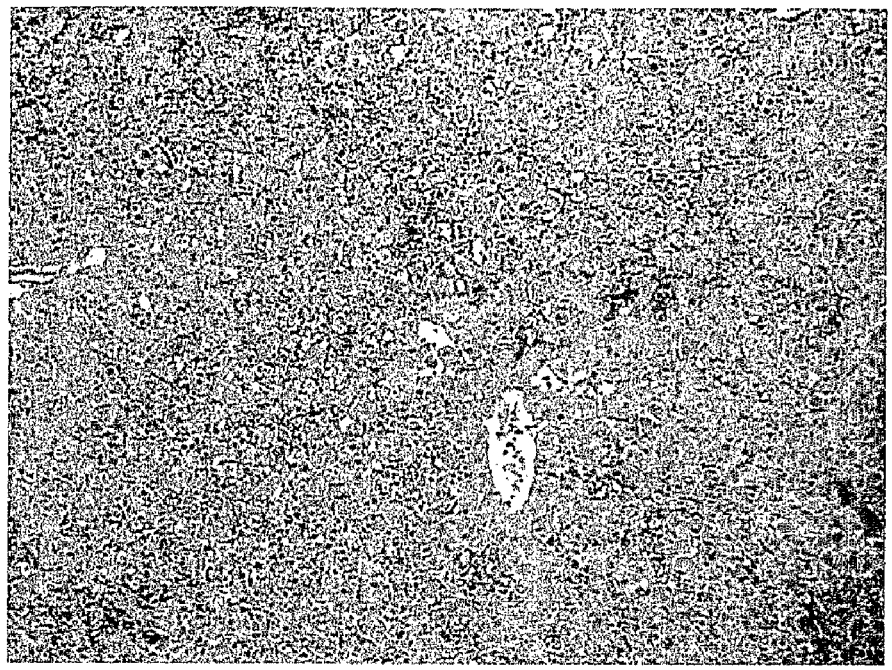
Figure 23D:
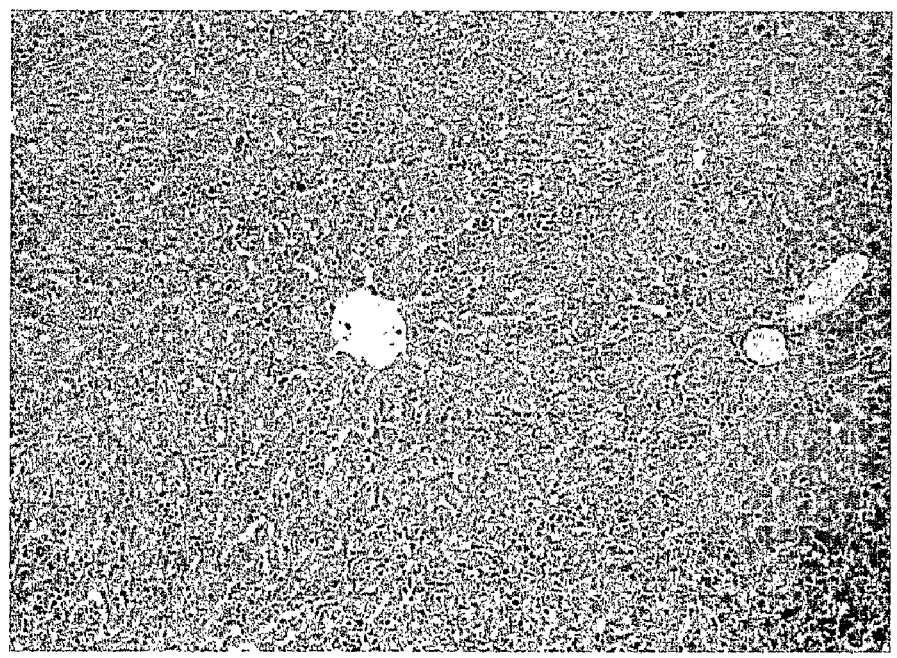

Sections of the mice livers were stained with hematoxylin and eosin, and photomicrographs were taken at 100× magnification. FIG. 23A shows a photomicrograph of a liver sample with LPS/GalN alone. As seen there, there is a foci of necrotic parenchymal cells, cell swelling, and congestion. FIG. 23B shows a photomicrograph of a liver sample that was administered 10 mg/kg DM plus LPS/GalN. As seen there, hepatic congestion and cell death are mild, while the cell swelling is the only notable lesion. FIG. 23C shows a photomicrograph of a liver sample with that was administered 1 μg/kg DM plus LPS/GalN. As seen there, hepatic congestion and cell death are obvious. FIG. 23D shows a photomicrograph of a liver sample that was administered 100 pg/kg DM plus LPS/GalN. As seen there, cell swelling is the only notable lesion, but cell death is mild.

Figure 24:
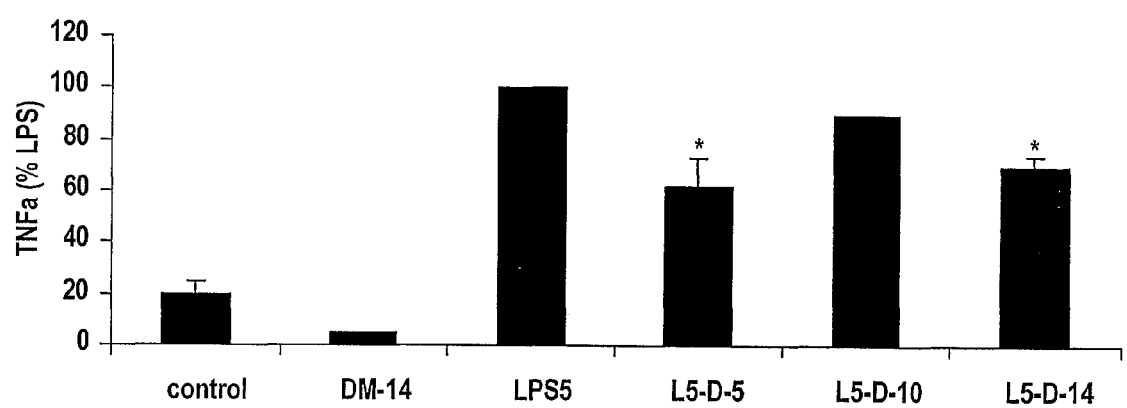
FIG. 24 is a graph showing TNFα production in Kupffer cells of CD-1 mice.

Kupffer cells were pre-treated with DM ($10^{-5}$, $10^{-10}$ or $10^{-14}$ M) or vehicle (control or LPS treated group) for 30 min, and then stimulated with LPS 5 ng/ml or vehicle (control group). TNF-α production (6 hrs after LPS stimulation) was measured by an ELISA kit as in Example 5. The data, which are seen in FIG. 24 are the mean ±SEM of 3-4 individual experiments with triplicates. *, Significantly different from LPS alone treated culture, P<0.05.

Action of VPA in Model of Inflammation-Mediated Dopaminergic Neurodegeneration

Examples 19 through 22 show VPA protects dopaminergic neurons from LPS-induced neurotoxicity through the inhibition of microglial activation. The anti-inflammatory responses of cultures stimulated with LPS and pretreated with VPA are also characterized.

Statistical Analysis: The data were presented as the mean ±S.E.M. For multiple comparisons of groups, ANOVA was used. Statistical significance between groups was assessed by paired or unpaired Student's t-test, with Bonferroni's correction. A value of p<0.05 was considered statistically significant.

Example 19

Effect of VPA on LPS-Induced Degeneration of Dopaminergic Neurons

Figure 25:
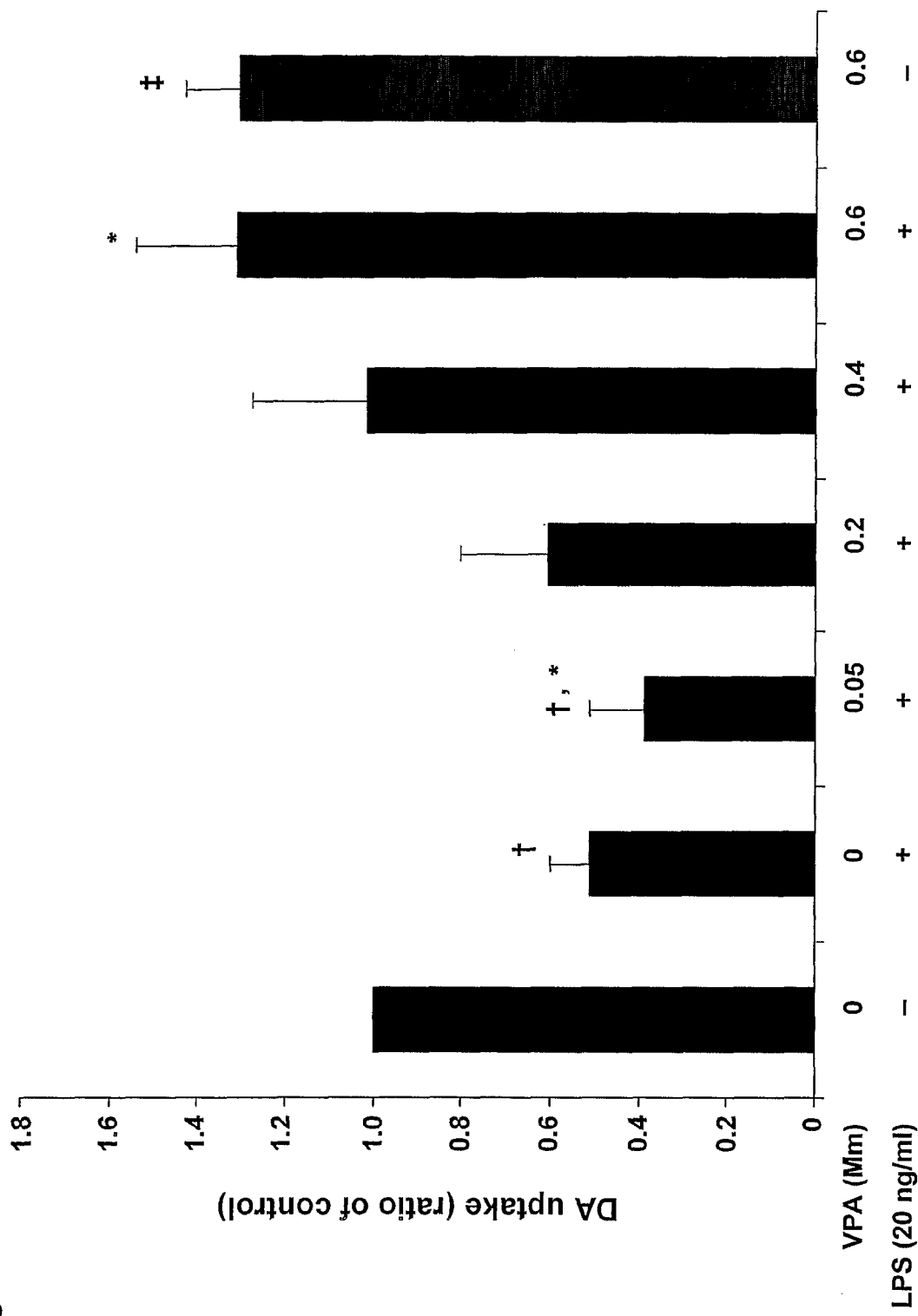
FIG. 25 depicts DA uptake as a percentage of control of neuron-glia cultures pretreated with various concentrations of valproic acid (VPA) followed by treatment with LPS (*, $p<0.05$ compared with LPS-treated cultures; †, $p<0.05$, ‡, $p<0.01$, compared with untreated control).

The effect of concentration-dependent VPA pretreatment on LPS-induced neurotoxicity in dopaminergic neurons in rat primary mesencephalic neuron-glia cultures is shown in FIG. 25. Neuron-glia cultures were prepared from the ventral mesencephalic tissues of embryonic day 13-14 rats. Dissociated cells were seeded at 1×10⁵/well and 5×10⁵/well to poly-D-lysine-coated 96-well and 24-well plates, respectively. Cells were maintained at 37° C. in a humidified atmosphere of 5% $CO_2$ and 95% air, in minimal essential medium (MEM) containing 10% fetal bovine serum, 10% horse serum, 1 gm/l glucose, 2 mM L-glutamine, 1 mM sodium pyruvate, 100 μM non-essential amino acids, 50 U/ml penicillin, and 50 μg/ml streptomycin. At the time of treatment of 6-day old cultures, the medium was changed to 2% MEM (2% fetal bovine and horse serum in MEM) and the cultures were then pretreated with vehicle or the indicated concentration (0.05, 0.2, 0.4 and 0.6 mM) of VPA (Sigma-Aldrich, St. Louis, Mo., which was freshly prepared with culture medium. Two days later, cells were treated with 20 ng/ml LPS 3 days and followed by the assay of [³H]DA uptake. [3H]DA uptake assays were performed as described above in Example 1.

Degeneration of dopaminergic neurons was assessed by measuring the ability of cultures to take up [3H]DA, or counting the number of TH-ir neurons after immunostaining (see below). The [³H]DA uptake assay showed that LPS treatment reduced the capacity of the cultures to take up DA to approximately 50% of the vehicle control and this LPS-induced reduction was concentration-dependently prevented by VPA pretreatment (FIG. 25). At 0.6 mM VPA, which is within the therapeutic range of this drug, the LPS-induced decrease in DA uptake was completely restored and VPA alone at this concentration did not affect DA uptake levels in the cultures.

Figure 26:
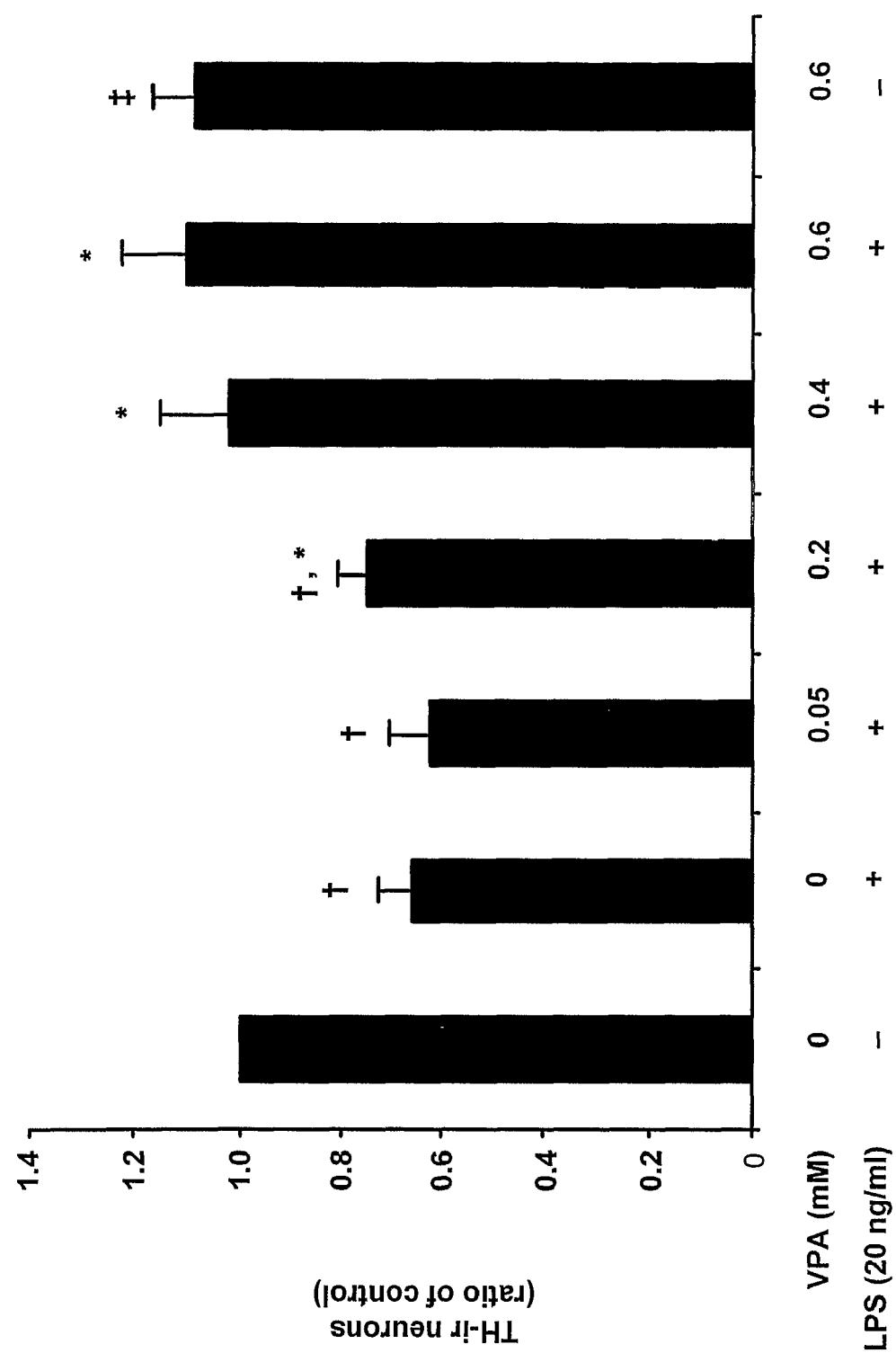
FIG. 26 is a graph illustrating the number of tyrosine hydroxylase (TH)-immunoreactive neurons after treatment with various concentrations of VPA followed by treatment with LPS (*, $p<0.05$ compared with LPS-treated cultures; †, $p<0.05$, ‡, $p<0.01$, compared with untreated control).

The effect of VPA pretreatment on morphological changes of mesencephalic dopaminergic neurons immunostained with anti-TH antibody were determined. The primary midbrain cultures were pretreated with the indicated concentrations of VPA for 48 h and then treated with 20 ng/ml LPS for 72 h, as described above. DA neurons were recognized with the anti-TH antibody and microglia were detected with the OX-42 antibody, which recognizes the CR3 receptor. Briefly, formaldehyde (3.7%)-fixed cultures were treated with 1% hydrogen peroxide (10 ml) followed by sequential incubation with blocking solution (30 min), primary antibody (overnight, 4° C.), biotinylated secondary antibody (2 h), and ABC reagents (40 min). Color was developed with 3,3'-diaminobenzidine. For morphological analysis, the images were recorded with an inverted microscope (Nikon, Tokyo, Japan) connected to a charge-coupled device camera (DAGE-MTI, Michigan City, Ind.) operated with MetaMorph software (Universal Imaging Corporation, Downingtown, Pa.). TH-ir neurons in each well of the 24-well plate were visually counted under the microscope at 400× magnification. The results are shown in FIG. 26. Images were recorded with an inverted microscope connected to a charge-coupled device camera. Scale bar, 25 μm.

Figure 27A:
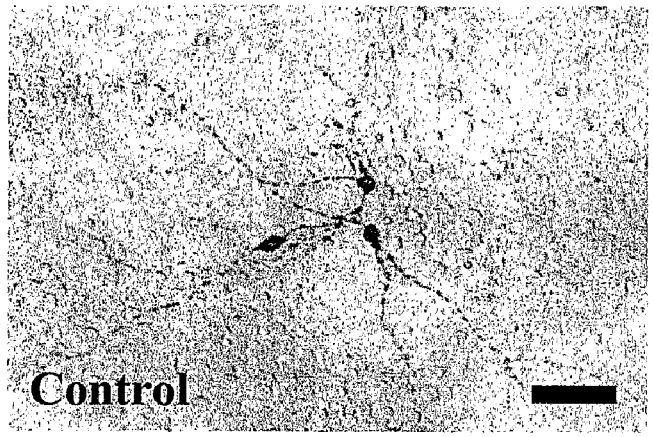
FIGS. 27A, 27B, 27C, 27D, 27E, and 27F are photomicrographs showing morphological features of neurons after incubation with vehicle (A); LPS, 20 ng/mL (B); 0.6 mM VPA (C); 0.2 mM VPA, 20 ng/mL LPS (D); 0.4 mM VPA, 20 ng/mL LPS (E); 0.6 mM VPA, 20 ng/mL LPS (F); for 7 days and then immunostaining. Scale bar, 25 μm.
Figure 27B:
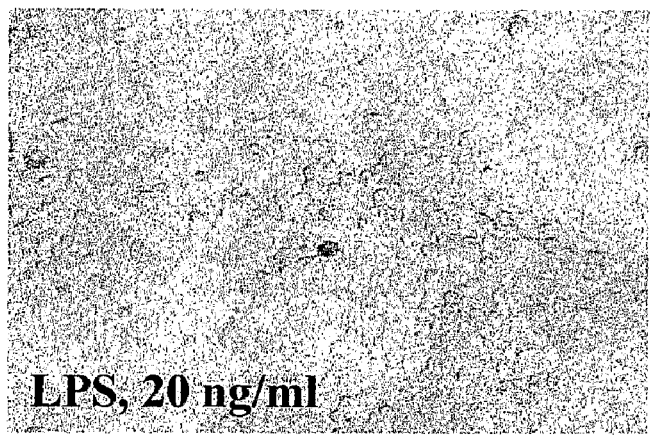
Figure 27C:
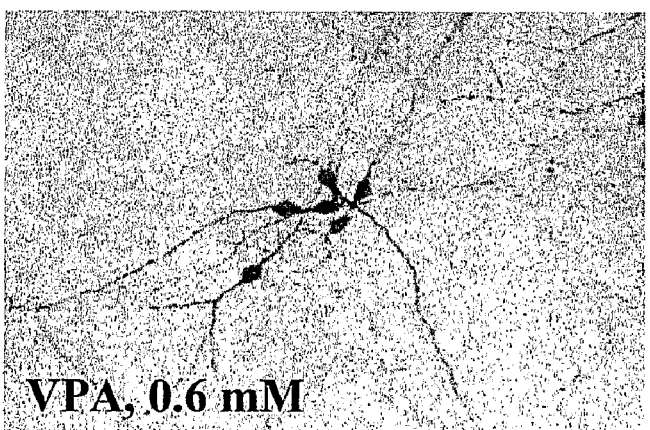
Figure 27D:
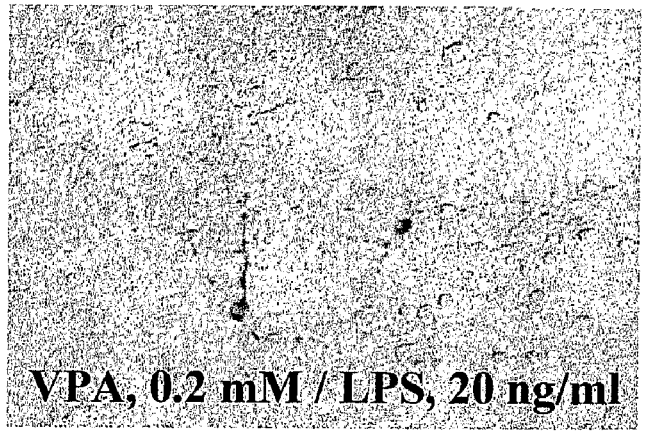
Figure 27E:
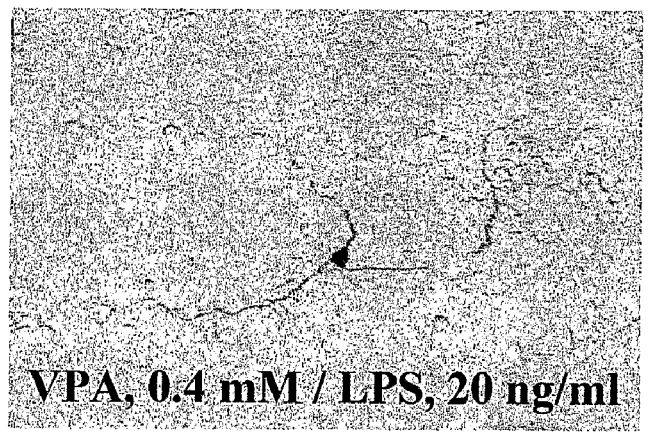
Figure 27F:
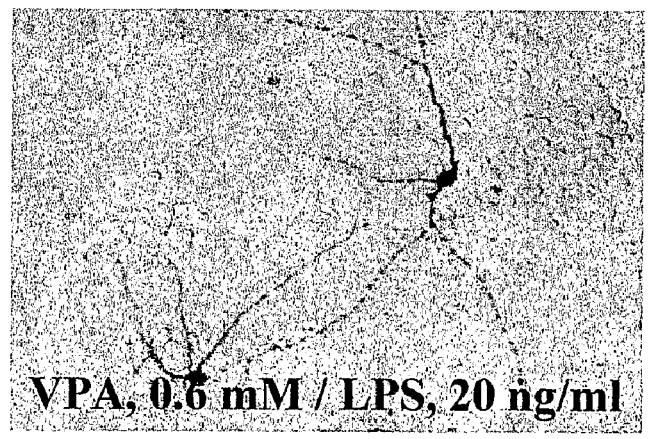

Morphological inspection revealed that LPS treatment not only decreased the number of TH-ir neurons, but also caused a loss of neuronal process (FIGS. 27A and 27B). These characteristics were reversed by VPA pretreatment in a dose-dependent manner (FIG. 27D-27F). LPS-induced loss of TH-ir neurons was prevented by VPA pretreatment in a concentration-dependent manner with a significant effect at 0.2, 0.4 and 0.6 mM. VPA at 0.6 mM, either alone or in conjunction with LPS, enhanced the TH immunostaining in both the cell bodies and neuronal processes compared with the vehicle control (FIGS. 27C and 27F).

Data are expressed as means ±S.E.M. from 4 independent experiments. *, $p<0.05$ compared with LPS-treated cultures; †, $p<0.05$, ‡, $p<0.01$, compared with untreated control.

Example 20

VPA Pretreatment Suppresses LPS-Induced Activation of Microglia And Production of Pro-Inflammatory Factors in Neuron-Glia Cultures FIGS. 28A-28F show VPA pretreatment suppresses LPS-induced microglia activation revealed by OX-42 immunostaining. Mesencephalic neuron-glia cultures were pretreated with VPA for 48 h and then treated with 20 ng/ml LPS for 72 h, as described in Example 19. Immunostaining with an antibody against OX-42 was then performed, as described in Example 19.

Figure 28A:
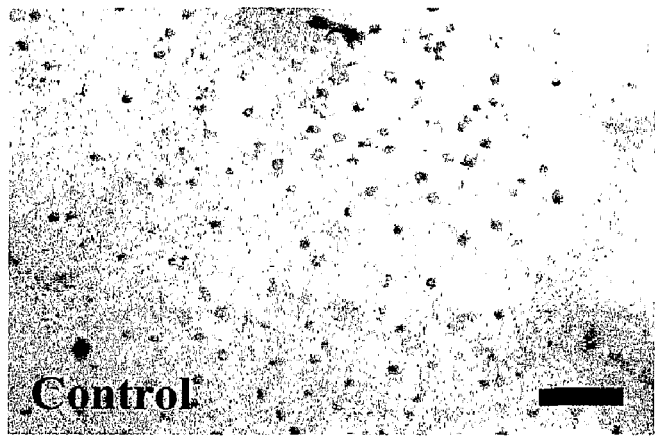
FIGS. 28A, 28B, 28C, 28D, 28E, and 28F are photomicrographs showing morphological features of neuron-enriched cultures treated as indicated and then immunostained. Scale bar, 100 μm.
Figure 28B:
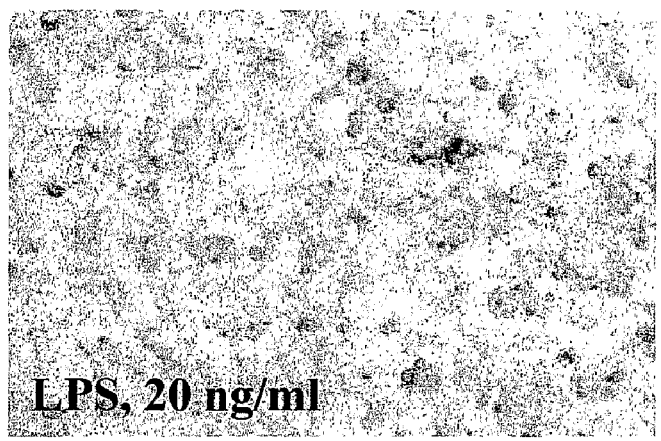
Figure 28C:
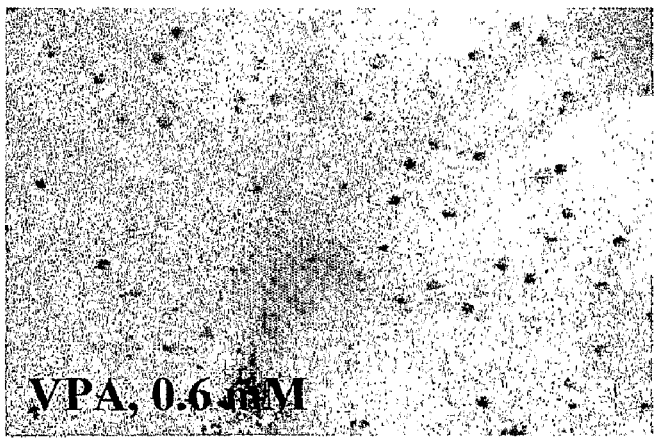
Figure 28D:
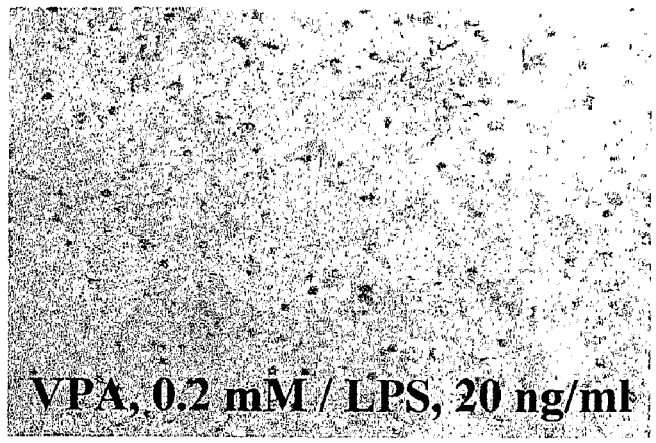
Figure 28E:
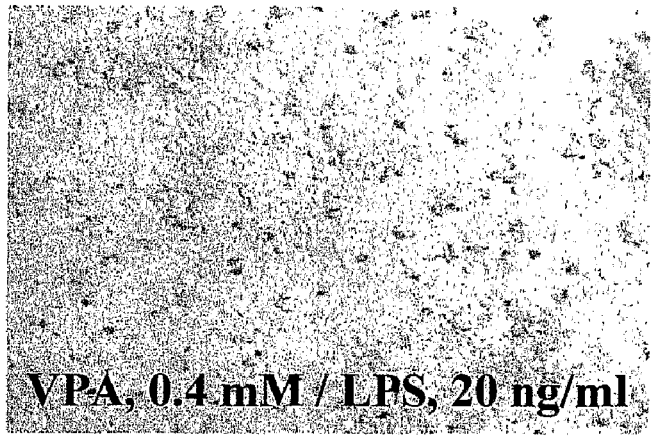
Figure 28F:
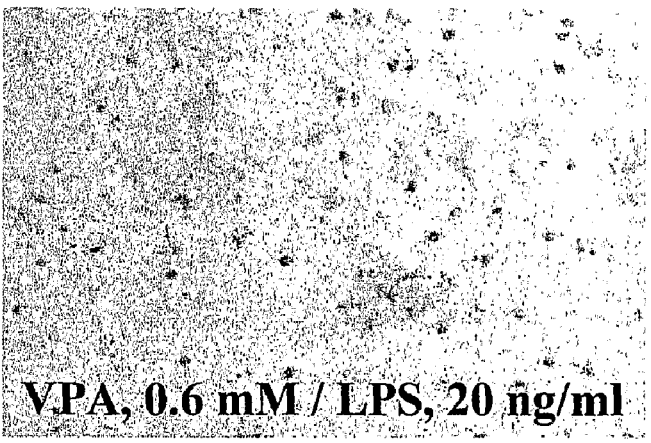

Mesencephalic neuron-glia cultures treated with LPS displayed the characteristics of activated microglia such as, increased cell size, irregular shape, and intensified OX-42 immunoreactivity, a specific marker for rat microglia as shown in FIGS. 28A and 28B. The LPS-stimulated activation of microglia was suppressed in neuron-glia cultures pretreated for 48 h with 0.4 or 0.6 mM VPA, as shown in FIGS. 28D through 28F. VPA alone did not show significant effects on microglia activation, as shown in FIG. 28C. Scale bar, 100 μm. The images shown are representative of 3 independent experiments.

Figure 29:
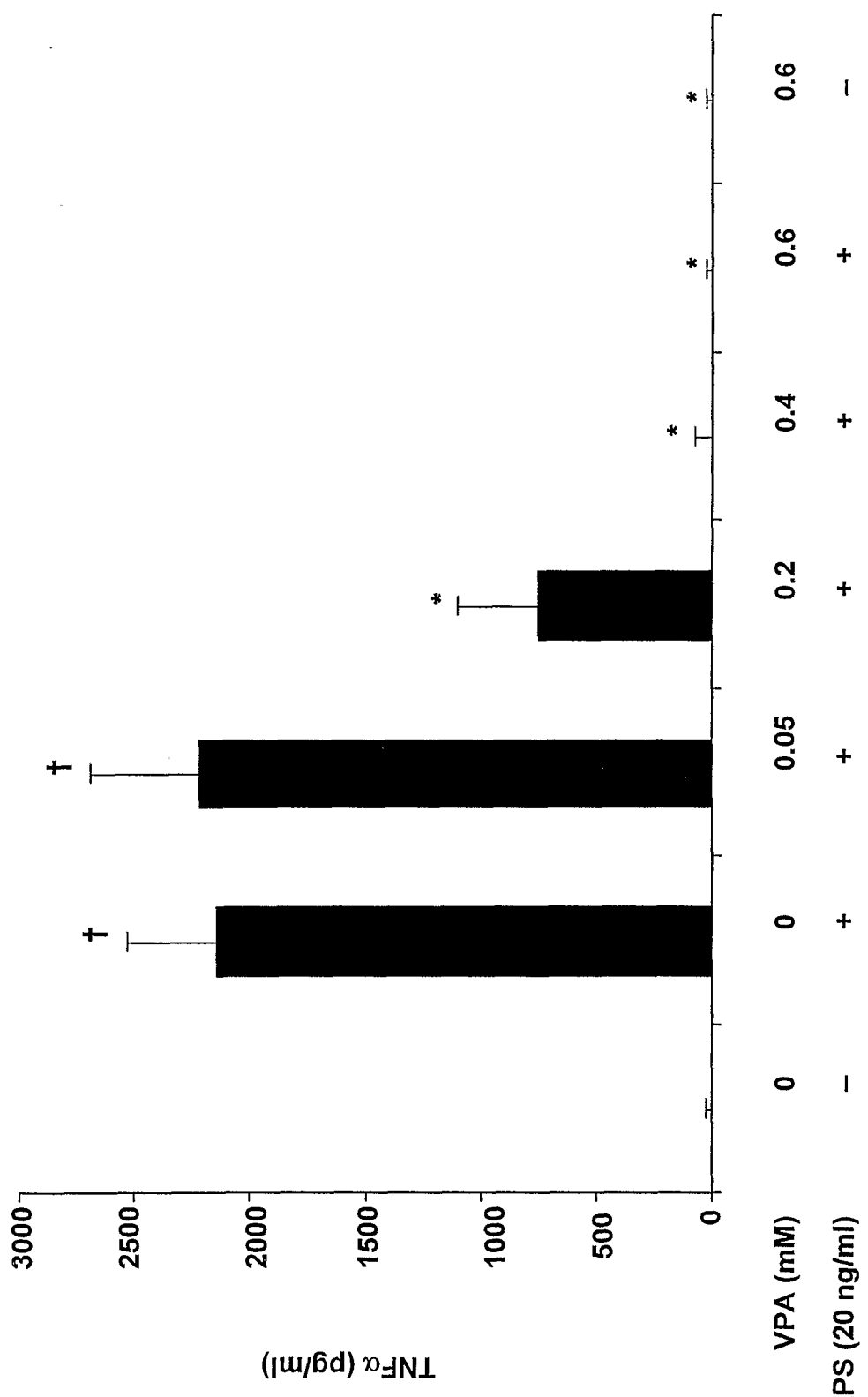
FIG. 29 is a graph showing release of TNFα determined 3 hours after LPS treatment.
Figure 30:
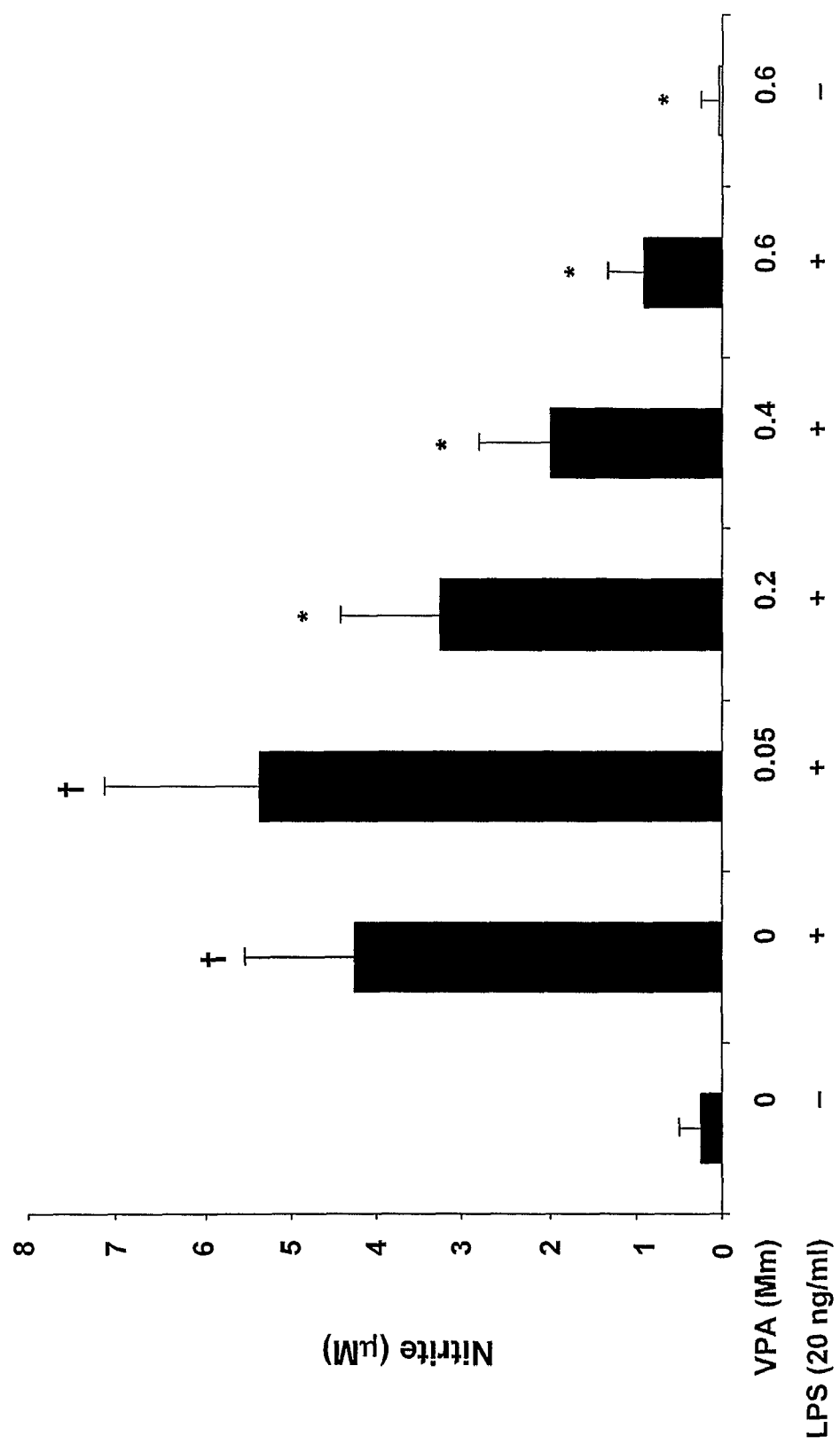
FIG. 30 is a graph showing levels of nitrite in the supernatant, an indicator of NO production, determined at 24 hours post LPS treatment.

Suppression of LPS-induced release of pro-inflammatory factors from rat primary midbrain cultures by VPA pretreatment is shown in FIGS. 29 and 30. Activation of microglia mediates the LPS-induced dopaminergic neurodegeneration. This process has been attributed, at least in part, to secretion of a variety of pro-inflammatory and neurotoxic factors, such as TNFα, NO, and superoxide.

Mesencephalic neuron-glia cultures were pretreated with VPA or vehicle control for 48 hours prior to stimulation with 20 ng/ml LPS. The release of TNF-α was determined 3 hours after LPS treatment. The release of TNFα was measured with a rat TNFα enzyme-linked immunosorbent assay kit from R & D System (Minneapolis, Minn.). As shown in FIG. 29, pretreatment with 0.4 or 0.6 mM VPA completely blocked LPS-induced production of TNFα in neuron-glia cultures determined at 3 h after LPS stimulation. Even at 0.2 mM VPA, LPS-induced TNFα production was also significant inhibited.

Production of nitric oxide (NO) was determined in the mesencephalic neuron-glia cultures, following pretreatment and LPS stimulation as described above, by measuring the accumulated levels of nitrite in the supernatant with Griess reagent. Accumulation of nitrite, an indicator of LPS-stimulated production of NO, was determined 24 after LPS stimulation. As shown in FIG. 30, pretreatment with 0.4 and 0.6 mM VPA reduced LPS-stimulated NO production 54% and 78% of the control, respectively.

Results are means ±S.E.M of 4 independent experiments. *, $p<0.05$ compared with LPS-treated cultures; †, $p<0.05$, compared with untreated control.

Example 21

VPA Pretreatment Inhibits LPS-Induced Intracellular Reactive Oxygen Species Production in Enriched Microglia To determine if VPA pretreatment protects dopaminergic neurons against intracellular oxidative stress, the level of intracellular reactive oxygen species (iROS) was measured via DCF oxidation in enriched microglia cultures.

Assay of intracellular ROS is performed as follows. 5-(and-6)-Chloromethyl-2',7'-dichlorodihydrofluorescein diacetate (CM-H2-DCFDA) (Molecular Probes, Eugene, Oreg.), a chloromethyl derivative of H2-DCFDA, passively diffuses into cells in which it is hydrolyzed by intracellular esterases to liberate 2'-7'-dichlorofluorescein (DCF) which, during reaction with oxidizing species, yields a highly fluorescent compound that is trapped inside the cell. Microglia-enriched cultures were prepared from the whole brains of 1-day-old rats as described in Example 1. Immunocytochemical analysis indicated that the cultures were 95-98% pure for microglia. Cells were seeded at $1 \times 10^5$/well in 96-well plates for one day followed by treatment with 0.6 mM or 1.2 mM VPA for 24 h. The cultures were used for the assay of intracellular ROS.

After washing two times with warm Hank's balanced salt solution (HBSS), CM-H2-DCFDA, diluted to a final concentration of 1 μM in phenol red-free HBSS, was added to cultures and incubated for 30 min at 37° C. Then cultures were added with 0.6 or 1.2 mM VPA in HBSS again for 30 min and followed the treatment with 100 ng/ml LPS for 2 hours at 37° C., fluorescence intensity was measured at 485 nm for excitation and 530 nm for emission using a SpectraMax Gemini XS fluorescence microplate reader (Molecular Devices, Sunnyvale, Calif.).

Figure 31:
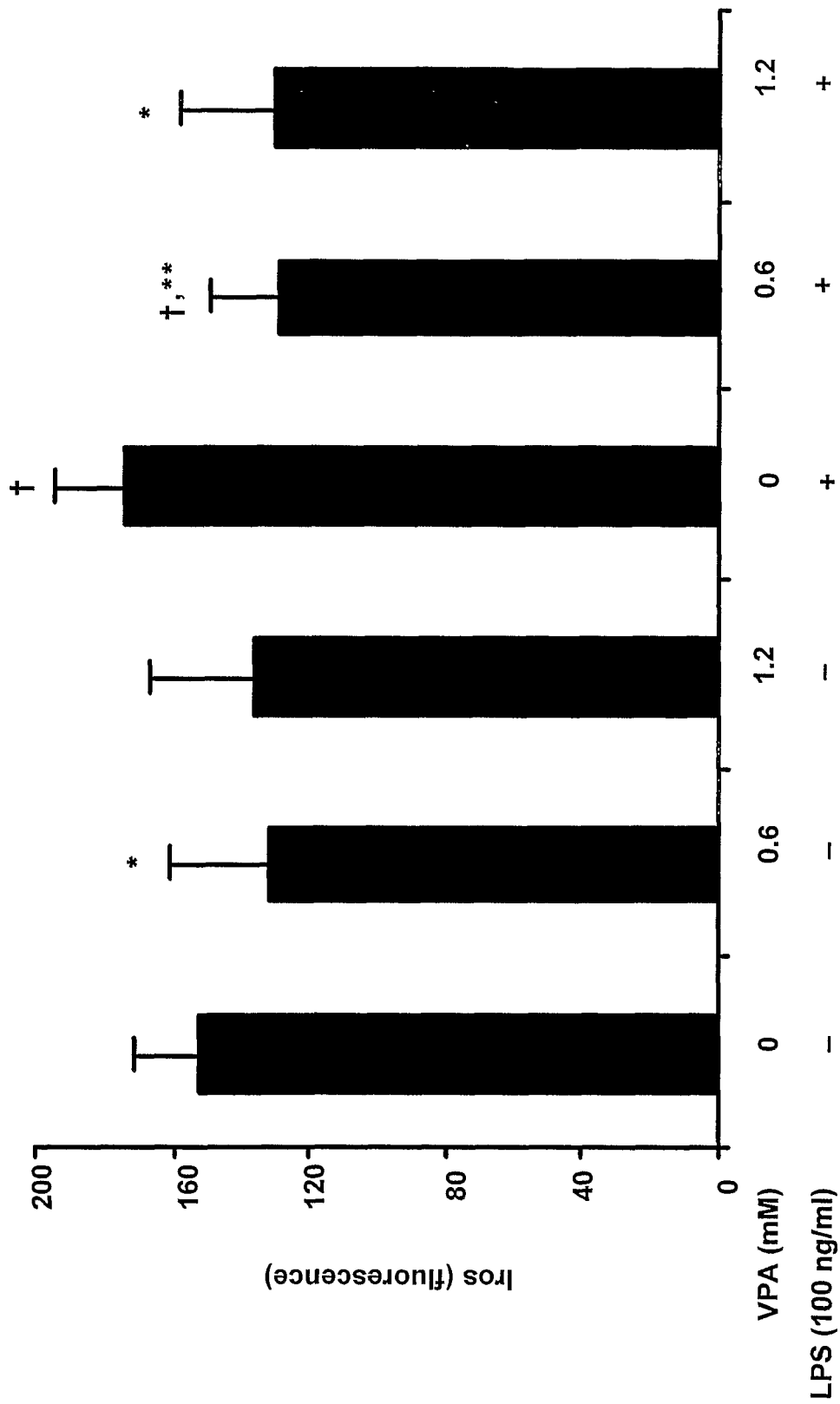
FIG. 31 is a graph showing levels of iROS in enriched microglia determined by DCFDA at 2 h after LPS treatment.
Figure 32A:
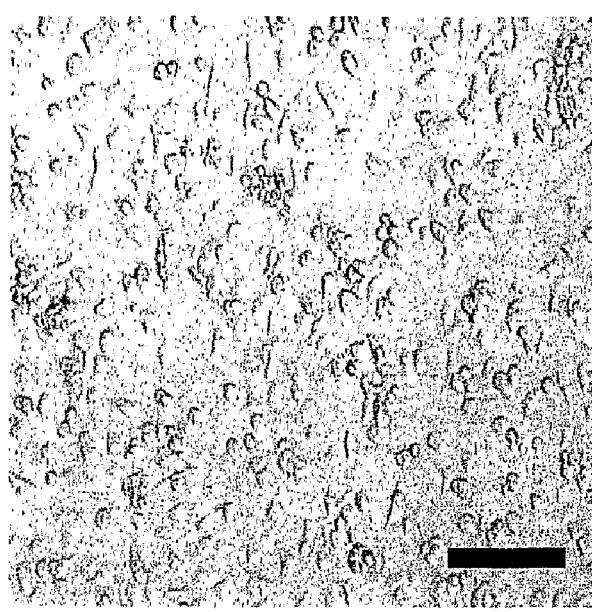
FIGS. 32A, 32B, 32C, 32D, 32E, and 32F are photomicrographs showing morphological features and number of microglia treated with VPA or vehicle for time indicated and then immunostained. Scale bar, 100 μm.
Figure 32B:
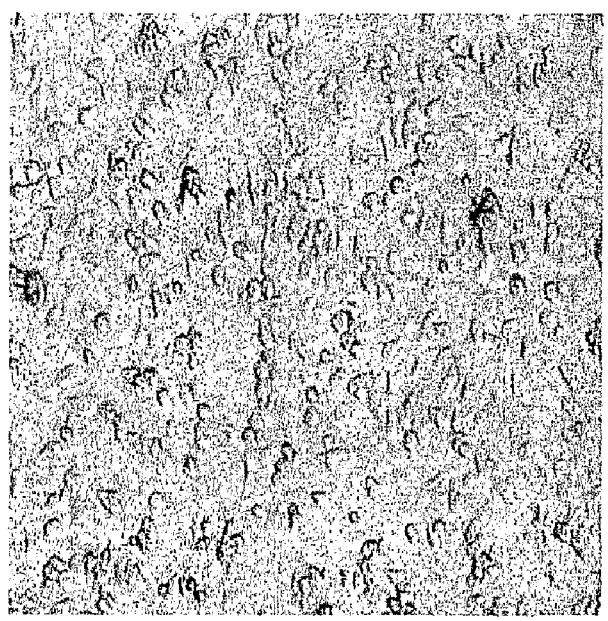
Figure 32C:
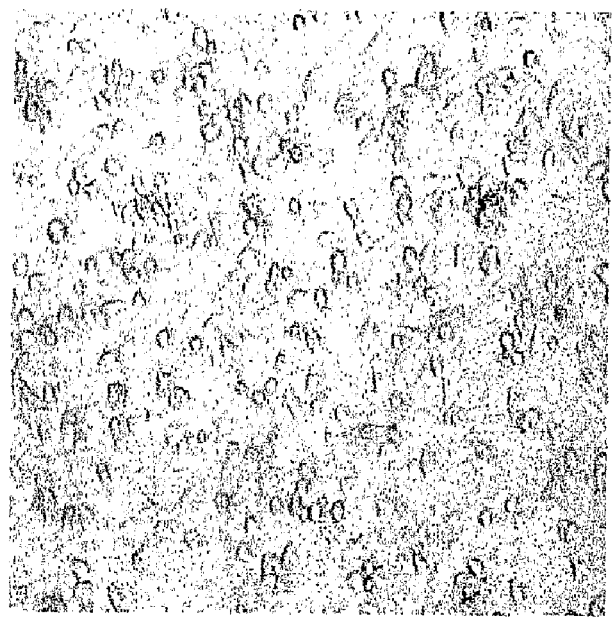
Figure 32D:
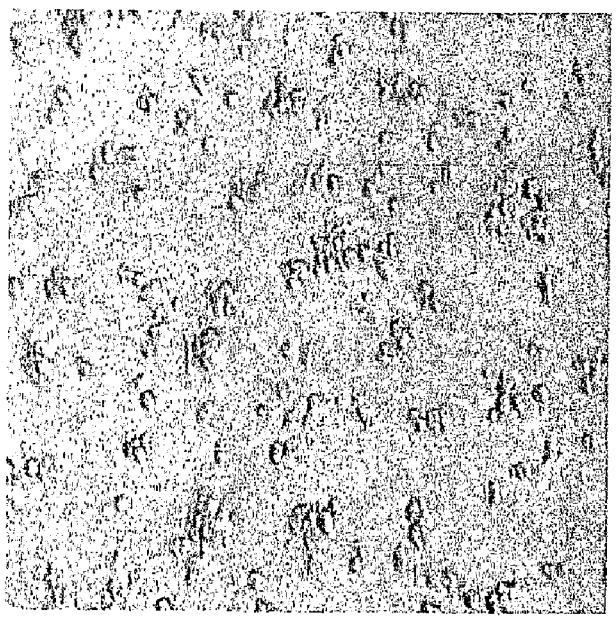
Figure 32E:
Figure 32F:
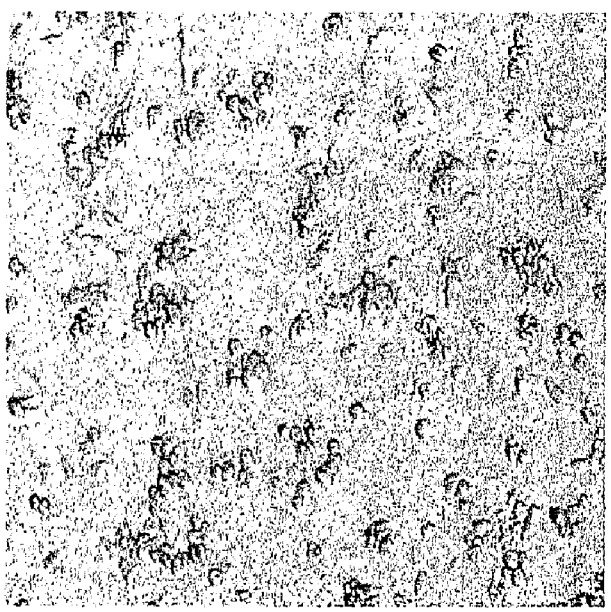
Figure 33:
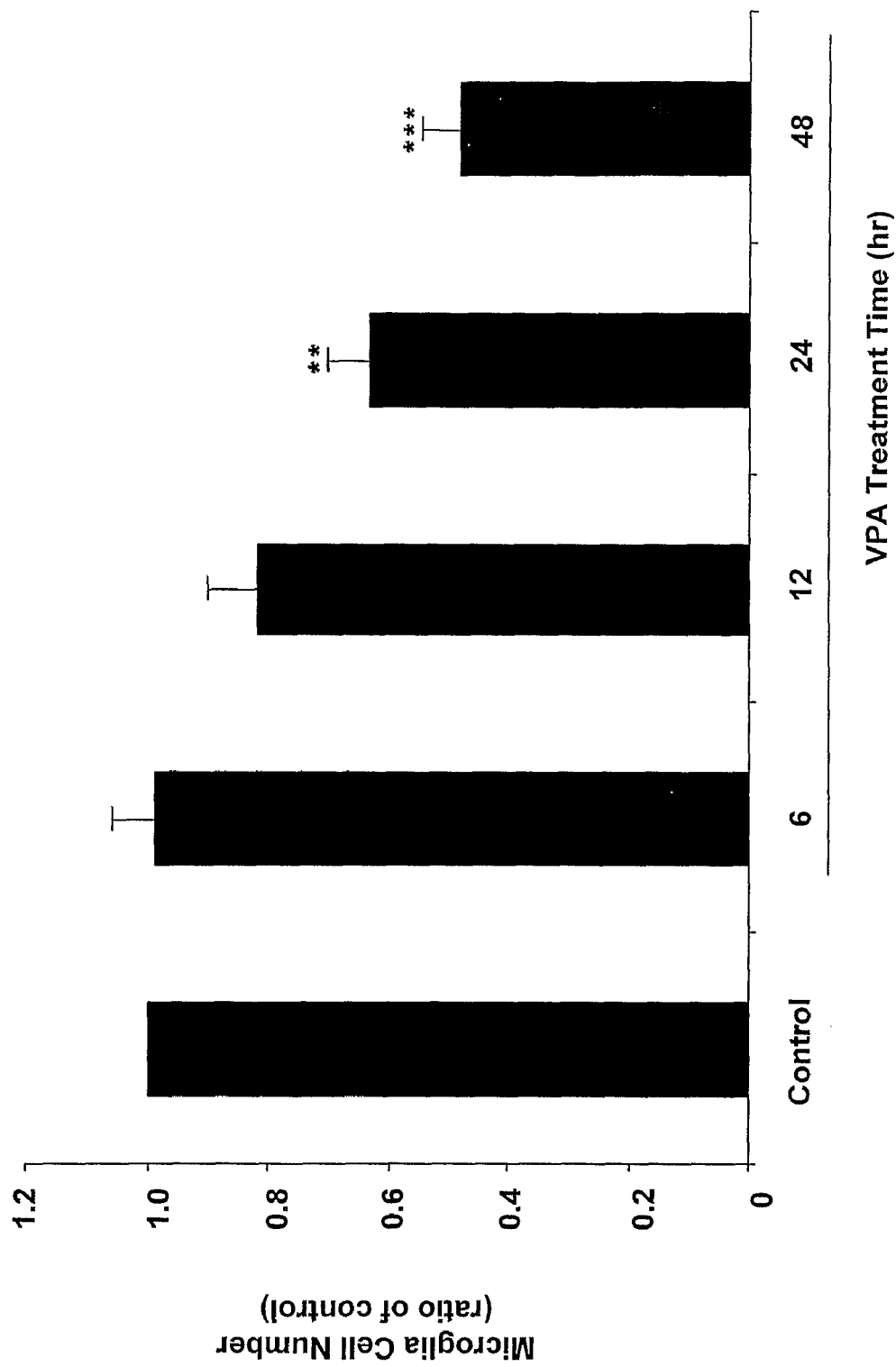
FIG. 33 is a graph showing number of surviving microglia after treatment with indicated concentrations of VPA.
Figure 34A:
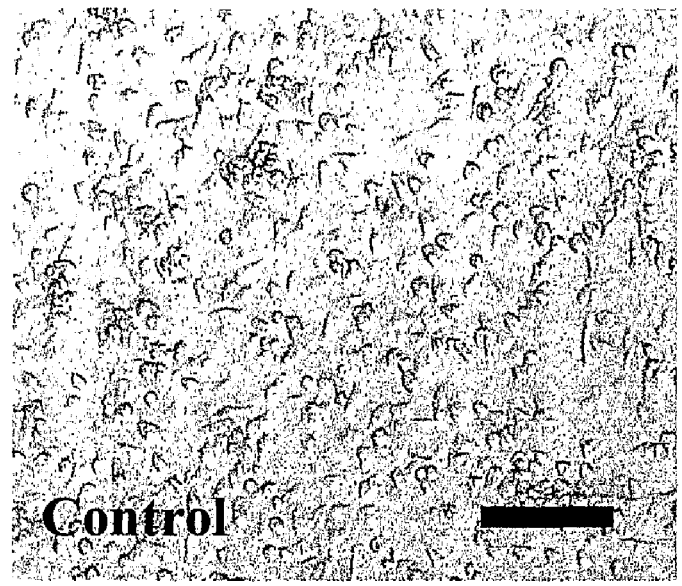
FIGS. 34A, 34B, 34C and 34D are photomicrographs showing morphological features and number of microglia treated as indicated and then immunostained. Scale bar, 100 μm. Scale bar, 100 μm.
Figure 34B:
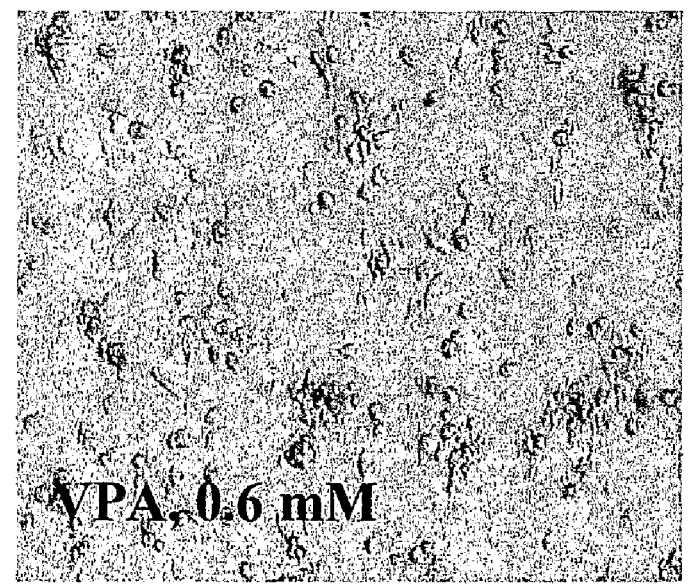
Figure 34C:
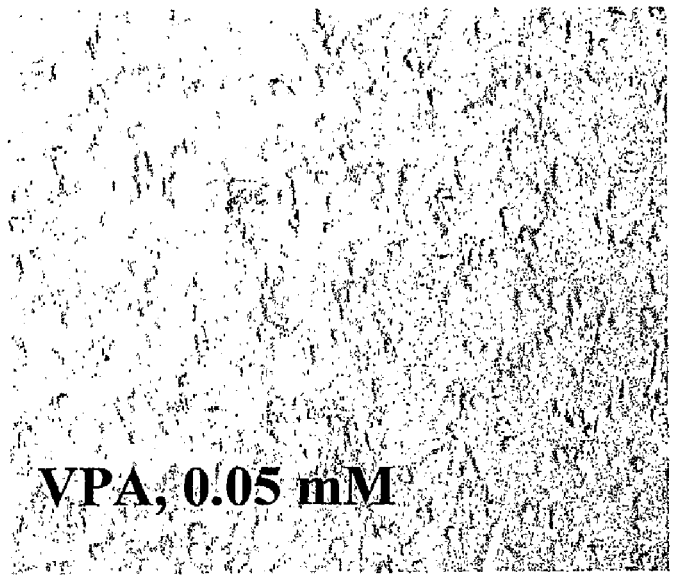
Figure 34D:
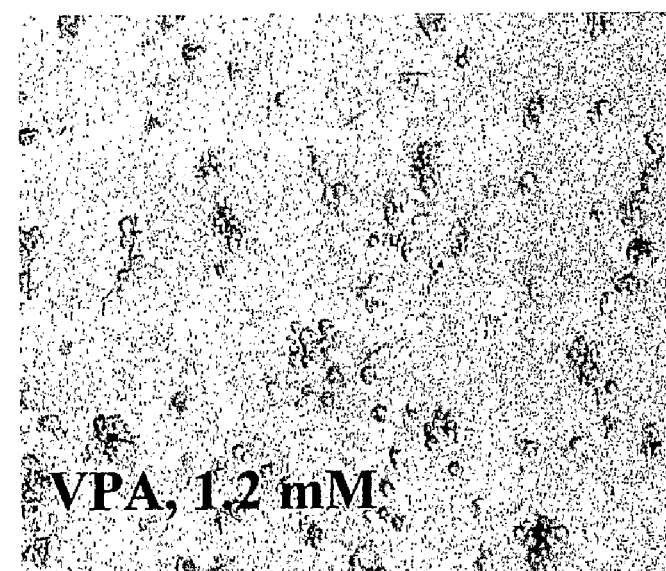
Figure 35:
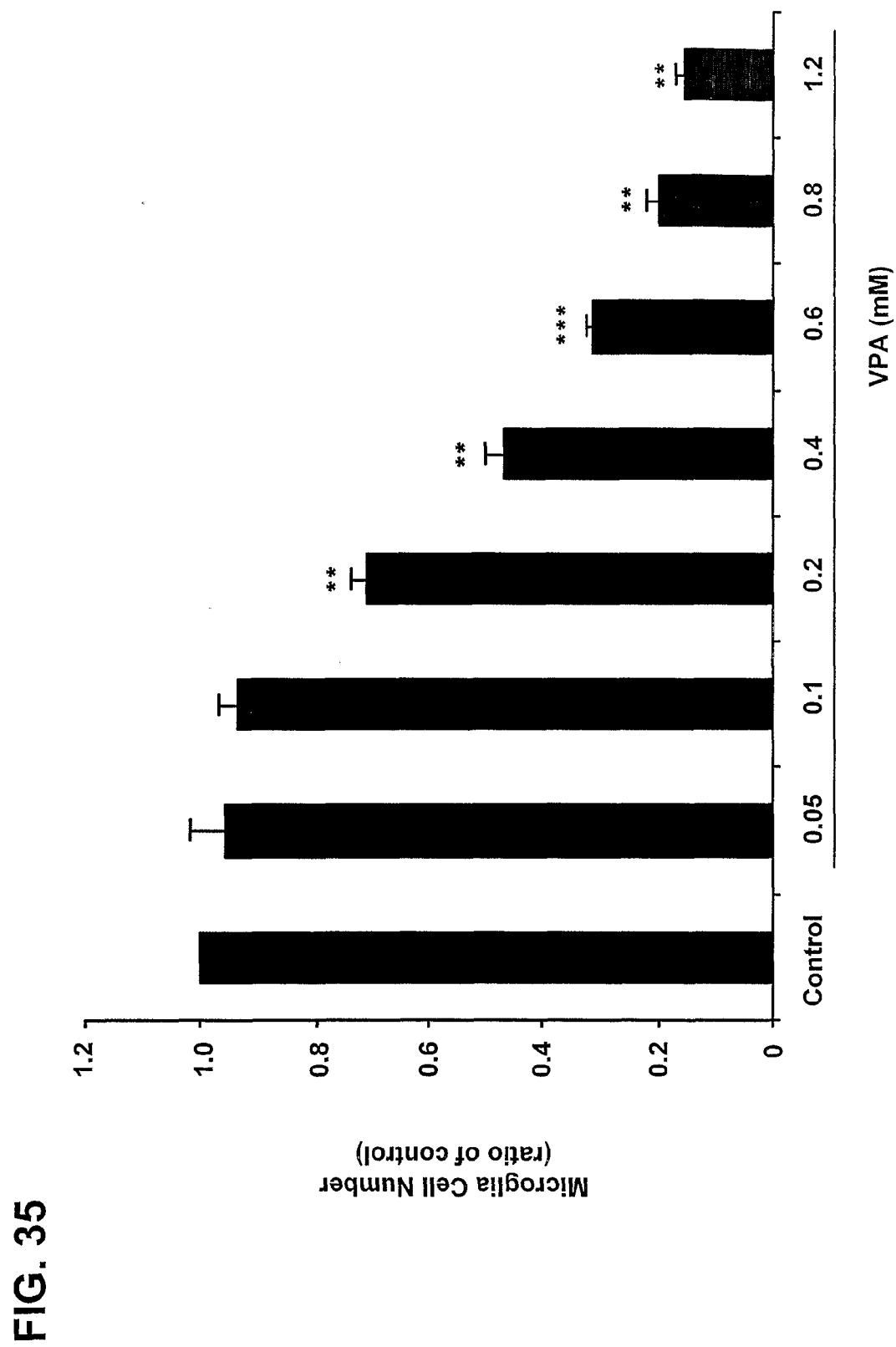
FIG. 35 is a graph showing number of surviving microglia after treatment with indicated concentrations of VPA.

The iROS level was significantly increased by LPS treatment and this increase was completely blocked by pretreatment with VPA at 0.6 or 1.2 mM (FIG. 31). VPA alone at 0.6 mM, but not 1.2 mM, also reduced basal iROS levels.

Example 22

VPA Treatment Decreases the Number of Microglia

Primary rat microglia-enriched cultures were used to determine if VPA treatment affected the total number of microglia. Microglia cell number was determined as follows. Primary microglia-enriched cultures were prepared from the whole brains of 1-day-old rats as described previously. After one day in vitro were treated with the indicated concentrations of VPA (0.05, 0.1, 0.2, 0.4, 0.6, 0.8, 1.0, or 1.2 mM) for 48 h, or with 0.6 mM VPA for different times (6, 12, 24 or 48 h). After treatment with VPA and vehicle for 48 hours, the number and morphology of microglia in cultures were observed under an inverted microscope (Nikon, Tokyo, Japan) at 100×. The total number of microglia was counted by using the CyQUANT cell proliferation assay kit (Molecular Probes, Inc.).

Microscopic examination showed that 0.6 mM VPA time-dependently decreased the number of microglia with a significant effect at 24 h and 48 h after treatment (FIGS. 32A-32F and 33). The VPA effect was also concentration-dependent with a robust decrease in microglia number in the dose range of 0.2 mM to 1.2 mM after 48 h treatment (FIGS. 34A-34D and 35). The loss of microglia was about 80% by treatment with 0.8 mM VPA. Moreover, VPA-induced microglia loss was time and dose-dependently associated with aggregations or clumping of surviving cells (FIGS. 32A-32F and 34).

Example 23

Survival-Promoting Effects of VPA Against Spontaneous DA Neuronal Death

VPA dose-dependently induces survival-promoting effects against spontaneous DA neuronal death in rat primary mesencephalic neuron-glia cultures.

In Example 23, [$^3$H]DA uptake assay and immunohistochemical analysis for TH-IR neurons were used to assess the viability of DA neurons in rat primary mesencephalic neuron-glia cultures in which approximately 1% of the neurons are dopaminergic. [$^3$H]DA uptake assays were performed as described in Example 1.

Rat primary mesencephalic neuron-glia cultures were prepared from the ventral mesencephalic tissues of embryonic day 13-14 Fisher 344 rats. Dissociated cells were seeded at a density of $5 \times 10^5$/well to poly-D-lysine-precoated 24-well plates. Cells were maintained at 37° C. in a humidified atmosphere of 5% $CO_2$ and 95% air, in minimal essential medium containing 10% fetal bovine serum (FBS), 10% horse serum, 1 gm/l glucose, 2 mM L-glutamine, 1 mM sodium pyruvate, 100 μM non-essential amino acids, 50 U/ml penicillin, and 50 μg/ml streptomycin. Unless otherwise indicated, seven-day-old cultures were used for treatment. At this time, immunocytochemical analysis indicated that the rat neuron-glia cultures contained 11% microglia, 48% astroglia, and 41% neurons, among which about 1% of cells represent tyrosine hydroxylase-immunoractive (TH-IR) neurons.

Valproic acid (VPA) (Sigma-Aldrich, St. Louis, Mo.) is prepared as a solution in double-distilled water and then sterile filtering immediately before use.

Seven days after seeding, each well was treated with indicated concentration of VPA or its vehicle. Seven days after treatment, the viability of dopaminergic neurons was assessed by [$^3$H]DA uptake assays. Quantified results are expressed as mean ±SEM of percentage of vehicle-treated cultures from three experiments performed in duplicate. *, $p<0.05$ compared with the corresponding vehicle-treated control cultures.

Figure 36:
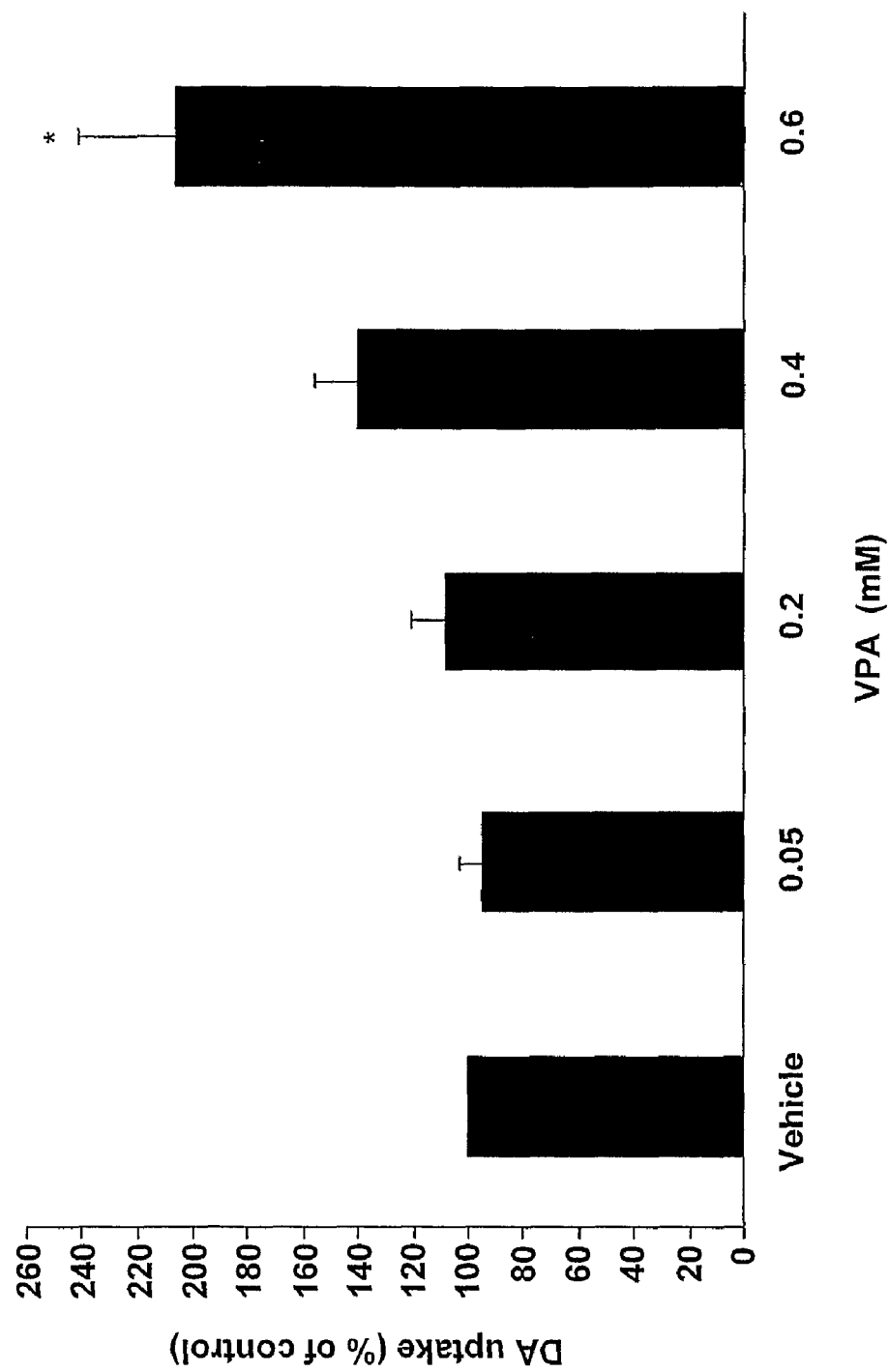
FIG. 36 is a graph depicting DA uptake as a percentage of control of neuron-glia cultures pretreated with various concentrations of VPA dose-dependently induces survival-promoting effects against spontaneous DA neuronal death in rat primary mesencephalic neuron-glia cultures.

As shown in FIG. 36, results indicated that VPA induced survival-promoting effects in a dose-dependent manner. At 0.6 mM, VPA significantly protected DA neurons from spontaneous neuronal death.

Figure 37:
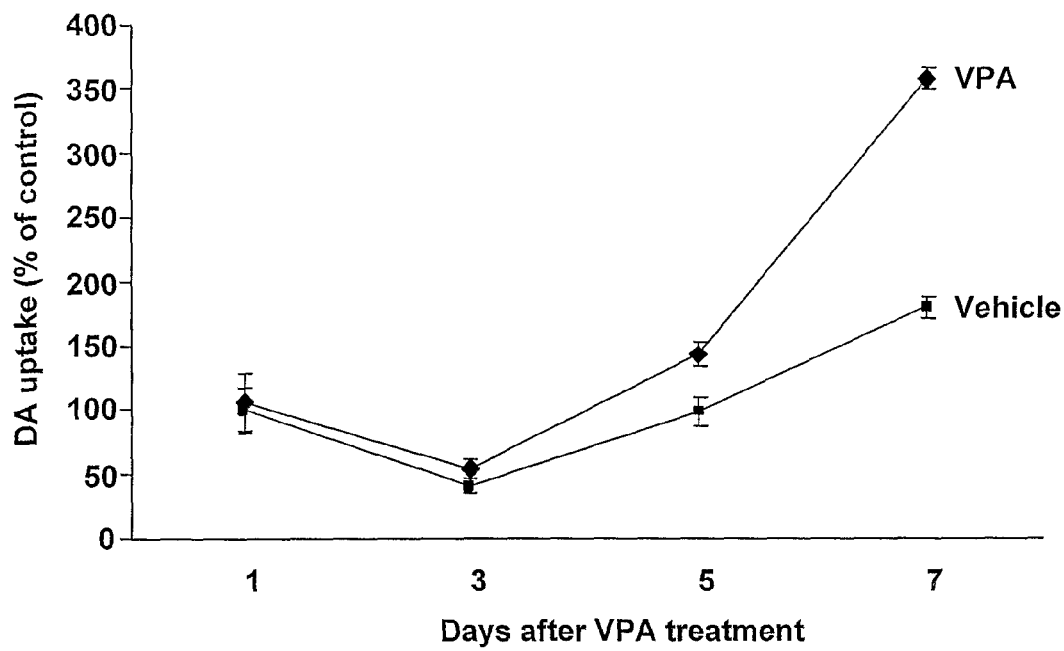
FIG. 37 is a graph depicting DA uptake as a percentage of control of neuron-glia cultures pretreated with various concentrations of VPA followed by time-dependent treatment with LPS.
Figure 38:
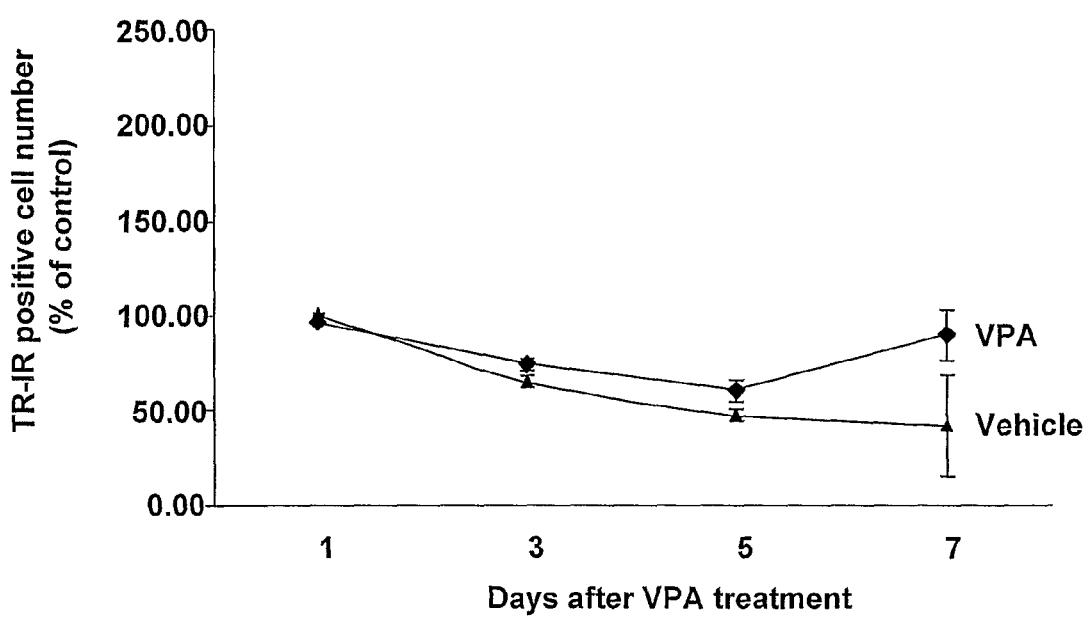
FIG. 38 is a graph illustrating the number of tyrosine hydroxylase (TH)-immunoreactive neurons after treatment with various concentrations of VPA followed by treatment with LPS.

Next, the rat primary mesencephalic neuron-glia cultures were treated with 0.6 mM VPA for various times to determine the treatment time-dependency. Rat primary mesencephalic neuron-glia cultures in a 24-well plate were treated with 0.6 mM VPA or its vehicle for indicated time 7 days after seeding. The viability of dopaminergic neurons was assessed by [H]DA uptake assays, shown in FIG. 37 or counting of TH-IR neurons, shown in FIG. 38. Quantified results are expressed as mean ±SEM of percentage of vehicle-treated control cultures from three experiments performed in duplicate. *, $p<0.05$ compared with the corresponding vehicle-treated control cultures. VPA treatment increased the capacity of [$^3$H]DA uptake and the number of TH-IR neurons in a time-dependent manner, as shown in FIGS. 37 and 38. In both cases, treatment with 0.6 mM VPA for 7 days, but not 3 or 5 days, resulted in a marked increase in the parameter compared with vehicle-treated control. VPA time-dependently induces survival-promoting effects against spontaneous DA neuronal death in rat primary mesencephalic neuron-glia cultures.

Example 24

Roles of Astroglia in VPA-Induced Neurotrophic Effects

Figure 39:
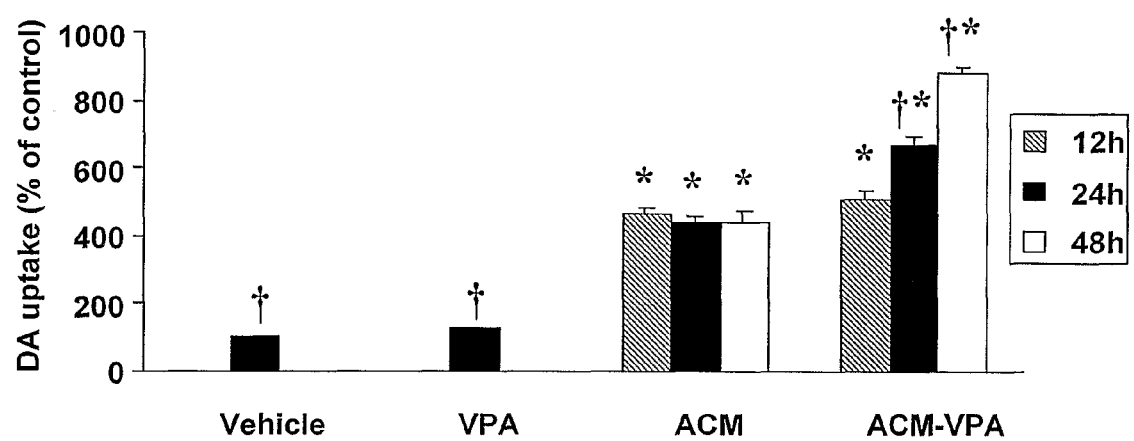
FIG. 39 is a graph showing DA uptake as a percentage of control for rat primary mesencephalic neuron-glia cultures pretreated with VPA alone, astrocyte conditioned medium (ACM), or ACM-VPA.

Whether astroglial cells are involved in the neurotrophic actions of VPA was tested by preparing media conditioned by incubation of astroglial cultures in the absence or presence 0.6 mM VPA. The results are shown in FIG. 39.

Mixed-glia cultures were first prepared from brains of 1-day-old Fisher 344 rat pups, as described previously (Liu, et al. 2001). Mechanically dissociated brain cells ($5 \times 10^7$) were seeded onto 150 cm$^2$ culture flasks in Dulbecco's modified Eagle's medium containing 10% heat-inactivated FBS, 2 mM L-glutamine, 1 mM sodium pyruvate, 100 µM non-essential amino acids, 50 U/ml penicillin, and 50 µg/ml streptomycin. The cultures were maintained at 37° C. in a humidified atmosphere of 5% $CO_2$ and 95% air, and medium was replenished 4 days after the initial seeding. Upon reaching confluence (usually 12-14 days later), microglia were detached from astroglia by shaking the flasks for 5 hours at 180 rpm. Astroglia were then detached with trypsin-EDTA and seeded in the same culture medium. After five or more consecutive passages, cells were seeded onto 24-well plates (10$^5$/well) for experiments. Immunocytochemical staining of the astroglia enriched cultures with either anti-GFAP or anti-OX-42 antibody indicated astroglial purity of greater than 98% and less than 2% of microglia contamination.

To exclude the possibility that the effects of ACM-VPA were due to the presence of VPA in the conditioned medium, ACM-VPA was dialyzed overnight using the Slide-A-Lyzer® Dialysis Cassette (Pierre Biotechnology, Inc) to remove small molecular weight substances. The dialyzed ACM-VPA still retained its ability to enhance DA uptake (data not shown here).

The astrocyte-conditioned medium (ACM) derived from incubation with astrocytes for 12, 24 or 48 hours showed an approximate 4-fold increase in DA uptake following incubation of mesencephalic neuron-enriched cultures with ACM for 7 days. The conditioned medium derived from incubation of astrocytes in the presence of 0.6 mM VPA (ACM-VPA) displayed a more robust (more than 8-fold), time-dependent increase in DA uptake, compared with ACM. Exposure of the neuron-enriched cultures to 0.6 mM VPA for 7 days caused a less than 2-fold increase in DA uptake, suggesting that a direct action on neurons does not play a major role in VPA-induced neurotrophic effects.

Conditioned medium derived from rat primary astroglial cultures treated with vehicle (ACM) or 0.6 mM VPA (ACM-VPA) were harvested after 12, 24 and 48 hours of incubation. Midbrain neuron-enriched cultures seeded in 24-well plates at a density of 5×10$^5$ cells/well were treated with vehicle, VPA, ACM or ACM-VPA for 7 days. Neurotrophic effect was quantified by [$^3$H]DA uptake assay.

The data are expressed as mean ±SEM of percentage of vehicle control from four to five independent experiments performed in triplicate; *, $p<0.001$ compared with the corresponding vehicle control cultures; †, $p<0.001$ compared with the corresponding ACM-treated cultures.

Neuron-enriched cultures were immunostained with MAP-2 for morphological examination. FIGS. 40A-40D show morphological features of neuron-enriched cultures were examined after incubation with vehicle (A), 0.6 mM VPA (B), ACM (C) or ACM-VPA (D) for 7 days and then immunocytostaining with MAP-2 antibody.

The immunostaining was carried out according to the following procedure. Formaldehyde (3.7%)-fixed cultures were treated with 1% hydrogen peroxide (10 min) followed by sequential incubation with blocking solution (30 min), primary antibody (overnight, 4° C.), biotinylated secondary antibody (2 hours), and ABC reagents (40 min) (Vector Laboratories, Burlingame, Calif.). The color development was achieved by the addition of 3,3'-diaminobenzidine. For morphological analysis, the images were recorded with an inverted microscope (Nikon, Tokyo, Japan) connected to a charge-coupled device camera (DAGE-MTI, Michigan City, Ind.) operated with the MetaMorph software (Universal Imaging Corporation, Downingtown, Pa.). For visual counting of TH-IR neurons, nine representative areas per well of the 24-well plate were counted under the microscope at 100× magnification.

Figure 40A:
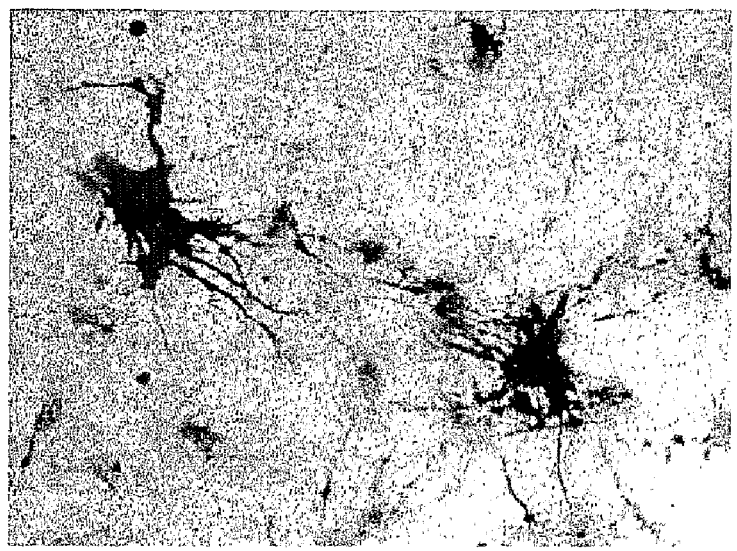
FIGS. 40A, 40B, 40C and 40D are photomicrographs showing morphological features of neuron-enriched cultures after incubation with vehicle (A), 0.6 mM VPA (B), ACM (C) or ACM-VPA (D) for 7 days and then immunocytostaining with MAP-2 antibody.
Figure 40B:
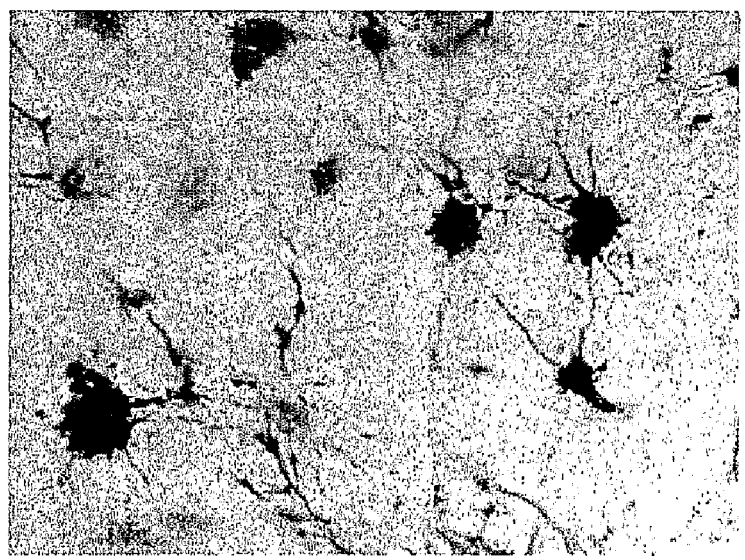
Figure 40C:
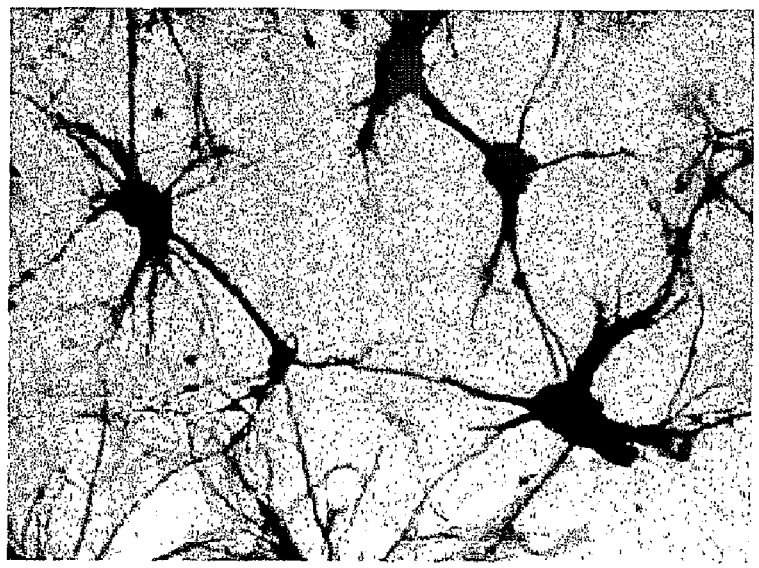
Figure 40D:
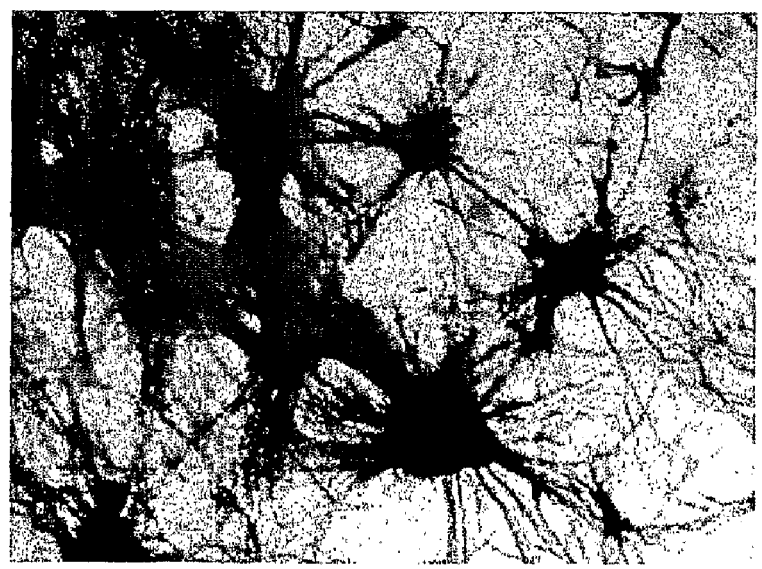

The results of the morphological examination are shown in FIGS. 20A-40D. Morphological examination of neuron-enriched cultures immunostained with MAP-2 demonstrated a dramatic increase in neurite outgrowth following exposure for 7 days to ACM-VPA conditioned with 48 hours incubation with astrocytes. (FIG. 40D), compared with the vehicle-treated control cultures (FIG. 40A). Much smaller effects were observed following incubation with the VPA alone or corresponding ACM (FIGS. 40B and 40C).

Figure 41A:
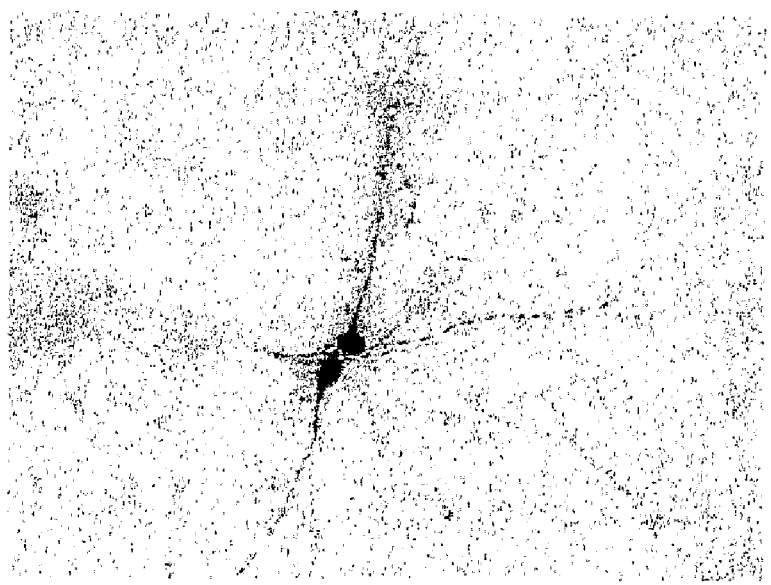
FIGS. 41A and 41B are photomicrographs showing morphological features of neuron-enriched cultures after incubation with ACM (A) or ACM-VPA (B) for 7 days and then immunocytostaining with TH-IR antibody.
Figure 41B:
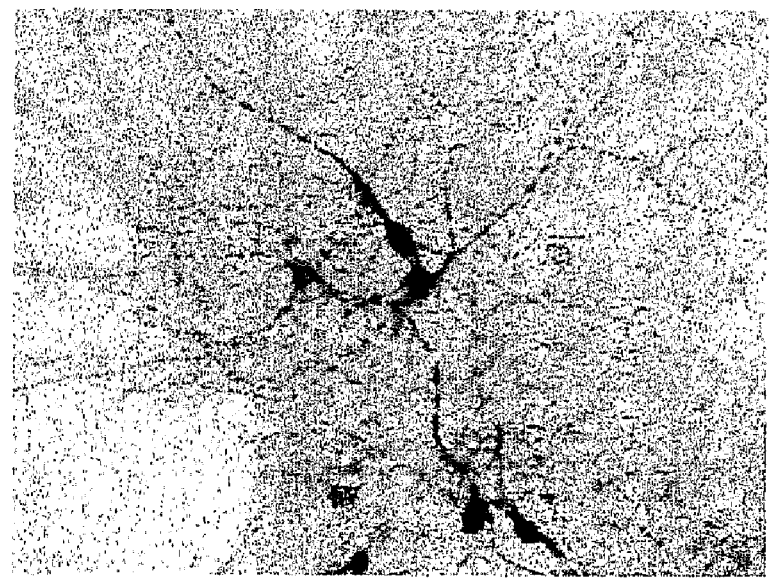

To specifically visualize morphological changes in DA neurons, we immunostained neuron-enriched cultures with anti-TH antibody. ACM and ACM-VPA were harvested after 48 hours incubation of astrocyte with vehicle and 0.6 mM VPA, respectively. Images shown are representative of at least three independent experiments. FIG. 30 shows morphological features of neuron-enriched cultures were examined after incubation with ACM (A) or ACM-VPA (B) for 7 days and then immunocytostaining with TH-IR antibody. Results demonstrated higher density of DA neurons, more complex neurite configurations and more neuronal connections in ACM-VPA-treated cultures (FIG. 41A) than ACM-treated cultures (FIG. 41B).

Example 25

GDNF as a Mediator of VPA-Induced Astroglia-Derived Neurotrophic Effects

To test that GDNF is VPA-induced, astroglia-secreted neurotrophic substance, we used real time PCR and ELISA to quantify GDNF mRNA and protein levels, respectively.

Rat primary astroglias were exposed to 0.6 mM VPA for various times ranging from 6 to 48 hours. Total RNA was extracted from cells by Tri reagent (Sigma) and purified with RNeasy columns (Qiagen, Valencia, Calif.). Expression of the selected genes was quantified using real-time RT-PCR analysis. Briefly, total RNA was reverse transcribed with MuLV reverse transcriptase and oligo-dT primers. The forward and reverse primers for selected genes were designed using Primer Express software. The SYBR green DNA PCR kit (Applied Biosystems, Foster City, Calif.) was used for real-time PCR analysis. The relative differences in expression between groups were expressed using cycle time (Ct) values and the relative differences between groups were expressed as relative increases setting the control as 100%. Assuming that the Ct value is reflective of the initial starting copy and that there is 100% efficacy, a difference of one cycle is equivalent to a two-fold difference in the starting copy.

Figure 42:
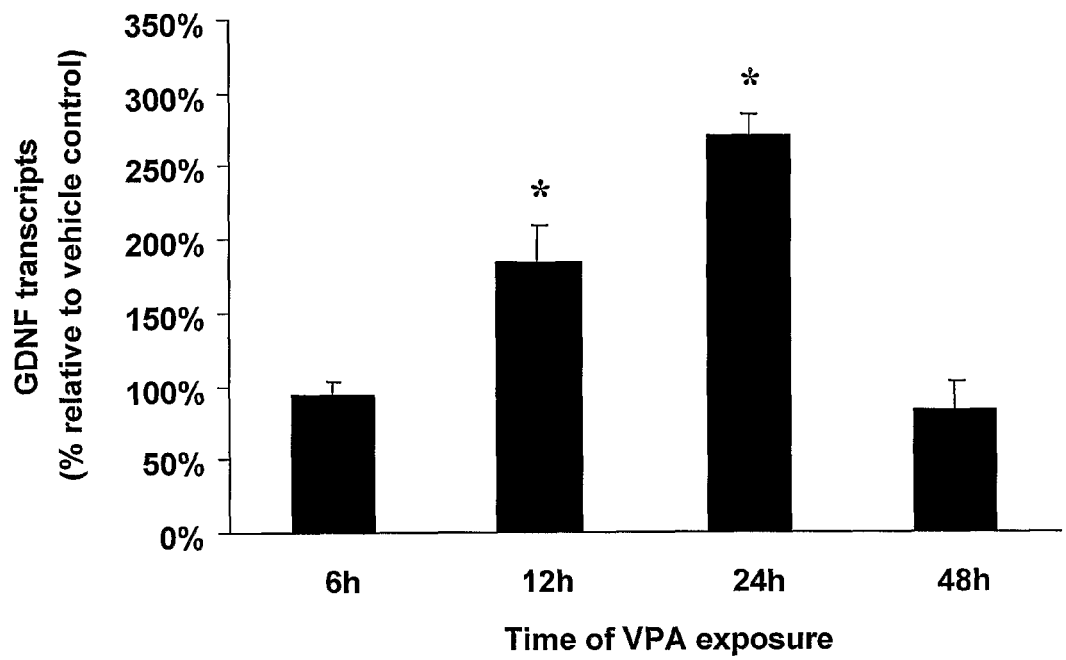
FIG. 42 is a graph showing time-dependent GDNF transcript levels extracted from rat primary astrocytes and quantitated by real-time PCR relative to vehicle control following for various times ranging from 6 to 48 hours following treatment with VPA.

Quantified results, shown in FIG. 42, are expressed as mean ±SEM of percentage of vehicle-treated control cultures from four experiments performed in triplicate. Results showed that VPA treatment caused a time-dependent increase in GDNF mRNA levels in astroglial cultures. This increase was about 180% at 12 hours, 265% at 24 hours and back to the control value at 48 hours (FIG. 42).

Figure 43:
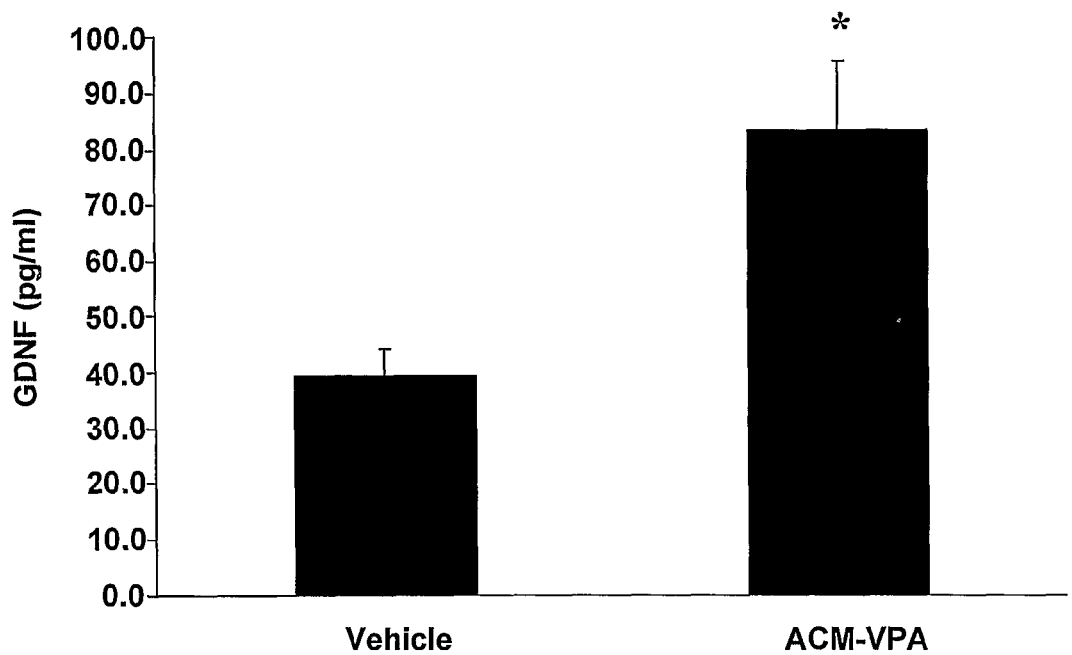
FIG. 43 is a graph showing secreted GDNF levels from rat primary astrocytes collected 48 hours after ACM-VPA treatment and analyzed by ELISA.

Next, we used ACM-VPA to analyze secreted GDNF protein. ACM-VPA was prepared according to Example 20 and collected 48 hours after incubation with astroglia. In FIG. 43, ACM-VPA was analyzed for secreted GDNF by ELISA. GDNF levels were measured with an ELISA kit (GDNF Emax ImmunoAssay System; Promega, Madison, Wis.), according to the protocol of the supplier. The levels of GDNF were expressed as pg per ml of supernatant. The assay sensitivity ranged from 16 to 1000 pg/ml. Results are expressed as pg/ml from three experiments performed in duplicate. ACM-VPA showed a 2.1-fold over the vehicle control in levels of GDNF protein (39 vs 83 pg/ml) (FIG. 43).

To investigate whether GDNF-neutralization interfered with the VPA-induced effects on DA neurons, ACM-VPA was pretreated with goat anti-GDNF IgG overnight prior to the addition to mesencephalic neuron-enriched cultures.

Rat mesencephalic neuron-enriched cultures are prepared from dissociated ventral mesencephalic cells from embryonic day 13-14 Fisher 344 rats were seeded first at a density of $5 \times 10^5$/well to poly-D-lysine-precoated 24-well culture plates. Twenty hours after plating, cytosine-β-D-arabinofuranoside (10 μM) was added to the cultures to suppress the proliferation of non-neuronal cells, notably glia. Three days later, the culture medium was replaced with the maintenance medium. Routinely, the seven-day-old neuron-enriched cultures were used for treatment. At this time the neuron-enriched cultures contained less than 0.1% microglia, and 8% astroglia, as revealed by immunochemical analysis. Of the Neu-N immunoractive neurons, 2.7-3.9% was TH-IR neurons.

Figure 44:
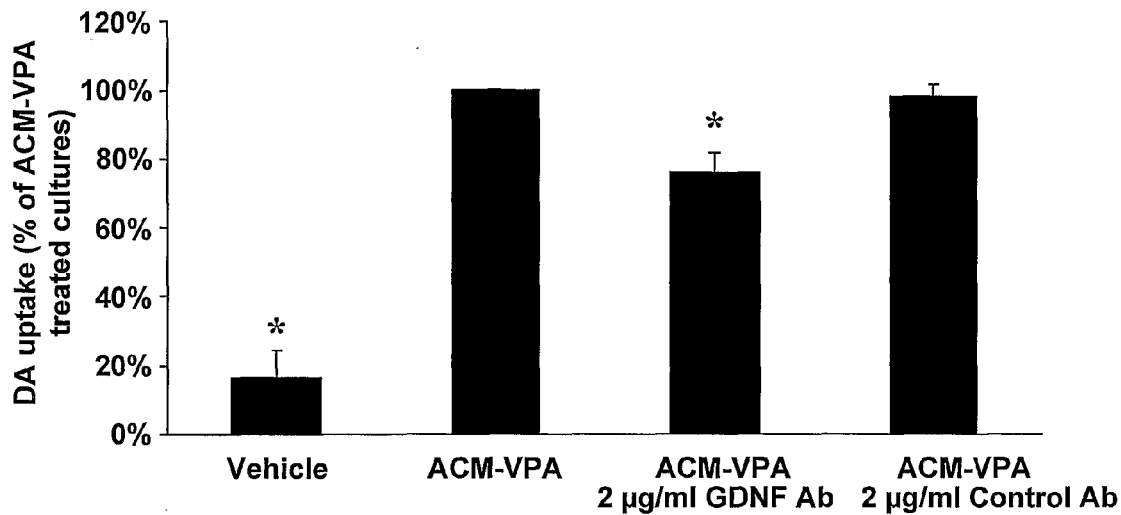
FIG. 44 is a graph showing DA uptake measured seven days after ACM-VPA, pre-incubated overnight with 2 μg/ml of either control goat IgG or goat anti-GDNF IgG, added to mesencephalic neuron-enriched cultures.

Neutralization of GDNF was performed by the addition of 2 μg/ml goat total anti-GDNF IgG (1:100 dilutions; R&D Systems, Minneapolis, Minn.) to ACM-VPA. The ACM-VPA was incubated overnight with 2 μg/ml of either control goat IgG or goat anti-GDNF IgG, and then added to the mesencephalic neuron-enriched cultures for 7 days prior to measuring DA uptake capacity. [$^3$H]DA uptake assays were performed according to the procedure presented in Example 1. Results, shown in FIG. 44, are expressed as means ±SEM of percentage DA uptake in the cultures treated with ACM-VPA from three independent experiments. *, p<0.05 compared with the ACM-VPA (C) treated cultures. The GDNF-neutralizing antibody significantly reduced the ACM-VPA-induced increase in DA uptake capacity following 7 days of incubation, while pretreatment with control IgG was without effect (FIG. 44).

All statistical analyses were performed with SPSS software v. 10.0, and p-values of ≦0.05 were considered significant in all tests. GDNF transcript abundance was expressed as a ratio of actin internal control. All dose-response experiments were analyzed by one-way analysis of variance (ANOVA), with treatments as the independent variable, followed by Dunnett's test comparing each treatment to the vehicle.

Example 26

VPA Robustly Protects DA Neurons from Neurotoxicity Induced by LPS and MPP$^+$

Whether VPA also protects DA neurons against LPS-induced neurotoxicity was investigated in the primary mesencephalic neuron-glia cultures.

Mixed-glia cultures were first prepared from brains of 1-day-old Fisher 344 rat pups, as described previously (Liu, Wang et al. 2001). Briefly, mechanically dissociated brain cells ($5 \times 10^7$) were seeded onto 150-cm$^2$ culture flasks in Dulbecco's modified Eagle's medium containing 10% heat-inactivated FBS, 2 mM L-glutamine, 1 mM sodium pyruvate, 100 μM non-essential amino acids, 50 U/ml penicillin, and 50 μg/ml streptomycin. The cultures were maintained at 37° C. in a humidified atmosphere of 5% $CO_2$ and 95% air, and medium was replenished 4 days after the initial seeding. Upon reaching confluence (usually 12-14 days later), microglia were detached from astroglia by shaking the flasks for 5 h at 180 rpm. Astroglias were then detached with trypsin-EDTA and seeded in the same culture medium. After five or more consecutive passages, cells were seeded onto 24-well plates ($10^5$/well) for experiments. Immunocytochemical staining of the astroglia enriched cultures with either anti-GFAP or anti-OX-42 antibody indicated a astroglial purity of greater than 98% and less than 2% of microglia contamination.

Figure 45:
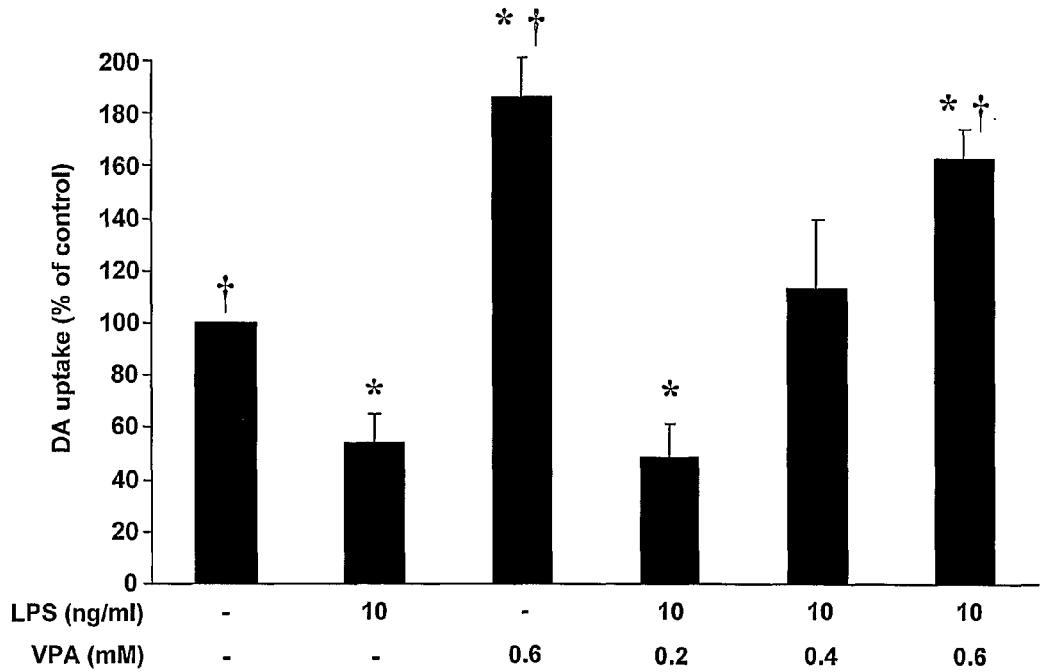
FIG. 45 is a graph showing DA uptake in rat primary mesencephalic neuron-glia cultures treated for 48 hours with indicated concentrations of VPA followed by treatment with 10 ng/ml LPS FIG. 46 VPA is a graph showing DA uptake in rat primary mesencephalic neuron-glia cultures treated for indicated time with 0.6 mM VPA followed by treatment with 10 ng/ml LPS.

Mixed-glia cultures were pretreated with various doses of VPA for 48 hours and then expose to 10 ng/ml LPS for 5 days. Dose-dependent effect of VPA on LPS-induced DA neuron degeneration is shown in FIG. 45. LPS treatment reduced the uptake capacity of DA by 45% and this loss was robustly blocked by VPA pretreatment in a dose-dependent manner. In fact, at 0.6 mM, the DA uptake levels in the VPA-pretreated cultures, either alone or in conjunction with LPS, were significantly higher than those in the untreated control.

Figure 46:
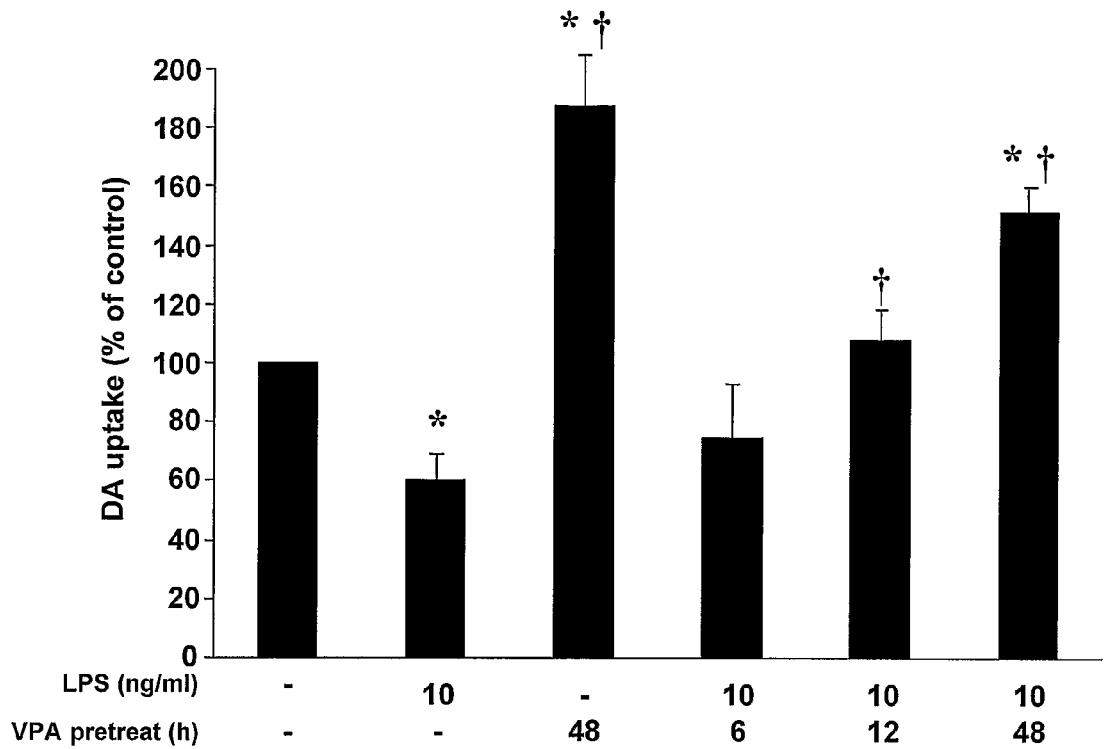

Time-dependent neuroprotective effects of VPA on LPS-induced DA neuron degeneration are shown in FIG. 46. The mixed-glia cultures seeded in a 24-well plate were treated for indicated time with 0.6 mM VPA followed by treatment with 10 ng/ml LPS. While pretreatment with 0.6 mM for 6 hours failed to induce a significant effect, a 12 hours-pretreatment produced a complete neuroprotection against LPS neurotoxicity and a 48 hours-pretreatment caused a further increase in DA uptake levels (FIG. 46).

Morphological assessments of dopaminergic neurons in the primary mesencephalic neuron-glia cultures are shown in FIGS. 47A-47F. The cultures were treated with vehicle alone (A), 0.6 mM VPA alone (B), 10 ng/ml LPS alone (C) or pretreated for 48 hours with 0.2 (D), 0.4 (E) or 0.6 mM VPA (F) followed by treatment with 10 ng/ml LPS. Seven days later, cultures were immunostained with anti-TH antibody. Images shown are representative of three separate experiments.

Figure 47A:
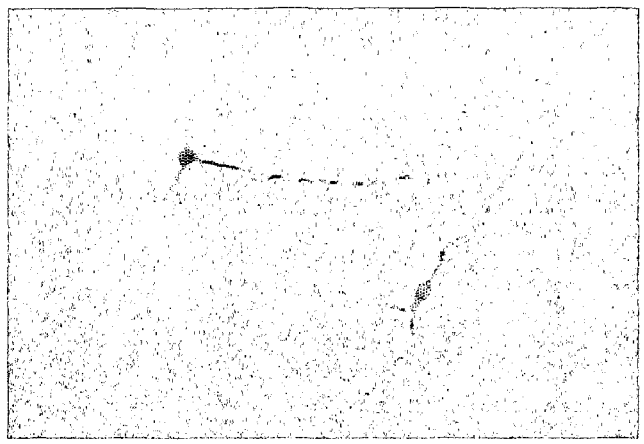
FIGS. 47A, 47B, 47C, 47D, 47E and 47F VPA are images dopaminergic neurons in the primary mesencephalic neuron-glia cultures treated with vehicle alone (A), 0.6 mM VPA alone (B), 10 ng/ml LPS alone (C) or pretreated for 48 hours with 0.2 (D), 0.4 (E) or 0.6 mM VPA (F) followed by treatment with 10 ng/ml LPS and 7 days later immunostained with anti-TH antibody.
Figure 47B:
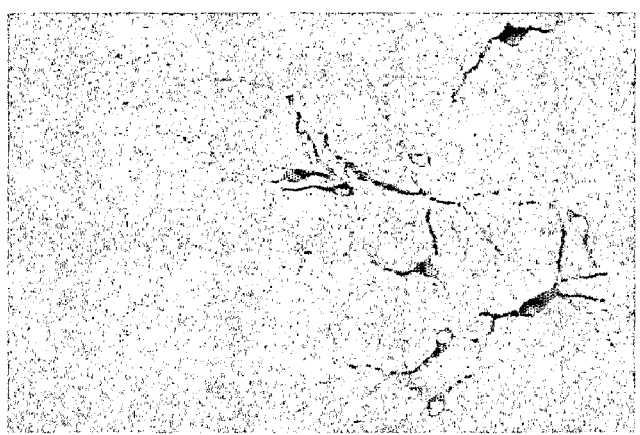
Figure 47C:
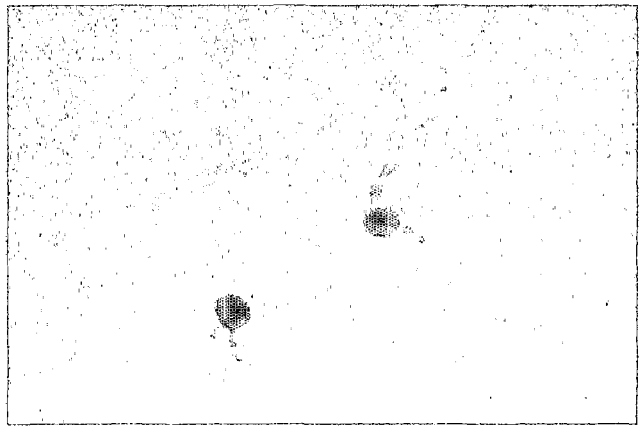
Figure 47D:
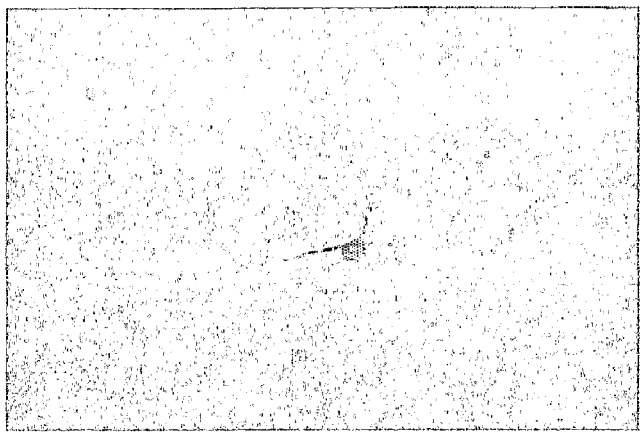
Figure 47E:
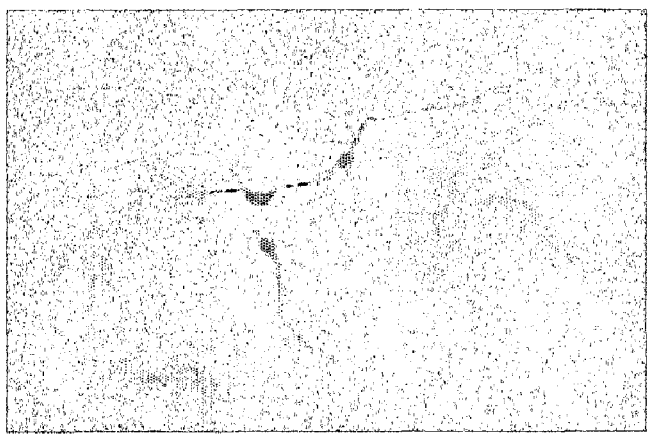
Figure 47F:
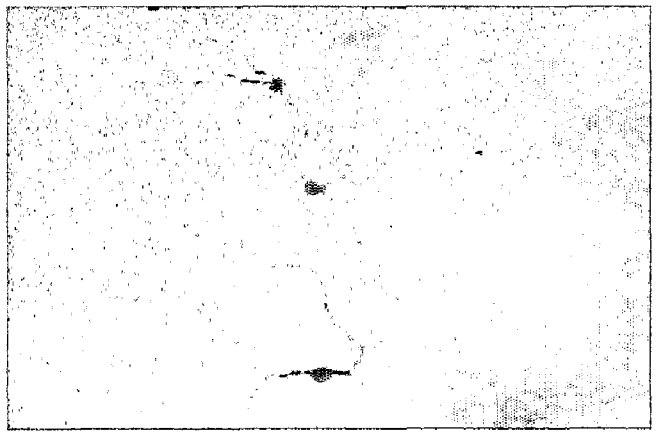

Morphological assessments of DA neurons immunostained with anti-TH antibody revealed that VPA treatment promoted neurite formation and inter-neuronal networks (FIGS. 47A and 47B). In contrast, LPS treatment caused degeneration of DA neuronal soma and loss of neuritis and dendritic nodes (FIG. 47C). These LPS-induced morphological changes were dose-dependently, prevented by VPA pretreatment in the concentration range examined (0.2 to 0.6 mM).

Finally, we investigated whether VPA is able to protect against neurotoxicity induced by MPP$^+$, another PD-inducing toxin, in the mesencephalic neuron-enriched cultures, which contains a much reduced % of astroglia (8% in the neuron-enriched culture vs. 50% in the neuron-glia culture). The MPP$^+$ model in neuron-enriched cultures could provide a clue to determine the directly protective effect of VPA on neurons, since it is known that MPP$^+$ exerted direct DA neurotoxicity. Neuron-enriched cultures were prepared according the description in Example 25.

Figure 48:
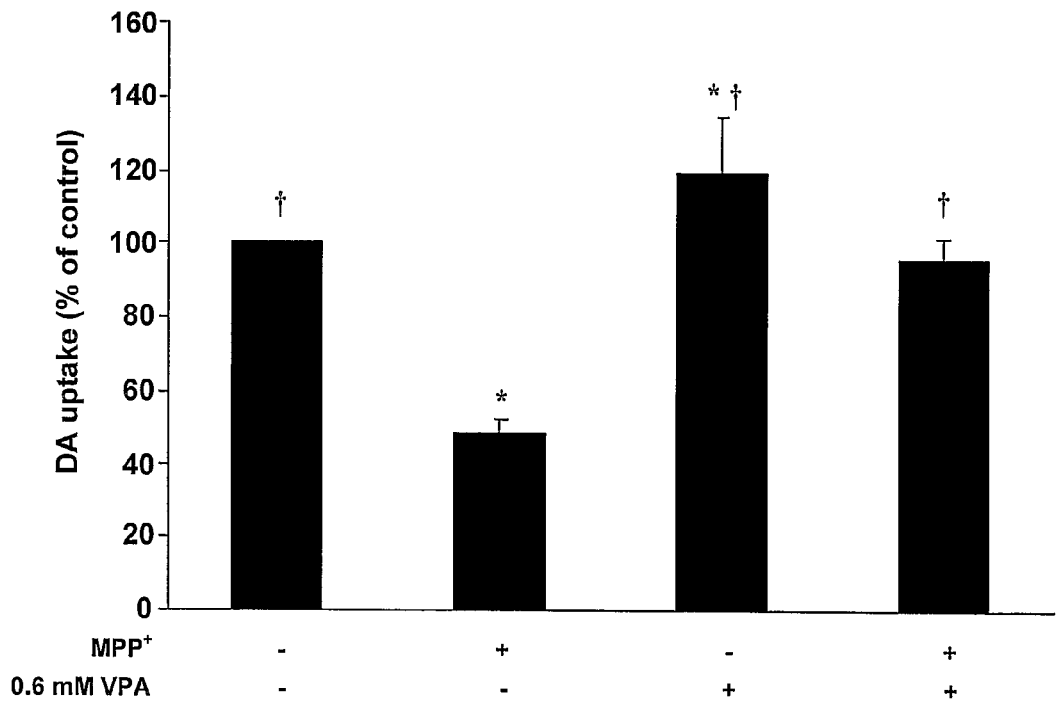
FIG. 48 is a graph showing DA uptake in mesencephalic neuron-enriched cultures pretreated for 48 hours with 0.6 mM VPA followed by treatment with 0.5 μM MPP+ and [$^3$H]DA uptake was measured 7 days later.

Neuroprotective effects of VPA on MPP$^+$ induced DA neurodegeneration in the mesencephalic neuron-enriched cultures is shown in FIG. 48. Neuron-enriched cultures seeded in 24-well culture plates were pretreated for 48 hours with 0.6 mM VPA followed by treatment with 0.5 μM MPP$^+$. [$^3$H]DA uptake was measured 7 days after MPP$^+$ treatment according to procedures described in Example 1. Results are expressed as mean ±SEM of percentage of vehicle control from three independent experiments performed in duplicate. *, p<0.05 compared with vehicle-treated cultures. †, p<0.05 compared with corresponding MPP$^+$-treated cultures.

Treatment with 0.5 μM MPP$^+$ for 7 days resulted in a decrease by more than 50% in DA uptake levels (FIG. 48). Pretreatment with 0.6 mM VPA for 48 hours blocked the MPP+-induced degeneration of DA neurons. However, the neuroprotective effect is less pronounced than the protection against LPS-induced neurotoxicity in neuron-glial cultures, which containing 48% astroglia. In addition, neuron-enriched cultures treated with VPA alone showed much less neurotrophic effects than that found in neuron-glial cultures, again suggesting that VPA-induced neurotrophic and neuroprotective effects were dependent on the presence of astroglia.

Example 27

The HDAC Inhibitor Sodium Butyrate Mimics the Neurotrophic Effect of VPA on DA Neurons HDAC is inhibited by therapeutically relevant concentrations of VPA and plays important roles in gene regulation; it could be the target of VPA-induced neuronal survival-promoting effects. We then asked whether an established HDAC inhibitor induces neurotrophic effect in midbrain neuron-glia culture similar to VPA.

Figure 49:
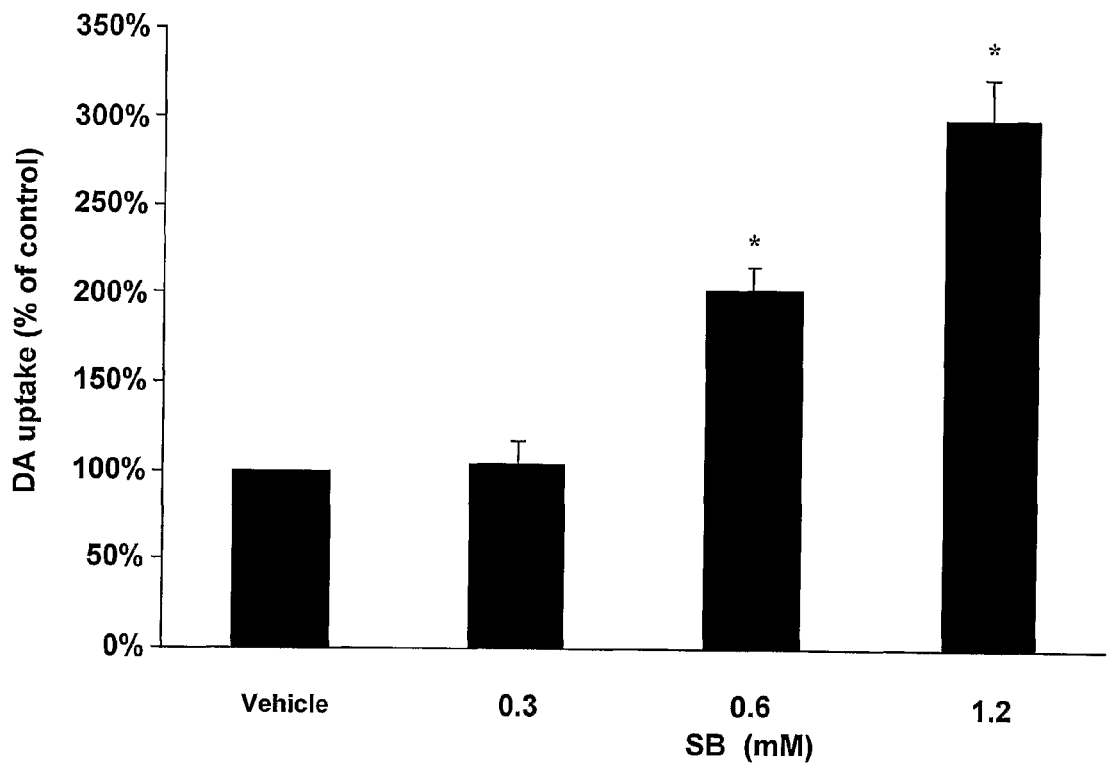
FIG. 49 is a graph showing DA uptake in rat primary mesencephalic neuron-glia cultures seeded in a 24-well culture plate at density of $5 \times 10^5$ per well were treated with indicated concentrations of sodium butyrate or its vehicle 7 days after seeding.

Rat primary mesencephalic neuron-glia cultures seeded in a 24-well culture plate at density of $5 \times 10^5$ per well were treated with indicated concentrations of sodium butyrate or its vehicle 7 days after seeding. The viability of dopaminergic neurons was assessed by DA uptake assays 7 days after sodium butyrate addition. Exposure of midbrain neuron-glia culture to indicated concentrations of sodium butyrate had a pronounced neurotrophic effect closely mimicked VPA in a dose-dependent manner (FIG. 49).

Figure 50:
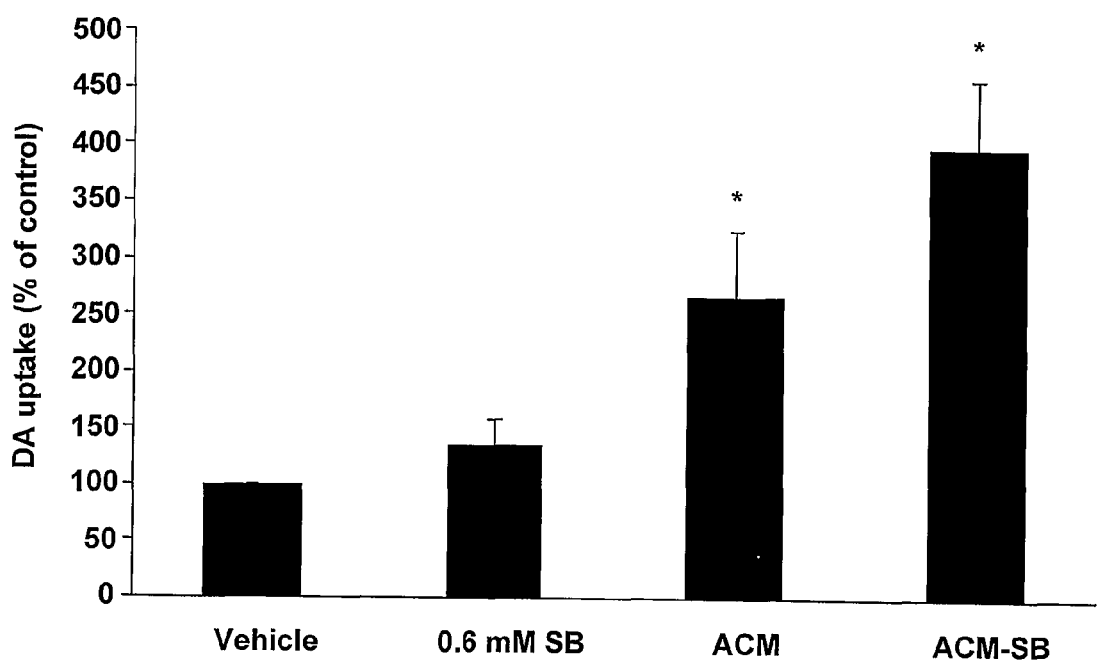
FIG. 50 is a graph showing DA uptake in midbrain neuron-enriched cultures 7 days after treatment with vehicle, sodium butyrate, ACM (conditioned medium derived from rat primary astroglial cultures treated with vehicle) or ACM-Sodium butyrate (conditioned medium derived from rat primary astroglial cultures treated with 0.6 mM sodium butyrate) for 7 days.

To explore whether astroglial cells are also the main target of sodium butyrate-induced neurotrophic effect, we prepared media conditioned by incubation of astroglial cultures in the absence or presence 0.6 mM sodium butyrate. Conditioned medium derived from rat primary astroglial cultures treated with vehicle (ACM) or 0.6 mM sodium butyrate (ACM-Sodium butyrate) were harvested after 48 hours of incubation. Midbrain neuron-enriched cultures seeded in 24-well plates at a density of $5 \times 10^5$ cells/well were treated with vehicle, sodium butyrate, ACM or ACM-Sodium butyrate for 7 days. Seven days after treatment, neurotrophic effect for dopaminergic neurons was assessed by [H]DA uptake assays. The conditioned medium derived from incubation of astrocytes in the presence of 0.6 mM sodium butyrate (ACM-sodium butyrate) displayed a more robust increase in DA uptake, compared with ACM in mesencephalic neuron-enriched cultures (FIG. 50). Moreover, exposure of the neuron-enriched cultures to 0.6 mM sodium butyrate for 7 days caused a less than 2-fold increase in DA uptake, suggesting that a direct action on neurons does not play a major role in sodium butyrate-induced neurotrophic effects.

Quantified results are expressed as mean ±SEM of percentage of vehicle-treated cultures from three experiments performed in duplicate. *, p<0.05 compared with the corresponding vehicle-treated control cultures.

Example 28

3-HM is Neurotrophic to Dopaminergic Neurons

Mesencephalic neuron-glia cultures, prepared as described above, were pretreated with vehicle or 3-HM (1-5 µM) before the treatment of LPS (10 ng/ml). Seven days later, the degeneration of dopaminergic neurons was determined by the functional assay of [$^3$H] DA uptake and by the morphometric measurement of dopaminergic neurons following immunostaining with an anti-TH antibody. [$^3$H] DA and immunostaining are performed as described above.

Figure 51:
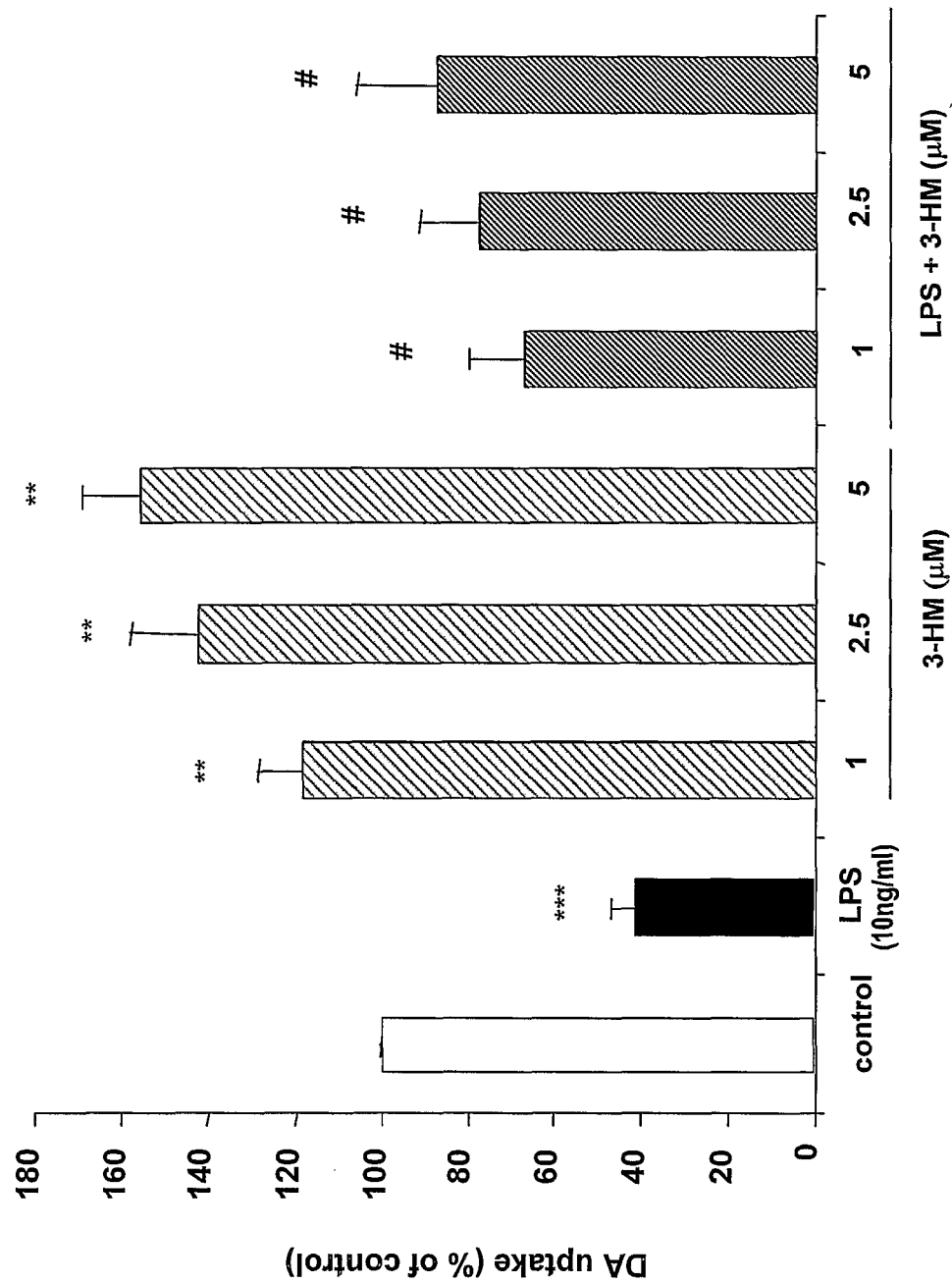
FIG. 51 is a graph showing DA uptake in mesencephalic neuron-glia cultures pretreated for 30 min with 3-hydroxymorphinan (3-HM) (1-5 μM) followed by treatment with 10 ng/mL LPS.

As shown in FIG. 51, the results indicated that LPS reduced DA uptake capacity by ~60% compared with the vehicle-treated control cultures. 3-HM significantly attenuated the LPS-induced reduction in DA uptake, in a dose-dependent manner. At 5 µM, 3-HM reversed the LPS-induced decrease in DA uptake almost back to the vehicle-treated control values. More interestingly, treatment with 3-HM (1-5 µM) alone for 7 days dose-dependently increased DA uptake capacity by 20-60% compared with the vehicle-treated control cultures, indicating that 3-HM exerted a neurotrophic effect on dopaminergic neurons.

Figure 52:
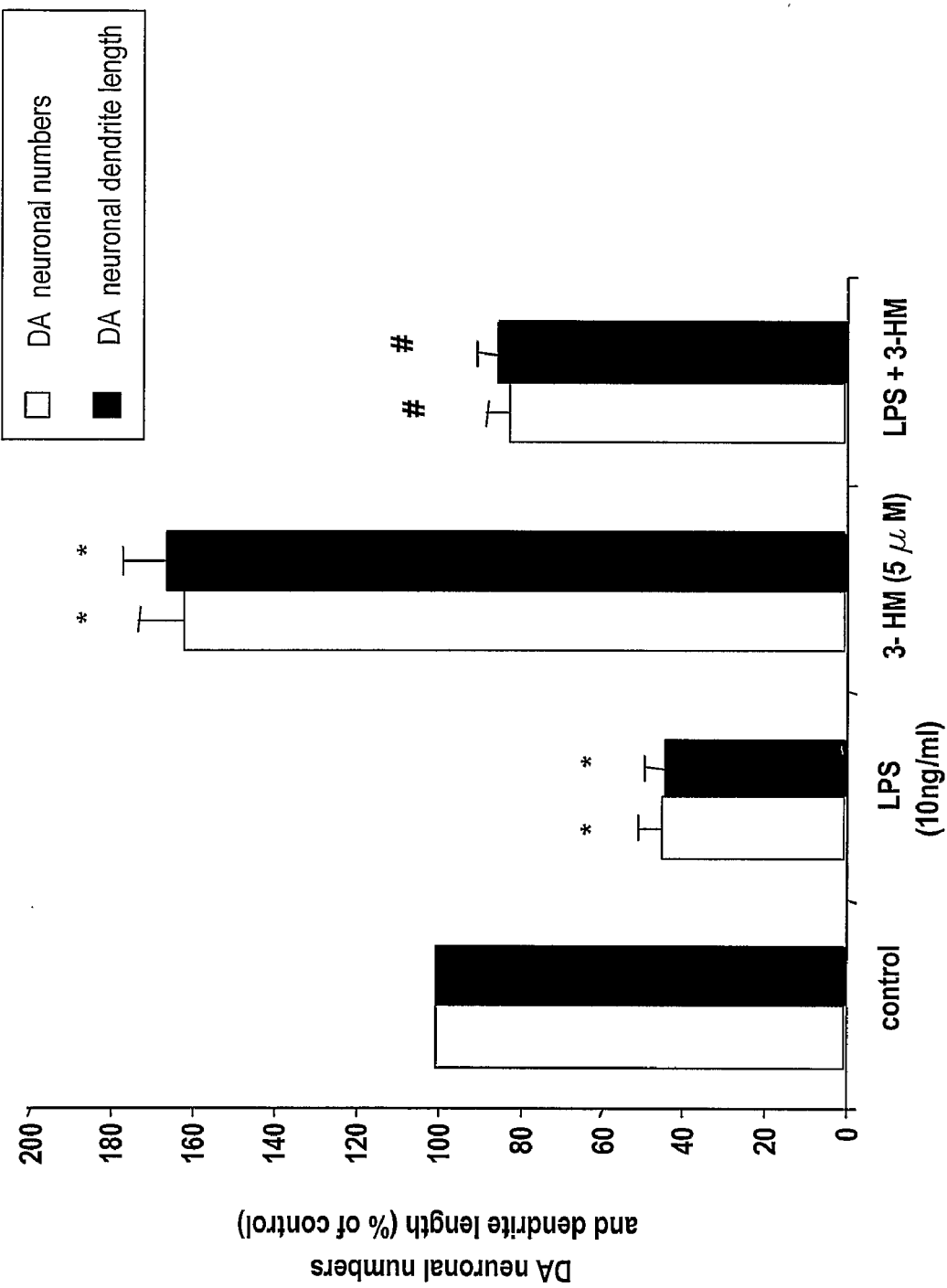
FIG. 52 is a graph showing immunocytochemical analysis, including TH-ir neuron counts and neurite length measurements in mesencephalic neuron-glia cultures pretreated for 30 min with 3-HM (1-5 μM) followed by treatment with 10 ng/mL LPS.
Figure 53A:
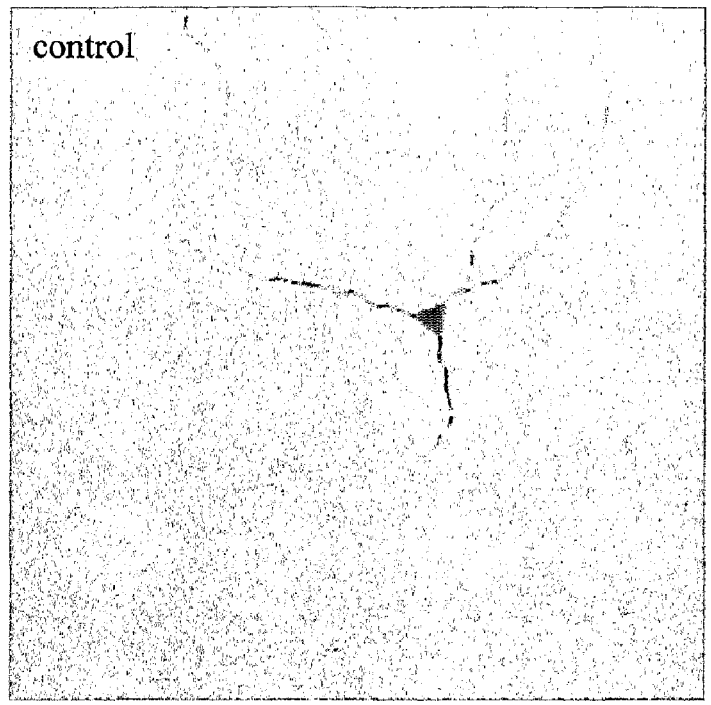
FIGS. 53A, 53B, 53C and 53D are representative pictures of immunostaining of cells from mesencephalic neuron-glia cultures pretreated for 30 min with 3-HM (1-5 μM) followed by treatment with 10 ng/mL LPS.
Figure 53B:
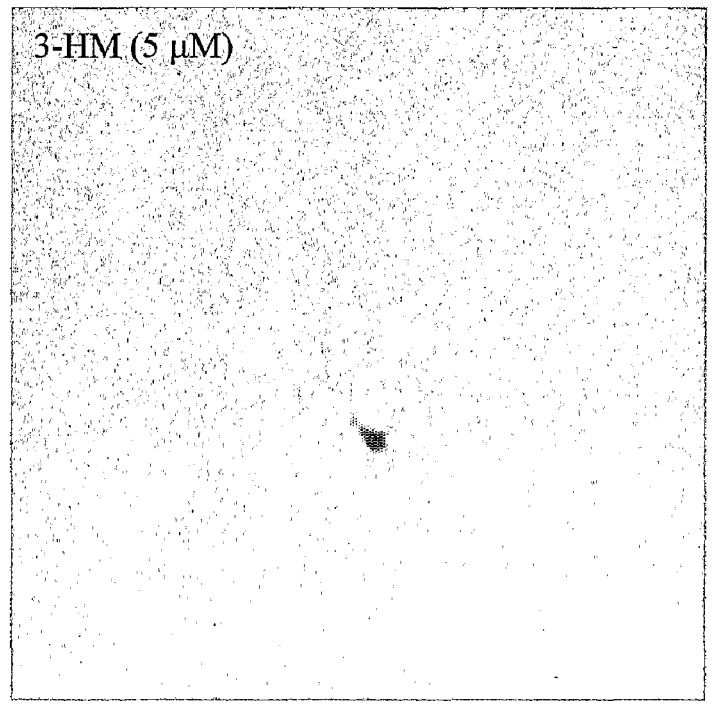
Figure 53C:
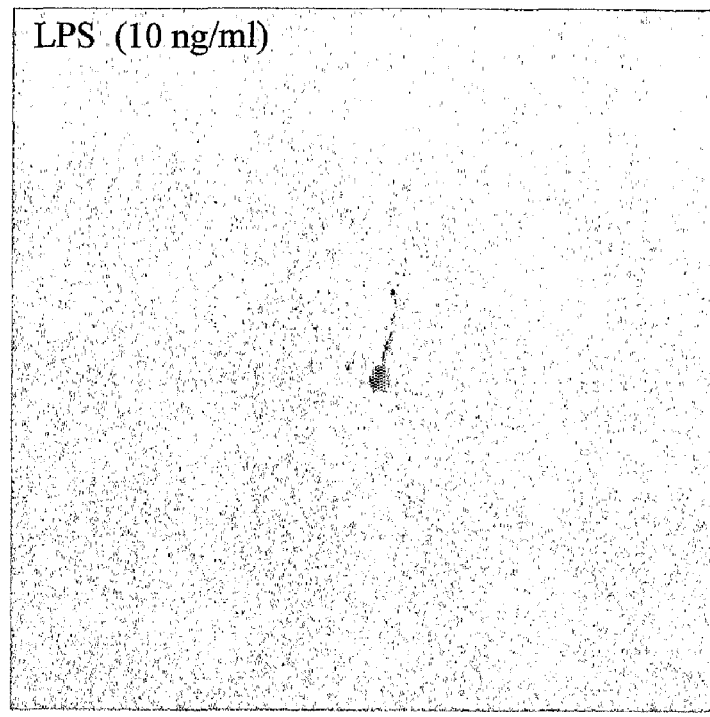
Figure 53D:
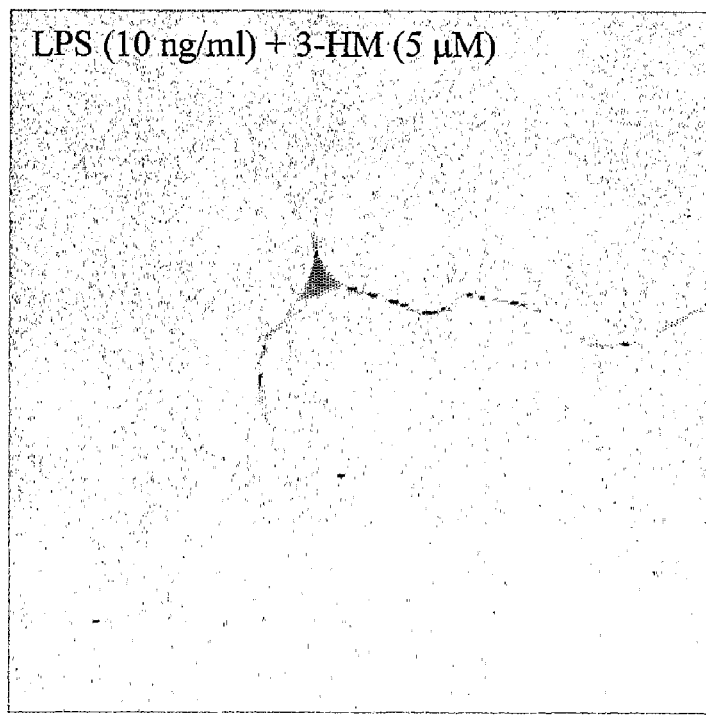

Results from the morphometric measurements revealed a pattern of changes similar to that of the DA uptake studies. Cell count analysis showed that LPS reduced the number of dopaminergic neurons by 51% compared with the vehicle-treated control cultures (FIG. 52). Pretreatment with 3-HM (5 µM) significantly restored the LPS-induced reduction in the number of dopaminergic neurons to 97% of the vehicle-treated control cultures (FIG. 52). The average length of dopaminergic neuronal neurites in the LPS-treated cultures was 43% of the vehicle-treated control cultures, and 3-HM pretreatment increased the length to 110% of the vehicle-treated control cultures (FIG. 52). As shown in FIG. 53, following the LPS treatment, in addition to the reduction in the abundance of dopaminergic neurons, the neurites of the remaining TH-ir neurons became shorter, lighter-stained, or even fragmented. Following pretreatment with 3-HM (5 µM), dopaminergic neurons were significantly more numerous and their neurites were less affected compared with the LPS-treated cultures. These morphological findings were consistent with the results of the functional assay of DA uptake mentioned above.

Example 29

Neurotrophic Effect of 3-HM is Glia-Dependent and Astroglia, not Microglia, Contribute to the Neurotrophic Effect of 3-HM One of the most interesting findings of this study was that 3-HM alone exerted a significant neurotrophic effect in the mesencephalic neuron-glia cultures. This effect was not observed with its parent compound DM. To determine the target of 3-HM's neurotrophic effect, we first investigated whether 3-HM has a direct effect on dopaminergic neurons using neuron-enriched cultures.

Various concentrations of 3-HM (0.1-5 µM) or vehicle were added to the following different cell cultures: neuron-enriched cultures (A); reconstituted cultures by adding 10% and 20% ($5 \times 10^4$/well and $1 \times 10^5$/well) of microglia to the neuron-enriched cultures (B); reconstituted cultures by adding 40% and 50% ($2 \times 10^5$/Well and $2.5 \times 10^5$/well) of astroglia to the neuron-enriched cultures (C). Cultures are prepared as described in Example 25. The [$^3$H]DA uptake measurements were performed 10 days after treatment. Results were expressed as a percentage of the vehicle-treated control cultures and were the mean ±SE from five (A) and four (B,C) independent experiments in triplicate. *P<0.05 and **P,0.001 compared with the vehicle-treated control cultures. #P<0.05 compared with the augmented cultures with 40% astroglia. N, neuron-enriched cultures; N+10% (20%) MG: 10% (20%) of microglia were added back to the neuron-enriched cultures; N+40% (50%) AS: 40% (50%) of astroglia were added back to the neuron-enriched cultures.

Figure 54:
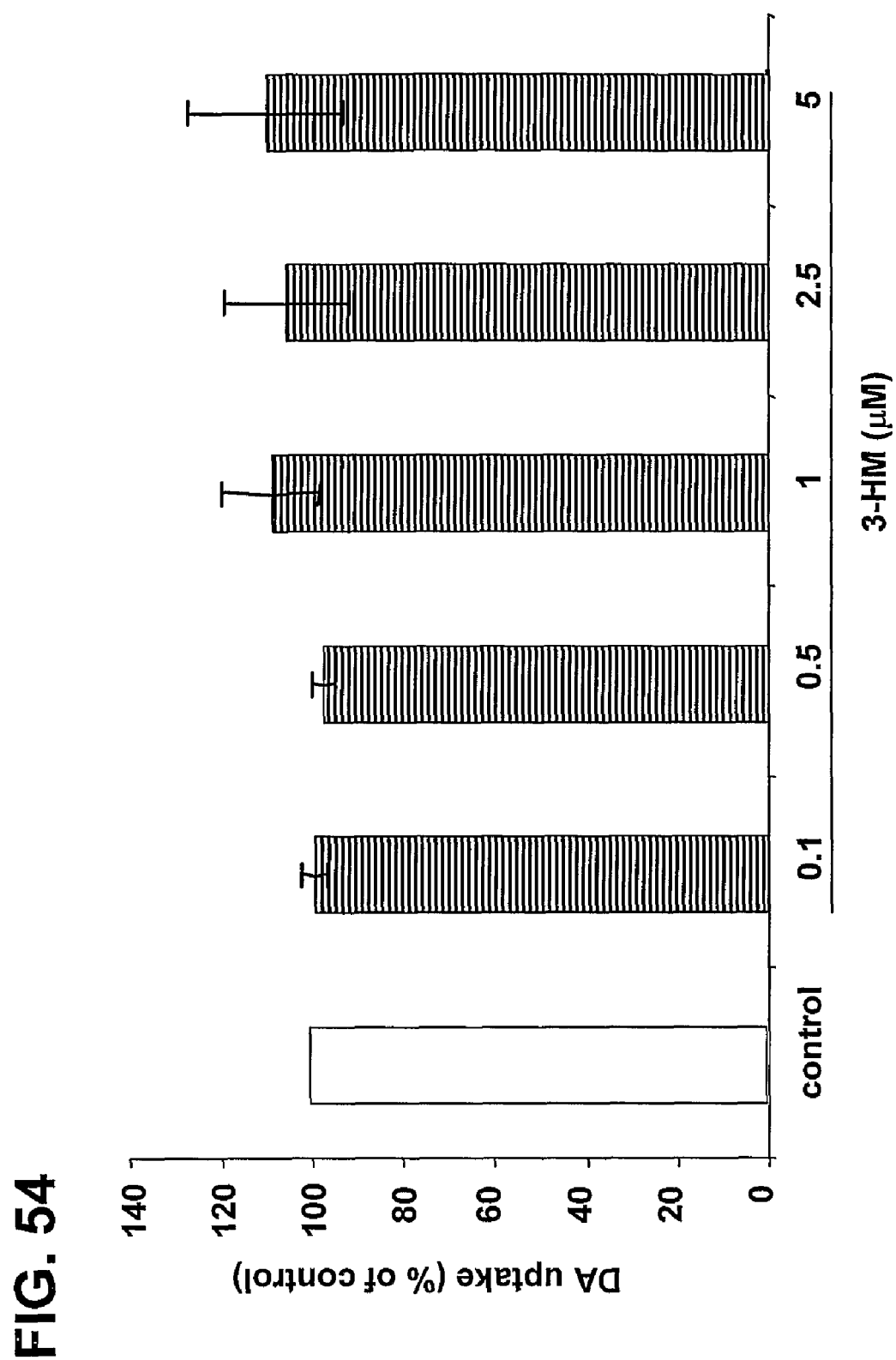
FIG. 54 is a graph showing DA uptake in neuron-enriched cultures treated with various concentrations of 3-HM (1-5 μM))

3-HM (0.1-5 µM) failed to show a significant increase in the DA uptake capacity, indicating that the observed 3-HM-induced neurotrophic effect was not due to a direct effect on dopaminergic neurons (FIG. 54).

Figure 55:
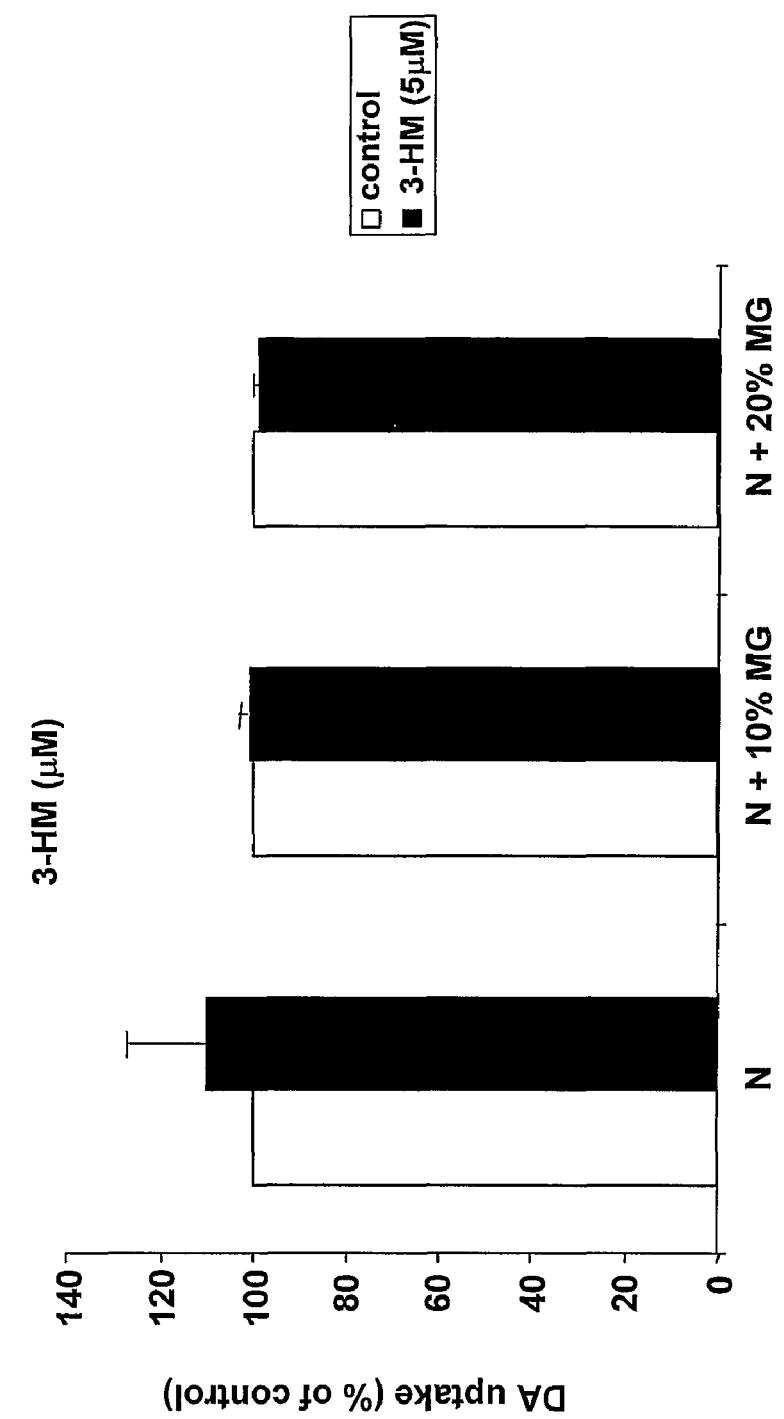
FIG. 55 is a graph showing DA uptake in reconstituted neuron-enriched cultures with 10% or 20% microglia added and treated with various concentrations (1-5 μM) of 3-HM).
Figure 56:
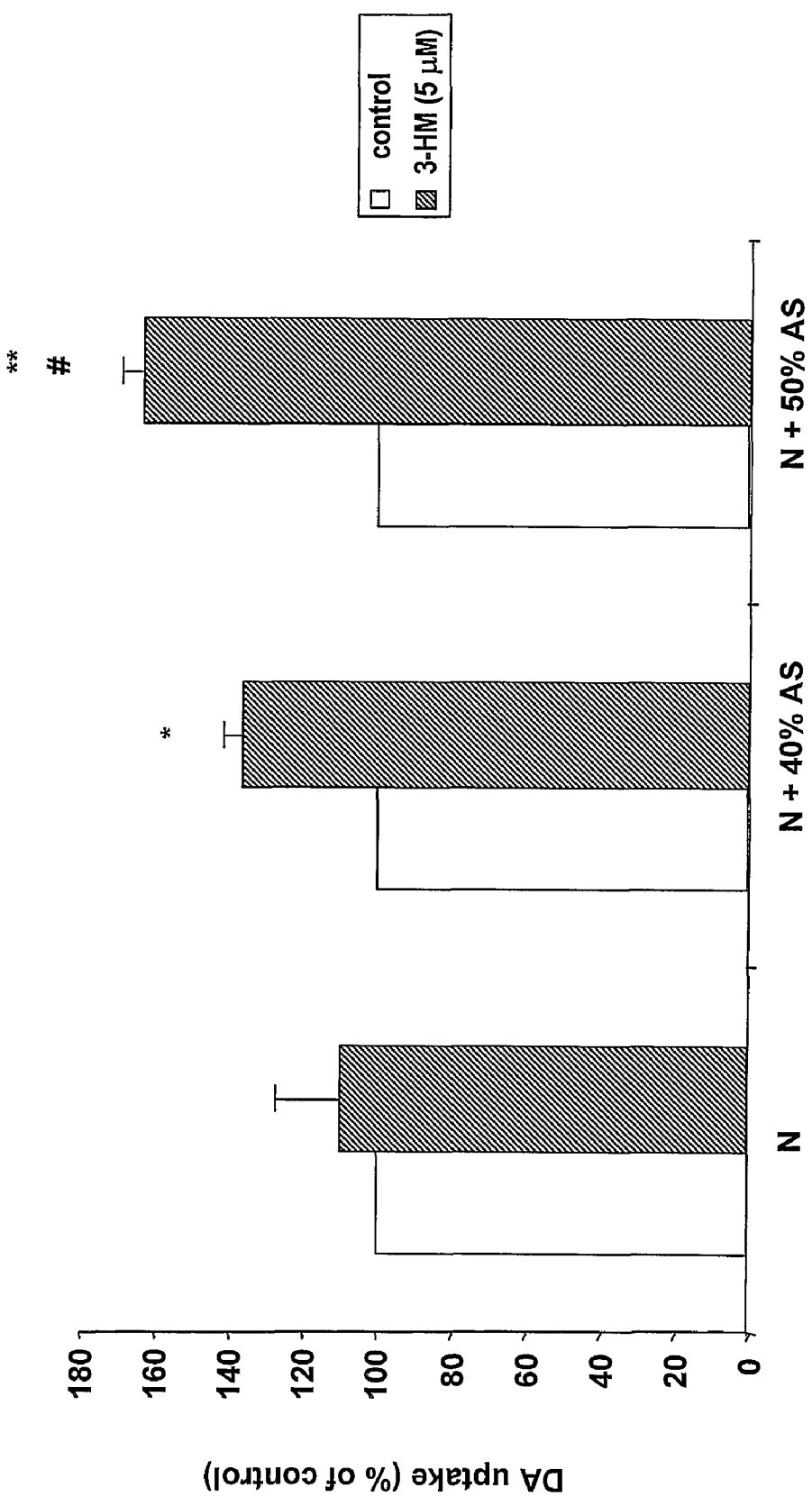
FIG. 56 is a graph showing DA uptake in neuron-enriched cultures with 40% or 50% astroglia added and treated with various concentrations (1-5 μM) of 3-HM.

To examine the possibility that glia cells mediated the 3-HM-induced neurotrophic effect, we performed reconstitution experiments by adding either microglia or astroglia back to the neuron-enriched cultures. Addition of 10% ($5\times10^4$/well) or 20% ($1\times10^5$/well) of microglia back to the neuron-enriched cultures failed to increase DA uptake in the 31-HM-treated cultures (FIG. 55). (Normal mesencephalic neuron-glia cultures contain ~10% microglia). In contrast, addition of 40% ($2\times10^5$/well) or 50% ($2.5\times10^5$/well) of astroglia back to the neuron-enriched cultures increased the capacity of DA uptake by 135.8% and 158.3%, respectively. (Normal mesencephalic neuron-glia cultures contain ~40-50% astroglia). Furthermore, it appeared that the neurotrophic effect of 3-HM was positively correlated with the composition of astroglia (FIG. 56).

Example 30

Figure 57:
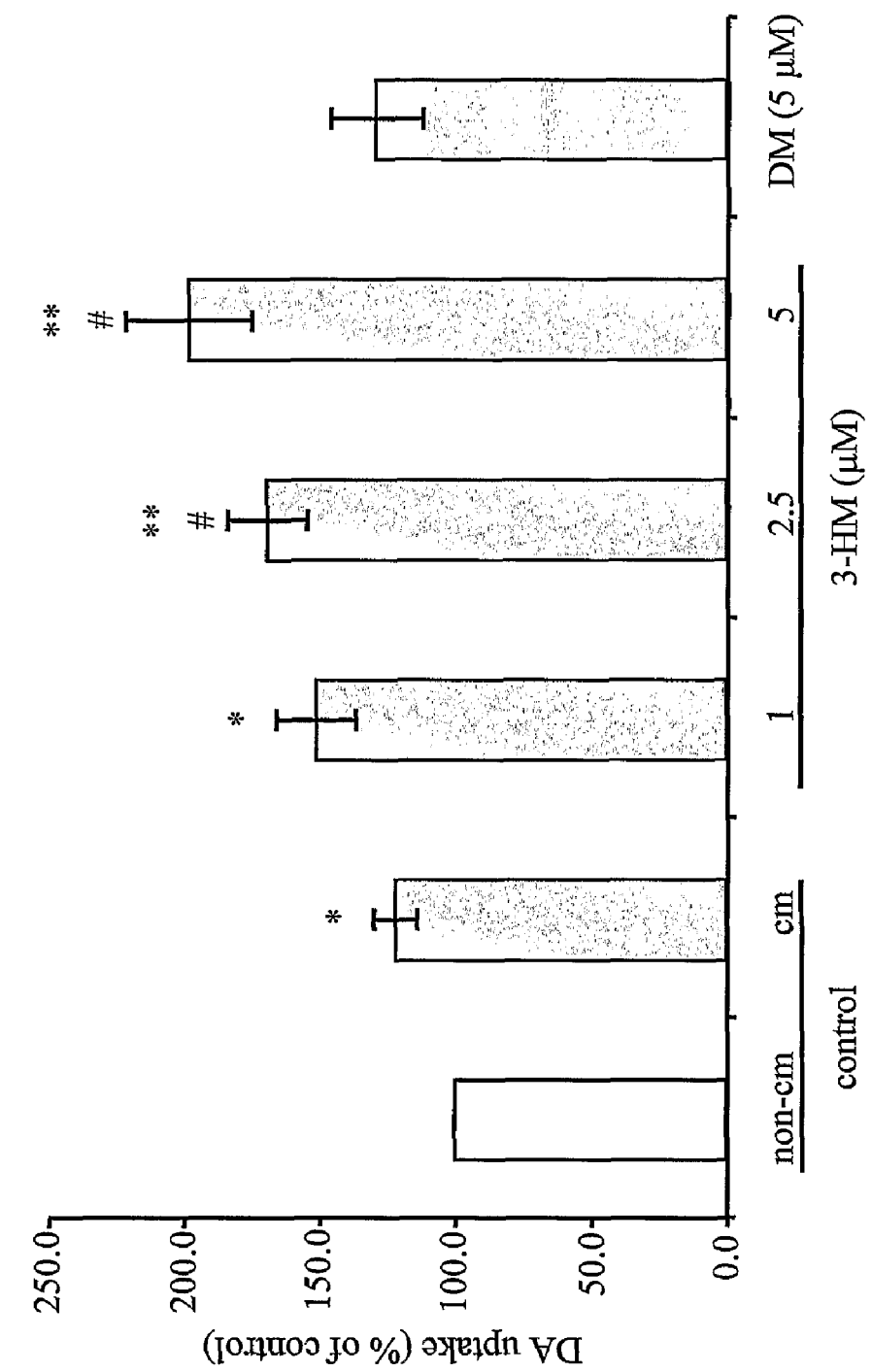
FIG. 57 is a graph showing DA uptake in neuron-enriched cultures with added astroglia-derived conditioned media pretreated with various concentrations of 3-HM (1-5 μM).

3-HM-Treated Astroglia Conditioned Media Increase DA Uptake Capacity in the Neuron-Enriched Cultures To confirm the possible role of astroglia in the neurotrophic effect of 3-HM, conditioned media from astroglia-enriched cultures (prepared as described above) treated with either 3-HM (1-5 µM) or vehicle for 24 hours were prepared. These 3-HM and the vehicle-treated conditioned media were then added to the neuron-enriched cultures in which a new vehicle-treated control culture was viewed as the non-conditioned control. Ten days later, we conducted a DA uptake assay. As shown in FIG. 57, 3-HM (1-5 µM)-treated conditioned media exerted a significant neurotrophic effect on dopaminergic neurons (151.3%, 160.9% and 197.8%, respectively) compared with the non-conditioned control cultures, in a dose-dependent manner. 3-HM (2.5-5 µM)-treated conditioned media had a dramatic neurotrophic effect on dopaminergic neurons (160.9% and 197.8%, respectively) compared with the vehicle-treated conditioned control cultures (122%). However, DM (5 µM), the parent compound of 3-HM, failed to exhibit any neurotrophic effect compared with the vehicle-treated conditioned cultures (FIG. 57). This result is consistent with our previous report indicating that DM by itself has no neurotrophic effect.

Results were expressed as a percentage of the vehicle-treated non-conditioned control cultures and were the mean ±SEM from four independent experiments in triplicate. *$P<0.05$ and **$P<0.001$ compared with the vehicle-treated non-conditioned control cultures. cm, conditioned medium; non-cm, non-conditioned medium.

Treating the mesencephalic neuron-glia cultures with a relatively high dose at 1-5 µM, 3-HM has a neurotrophic effect on dopaminergic neurons against LPS-induced neurotoxicity.

The above specification, examples and data provide a complete description of the manufacture and use of the composition of the invention. Since many embodiments of the invention can be made without departing from the spirit and scope of the invention, the invention resides in the claims hereinafter appended. All references, patent applications, patents referred to herein are hereby incorporated by reference.

We claim:

1. A method of treating a mammal for endotoxic shock by administering to the mammal in need thereof an effective amount of naloxone, wherein the effective amount of naloxone is from 10 pg/kg to 1 μg/kg, thereby treating the endotoxic shock.

2. The method of claim 1, wherein the mammal is a human.

* * * * *

SEQUENCE LISTING

```
<160> NUMBER OF SEQ ID NOS: 24

<210> SEQ ID NO 1
<211> LENGTH: 17
<212> TYPE: PRT
<213> ORGANISM: Homo sapiens

<400> SEQUENCE: 1

Tyr Gly Gly Phe Leu Arg Arg Ile Arg Pro Lys Leu Lys Trp Asp Asn
1               5                   10                  15

Gln

<210> SEQ ID NO 2
<211> LENGTH: 3
<212> TYPE: PRT
<213> ORGANISM: Artificial Sequence
<220> FEATURE:
<223> OTHER INFORMATION: Peptide

<400> SEQUENCE: 2

Gly Gly Phe
1

<210> SEQ ID NO 3
<211> LENGTH: 22
<212> TYPE: DNA
<213> ORGANISM: Artificial Sequence
<220> FEATURE:
<223> OTHER INFORMATION: Forward Primer

<400> SEQUENCE: 3
```

```
cctcaacgga agaaccaaag ag                                              22

<210> SEQ ID NO 4
<211> LENGTH: 20
<212> TYPE: DNA
<213> ORGANISM: Artificial Sequence
<220> FEATURE:
<223> OTHER INFORMATION: Reverse Primer

<400> SEQUENCE: 4
ctcagacagc gaggcacatc                                                 20

<210> SEQ ID NO 5
<211> LENGTH: 19
<212> TYPE: DNA
<213> ORGANISM: Artificial Sequence
<220> FEATURE:
<223> OTHER INFORMATION: Forward Primer

<400> SEQUENCE: 5
gccggatgac aagttccaa                                                  19

<210> SEQ ID NO 6
<211> LENGTH: 21
<212> TYPE: DNA
<213> ORGANISM: Artificial Sequence
<220> FEATURE:
<223> OTHER INFORMATION: Reverse Primer

<400> SEQUENCE: 6
gcctcaagga agccaagaag a                                               21

<210> SEQ ID NO 7
<211> LENGTH: 20
<212> TYPE: DNA
<213> ORGANISM: Artificial Sequence
<220> FEATURE:
<223> OTHER INFORMATION: Forward Primer

<400> SEQUENCE: 7
tggctgggat tcacctcaag                                                 20

<210> SEQ ID NO 8
<211> LENGTH: 21
<212> TYPE: DNA
<213> ORGANISM: Artificial Sequence
<220> FEATURE:
<223> OTHER INFORMATION: Reverse Primer

<400> SEQUENCE: 8
gtggctatga cttcggtttg g                                               21

<210> SEQ ID NO 9
<211> LENGTH: 21
<212> TYPE: DNA
<213> ORGANISM: Artificial Sequence
<220> FEATURE:
<223> OTHER INFORMATION: Forward Primer

<400> SEQUENCE: 9
gtctcggaag ggagccaagt a                                               21

<210> SEQ ID NO 10
<211> LENGTH: 18
<212> TYPE: DNA
<213> ORGANISM: Artificial Sequence
```

```
<220> FEATURE:
<223> OTHER INFORMATION: Reverse Primer

<400> SEQUENCE: 10
cgacgccgct cagaagaa                                                    18

<210> SEQ ID NO 11
<211> LENGTH: 21
<212> TYPE: DNA
<213> ORGANISM: Artificial Sequence
<220> FEATURE:
<223> OTHER INFORMATION: Forward Primer

<400> SEQUENCE: 11
gcccaccaag aacgatagtc a                                                21

<210> SEQ ID NO 12
<211> LENGTH: 22
<212> TYPE: DNA
<213> ORGANISM: Artificial Sequence
<220> FEATURE:
<223> OTHER INFORMATION: Reverse Primer

<400> SEQUENCE: 12
gaaggcaact ggatggaagt ct                                               22

<210> SEQ ID NO 13
<211> LENGTH: 22
<212> TYPE: DNA
<213> ORGANISM: Artificial Sequence
<220> FEATURE:
<223> OTHER INFORMATION: Forward Primer

<400> SEQUENCE: 13
ccaagcctta tcggaaatga tc                                               22

<210> SEQ ID NO 14
<211> LENGTH: 21
<212> TYPE: DNA
<213> ORGANISM: Artificial Sequence
<220> FEATURE:
<223> OTHER INFORMATION: Reverse Primer

<400> SEQUENCE: 14
gatttctggg ccatgcttct c                                                21

<210> SEQ ID NO 15
<211> LENGTH: 18
<212> TYPE: DNA
<213> ORGANISM: Artificial Sequence
<220> FEATURE:
<223> OTHER INFORMATION: Forward Primer

<400> SEQUENCE: 15
actccgagct ggcatcca                                                    18

<210> SEQ ID NO 16
<211> LENGTH: 22
<212> TYPE: DNA
<213> ORGANISM: Artificial Sequence
<220> FEATURE:
<223> OTHER INFORMATION: Reverse Primer

<400> SEQUENCE: 16
cccactgtta acgtggttca tg                                               22
```

```
<210> SEQ ID NO 17
<211> LENGTH: 17
<212> TYPE: DNA
<213> ORGANISM: Artificial Sequence
<220> FEATURE:
<223> OTHER INFORMATION: Forward Primer

<400> SEQUENCE: 17
cgccgctggg aaacttt                                                  17

<210> SEQ ID NO 18
<211> LENGTH: 20
<212> TYPE: DNA
<213> ORGANISM: Artificial Sequence
<220> FEATURE:
<223> OTHER INFORMATION: Reverse Primer

<400> SEQUENCE: 18
tcctggctcg cagattgtaa                                               20

<210> SEQ ID NO 19
<211> LENGTH: 22
<212> TYPE: DNA
<213> ORGANISM: Artificial Sequence
<220> FEATURE:
<223> OTHER INFORMATION: Forward Primer

<400> SEQUENCE: 19
cagatccatt tcaccctcat cc                                            22

<210> SEQ ID NO 20
<211> LENGTH: 20
<212> TYPE: DNA
<213> ORGANISM: Artificial Sequence
<220> FEATURE:
<223> OTHER INFORMATION: Reverse Primer

<400> SEQUENCE: 20
tccagtagca gcagctcagc                                               20

<210> SEQ ID NO 21
<211> LENGTH: 21
<212> TYPE: DNA
<213> ORGANISM: Artificial Sequence
<220> FEATURE:
<223> OTHER INFORMATION: Forward Primer

<400> SEQUENCE: 21
ctcctgtctg tctctccgga a                                             21

<210> SEQ ID NO 22
<211> LENGTH: 20
<212> TYPE: DNA
<213> ORGANISM: Artificial Sequence
<220> FEATURE:
<223> OTHER INFORMATION: Reverse Primer

<400> SEQUENCE: 22
taccctcagt cccctcctca                                               20

<210> SEQ ID NO 23
<211> LENGTH: 22
<212> TYPE: DNA
<213> ORGANISM: Artificial Sequence
<220> FEATURE:
<223> OTHER INFORMATION: Forward Primer

<400> SEQUENCE: 23
```

```
gtatgactcc actcacggca aa                                              22

<210> SEQ ID NO 24
<211> LENGTH: 20
<212> TYPE: DNA
<213> ORGANISM: Artificial Sequence
<220> FEATURE:
<223> OTHER INFORMATION: Reverse Primer

<400> SEQUENCE: 24
ggtctcgctc ctggaagatg                                                 20
```